(12) United States Patent
Chowdari et al.

(10) Patent No.: US 9,156,850 B2
(45) Date of Patent: Oct. 13, 2015

(54) ENEDIYNE COMPOUNDS, CONJUGATES THEREOF, AND USES AND METHODS THEREFOR

(71) Applicant: Bristol-Myers Squibb Company, Princeton, NJ (US)

(72) Inventors: Naidu S. Chowdari, Sunnyvale, CA (US); Sanjeev Gangwar, Foster City, CA (US); Bilal Sufi, San Jose, CA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/203,118

(22) Filed: Mar. 10, 2014

(65) Prior Publication Data

US 2014/0193438 A1    Jul. 10, 2014

Related U.S. Application Data

(62) Division of application No. 13/764,226, filed on Feb. 11, 2013, now Pat. No. 8,709,431.

(60) Provisional application No. 61/598,143, filed on Feb. 13, 2012, provisional application No. 61/653,785, filed on May 31, 2012.

(51) Int. Cl.
| | |
|---|---|
| *A61K 39/00* | (2006.01) |
| *C07D 471/00* | (2006.01) |
| *C07D 489/12* | (2006.01) |
| *C07D 491/00* | (2006.01) |
| *C07D 498/00* | (2006.01) |
| *C07D 513/00* | (2006.01) |
| *C07D 515/00* | (2006.01) |
| *C07K 16/00* | (2006.01) |
| *C12P 21/08* | (2006.01) |
| *A01N 43/42* | (2006.01) |
| *A61K 31/44* | (2006.01) |
| *C07D 491/08* | (2006.01) |
| *C07K 16/18* | (2006.01) |
| *A61K 47/48* | (2006.01) |
| *A61K 31/439* | (2006.01) |

(52) U.S. Cl.
CPC ............ *C07D 491/08* (2013.01); *A61K 31/439* (2013.01); *A61K 47/48384* (2013.01); *C07K 16/18* (2013.01)

(58) Field of Classification Search
CPC .... C07K 16/18; C07D 491/08; A61K 31/439; A61K 47/48384
See application file for complete search history.

(56) References Cited

U.S. PATENT DOCUMENTS

| | | | |
|---|---|---|---|
| 6,214,345 | B1 | 4/2001 | Firestone et al. |
| 6,984,720 | B1 | 1/2006 | Korman et al. |
| 6,989,452 | B2 | 1/2006 | Ng et al. |
| 7,087,600 | B2 | 8/2006 | Ng et al. |
| 7,091,186 | B2 | 8/2006 | Senter et al. |
| 7,129,261 | B2 | 10/2006 | Ng et al. |
| 7,238,352 | B2 | 7/2007 | Gorczynski et al. |
| 7,335,748 | B2 | 2/2008 | Harkins et al. |
| 7,375,078 | B2 | 5/2008 | Feng |
| 7,387,776 | B2 | 6/2008 | Keler et al. |
| 7,517,903 | B2 | 4/2009 | Chen et al. |
| 7,691,962 | B2 | 4/2010 | Boyd et al. |
| 7,714,016 | B2 | 5/2010 | Gangwar et al. |
| 7,847,105 | B2 | 12/2010 | Gangwar et al. |
| 7,968,586 | B2 | 6/2011 | Gangwar et al. |
| 8,008,449 | B2 | 8/2011 | Korman et al. |
| 8,097,703 | B2 | 1/2012 | Rao-Naik et al. |

(Continued)

FOREIGN PATENT DOCUMENTS

| | | |
|---|---|---|
| EP | 0484856 A2 | 5/1992 |
| WO | WO 81/01145 | 4/1981 |

(Continued)

OTHER PUBLICATIONS

Abdel-Magid A "New Synthetic Enediynes and Their Conjugates May Provide Effective Treatment for Cancer" ACS Medicinal Chemistry Letters 4:1018-1019. Published Sep. 20, 2013.*
Davies et al. "Uncialamycin, A New Enediyne Antibiotic" Organic Letters 7:5233-5236. Published 2005.*
Carl, P.L. et al., "A Novel Connector Linkage Applicable in Prodrug Design", Journal of Medicinal Chemistry, vol. 24, No. 5, pp. 479-480 (1981).
Chen, J.S.-H., "Part I. Chemistry and Biology of Uncialamycin, Part II. Total Synthesis of Aspidophytine", Thesis, The Scripps Research Institute, LaJolla, California (Sep. 2008).
Davies, J. et al., "Uncialamycin, A New Enediyne Antibiotic", Organic Letters, vol. 7, No. 23, pp. 5233-5236 (2005).
Desrat, S. et al., "Intramolecular Imino Diels-Alder Reaction: Progress toward the Synthesis of Uncialamycin", J. Org. Chem., vol. 74, No. 17, pp. 6728-6734 (2009).

(Continued)

*Primary Examiner* — Christina Bradley
*Assistant Examiner* — Zachary J Miknis
(74) *Attorney, Agent, or Firm* — Yuan Chao

(57) ABSTRACT

Enediyne compounds having a structure according to formula (I), where $R^0$, $R^2$, $R^3$, $R^4$, $R^5$, $R^6$, and $R^7$ are defined herein, can be used in chemotherapeutic drugs, especially in conjugates, for the treatment of diseases such as cancer.

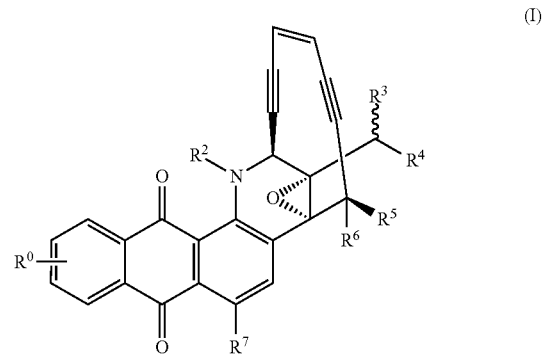

(I)

7 Claims, 13 Drawing Sheets

(56) References Cited

U.S. PATENT DOCUMENTS

| | | | |
|---|---|---|---|
| 8,124,738 B2 | 2/2012 | Terret et al. |
| 8,222,375 B2 | 7/2012 | Terrett et al. |
| 2008/0279868 A1 | 11/2008 | Boyd et al. |
| 2009/0074660 A1 | 3/2009 | Korman et al. |
| 2010/0092484 A1 | 4/2010 | Xu et al. |
| 2010/0113476 A1 | 5/2010 | Chen et al. |
| 2010/0143368 A1 | 6/2010 | King et al. |
| 2010/0145036 A1 | 6/2010 | Sufi et al. |

FOREIGN PATENT DOCUMENTS

| | | |
|---|---|---|
| WO | WO 93/23046 A1 | 11/1993 |
| WO | WO 02/096910 | 12/2002 |
| WO | WO 2007/038868 | 4/2007 |
| WO | WO 2008/083312 | 7/2008 |
| WO | WO 2009/045957 | 4/2009 |

OTHER PUBLICATIONS

Doronina, S.O. et al., "Development of potent monoclonal antibody auristatin conjugates for cancer therapy", Nature Biotechnology, vol. 21, No. 7, pp. 778-784 (2003) and vol. 21, No. 8, p. 941 (2003) (erratum).

Dubowchik, G.M. et al., "Cathepsin B-Labile Dipeptide Linkers for Lysosomal Release of Doxorubicin from Internalizing Immunoconjugates: Model Studies of Enzymatic Drug Release and Antigen-Specific In Vitro Anticancer Activity", Bioconjugate Chem., vol. 13, No. 4, pp. 855-869 (2002).

Dubowchik, G.M. et al., "Cathepsin B-Sensitive Dipeptide Prodrugs. 1. A Model Study of Structural Requirements for Efficient Release of Doxorubicin", Bioorganic & Medicinal Chemistry Letters, vol. 8, pp. 3341-3346 (1998).

Dubowchik, G.M. et al., "Cathepsin B-Sensitive Dipeptide Prodrugs. 2. Models of Anticancer Drugs Paclitaxel (Taxol®), Mitomycin C and Doxorubicin", Bioorganic & Medicinal Chemistry Letters, vol. 8, pp. 3347-3352 (1998).

Dubowchik, G.M. et al., "Receptor-mediated and enzyme-dependent targeting of cytotoxic anticancer drugs", Pharmacology & Therapeutics, vol. 83, pp. 67-123 (1999).

Nicolaou, K.C. et al., "Asymmetric Synthesis and Biological Properties of Uncialamycin and 26-*epi*-Uncialamycin", Angew. Chem. Int. Ed., vol. 47, pp. 185-189 (2008).

Nicolaou, K.C. et al., "From nature to the laboratory and into the clinic", Bioorganic & Medicinal Chemistry, vol. 17, pp. 2290-2303 (2009).

Nicolaou, K.C. et al., "Total Synthesis and Stereochemistry of Uncialamycin", Angew. Chem., vol. 119, pp. 4788-4791 (2007).

Nicolaou, K.C. et al., "Total Synthesis and Stereochemistry of Uncialamycin", Angew. Chem. Int. Ed., vol. 46, pp. 4704-4707 (2007).

Nicolaou, K.C. et al., "Total synthesis of complex heterocyclic natural products", Pure Appl. Chem., vol. 80, No. 4, pp. 727-742 (2008).

Shao, R.-G., "Pharmacology and Therapeutic Applications of Enediyne Antitumor Antibiotics", Current Molecular Pharmacology, vol. 1, No. 1, pp. 50-60 (2008).

Toki, B.E. et al., "Protease-Mediated Fragmentation of *p*-Amidobenzyl Ethers: A New Strategy for the Activation of Anticancer Prodrugs", J. Org. Chem., vol. 67, No. 6, pp. 1866-1872 (2002).

International Search Report and Written Opinion, mailed Apr. 12, 2013, for PCT Application No. PCT/US2013/025247.

* cited by examiner

Activity of Compound (IIa) against HL-60 Leukemia Cells

Activity of Compound (IIa) against Adr Cells

ENEDIYNE COMPOUNDS, CONJUGATES THEREOF, AND USES AND METHODS THEREFOR

CROSS-REFERENCE TO RELATED APPLICATIONS

This application is a divisional of application Ser. No. 13/764,226, filed Feb. 11, 2013, now U.S. Pat. No. 8,709,431, which claims the benefit under 35 U.S.C. §119(e) of US Provisional Applications Nos. 61/598,143, filed Feb. 13, 2012 and 61/653,785, filed May 31, 2012; the disclosures of which are incorporated herein by reference.

BACKGROUND OF THE INVENTION

This invention relates to enediyne compounds and conjugates thereof, methods for making and using such compounds and conjugates, and compositions comprising such compounds and conjugates.

The enediynes are a family of antibiotics that possess a distinctive strained nine- or ten-member ring system comprising a Z-carbon-carbon double bond and two carbon-carbon triple bonds, usually arranged with the latter two flanking the former. The enediynes are potent damagers of DNA, causing single and double strand cuts. Their potency is attributed to their ability to bind to DNA and undergo a Bergmann rearrangement in which the strained ring system is converted into a highly reactive 1,4-benzenoid diradical, which damages the DNA by abstracting hydrogens from it.

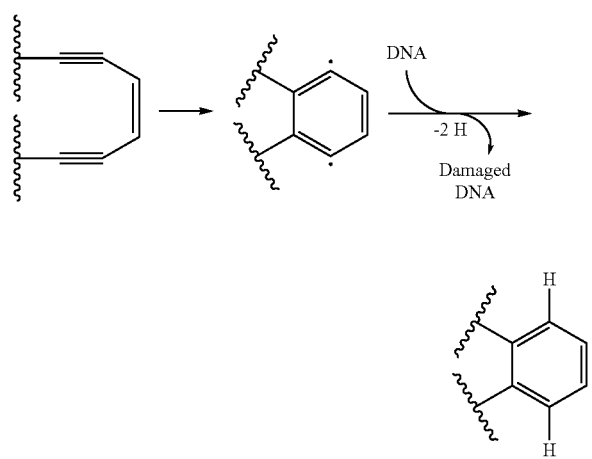

Uncialamycin is an enediyne isolated from a *Streptomyces* strain found on the lichen *Cladonia uncialis* (Davies et al. 2005; 2007). (Full citations for references cited in this specification by first named author or inventor and year are provided in the section entitled "REFERENCES" later herein.)

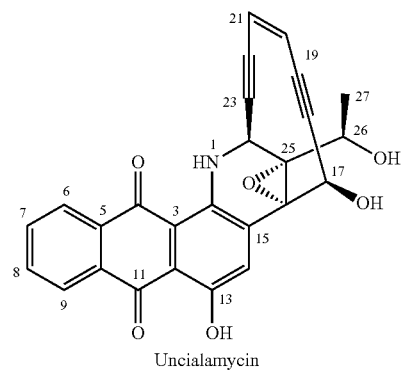 [SMILES: C[C@@H](O)[C@@]12O[C@]13c1cc(O)c4c(c1N[C@H]2C#C/C=C\C#C[C@H]3O)C(=O)c1ccccc1C4=O]

Uncialamycin

The structure of uncialamycin has been confirmed by total synthesis (Nicolaou et al. 2007a; 2007b). In the course of the synthesis, it was noted that the unnatural 26(S) epimer was almost as active as the natural 26(R) epimer—that is, the stereochemistry of the C27 methyl had a minor effect on biological activity. Both epimers were active against several ovarian tumor cell lines. The $IC_{50}$ values ranged from $9\times10^{-12}$ to $1\times10^{-10}$, depending on the epimer and cell line or subline (Nicolaou et al., 2008).

Conjugates are an important method for the delivery of anti-cancer drugs, which are often highly cytotoxic and might otherwise be problematic to administer due to the risk of systemic toxicity. In a conjugate, the drug is conjugated (covalently linked) to a targeting moiety that specifically or preferentially binds to a chemical entity characteristic of the cancer cell, thus delivering the drug there with high specificity. Further, the drug is held in an inactive form until released from the conjugate, usually by cleavage of the covalent linker.

Typically, the targeting moiety is an antibody or an antigen-binding portion thereof, whose antigen is overexpressed or uniquely expressed by a cancer cell ("tumor associated antigen"). In such instances, the resulting conjugate is sometimes referred to as an "immunoconjugate" or an "antibody-drug conjugate" (ADC). Preferably the tumor associated antigen is located on the surface of the cancer cell, but also can be one that is secreted into the vicinal extracellular space. Upon binding, the antigen-conjugate complex is internalized and eventually finds its way inside a vesicular body such as a lysosome, where the covalent linker is cleaved, liberating active drug to exert its chemotherapeutic effect.

Advantageously, the covalent linker is designed such that cleavage is caused by a factor prevalent inside a cancer cell but not in plasma. One such factor is the low lysosomal pH, so that the covalent linker can be an acid-sensitive group such as a hydrazone. Another such factor is the generally higher intracellular concentration of glutathione, allowing for the cleavage of a disulfide covalent linker by a disulfide exchange mechanism. Yet another such factor is the presence of lysosomal enzymes such as cathepsin B, which can cleave peptide linkers designed to be preferred substrates (Dubowchik et al. 2002).

Conjugates have been used to deliver enediyne drugs in oncology. Gemtuzumab ozogamicin (Mylotarg®) is a conjugate of an anti-CD33 monoclonal antibody and a derivative of the enediyne calicheamicin. It was approved for treatment of acute myelogenous leukemia but was later withdrawn from the market. Several other enediyne drugs, especially in the conjugated form, have been the subject of development efforts. For a review, see Shao 2008.

BRIEF SUMMARY OF THE INVENTION

The present invention provides compounds based on an uncialamycin scaffold, which are potent cytotoxins having utility as chemotherapeutic drugs, whether used as such or in conjugates. In one aspect, there is provided a compound having a structure represented formula (I):

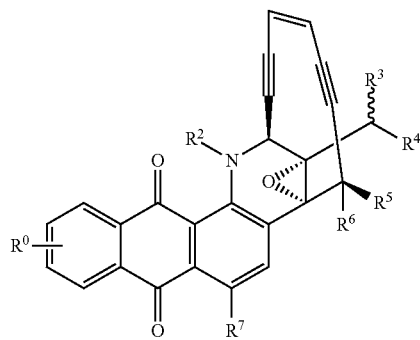

(I)

wherein
$R^0$ is $NHR^{1a}$, $NHC(=O)OR^{1b}$, $NHC(=O)NHR^{1b}$, $OC(=O)NHR^{1b}$, $(CH_2)_{1-4}NHR^{1a}$, F, Cl, Br, $OR^{1a}$, or $SR^{1b}$;

$R^{1a}$ is H, $C_1$-$C_6$ alkyl, $(CH_2)_nNH_2$, $C(=O)(CH_2)_nNH_2$, $C(=O)CHR^8NH_2$, or $C(=O)R^9NH_2$;

$R^{1b}$ is H, $C_1$-$C_6$ alkyl, $(CH_2)_nNH_2$,

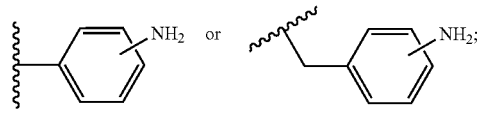

$R^2$ is H, $R^{10}$, $C(=O)R^{10}$, or $C(=O)OR^{10}$;
$R^3$ is H or unsubstituted or substituted $C_1$-$C_6$ alkyl;
$R^4$ is OH, SH, $NH_2$, $OR^{10}$, $SR^{10}$, $NHR^{10}$, $N(R^{10})_2$, $NHC(=O)OR^{10}$, $OC(=O)NHR^{1b}$, $OC(=O)R^{10}$, $SC(=O)R^{10}$, or $NHC(=O)R^{10}$;
$R^5$ is OH, SH, $NH_2$, $OR^{10}$, $SR^{10}$, $NHR^{10}$, $N(R^{10})_2$, $NHC(=O)OR^{10}$, $OC(=O)NHR^{1b}$, $OC(=O)R^{10}$, $SC(=O)R^{10}$, or $NHC(=O)R^{10}$;
$R^6$ is H or unsubstituted or substituted $C_1$-$C_6$ alkyl; or $R^5$ and $R^6$ combine to form $=O$;
$R^7$ is OH, SH, $NH_2$, $OR^{10}$, $SR^{10}$, $NHR^{10}$, $N(R^{10})_2$, $NHC(=O)OR^{10}$, $OC(=O)NHR^{1b}$, $OC(=O)R^{10}$, $SC(=O)R^{10}$, or $NHC(=O)R^{10}$;
$R^8$ is the side chain residue of an α-amino acid selected from the group consisting of alanine, arginine, asparagine, aspartic acid, γ-carboxyglutamic acid, citrulline, cysteine, glutamic acid, glutamine, glycine, histidine, isoleucine, leucine, lysine, methionine, norleucine, norvaline, ornithine, phenylalanine, serine, threonine, tryptophan, tyrosine, and valine;
$R^9$ is unsubstituted or substituted arylene, unsubstituted or substituted heteroarylene, unsubstituted or substituted alkylarylene, unsubstituted or substituted cycloalkylene or unsubstituted or substituted heterocycloalkylene;
each $R^{10}$ is independently unsubstituted or substituted $C_1$-$C_6$ alkyl, unsubstituted or substituted cycloalkyl, unsubstituted or substituted heterocycloalkyl, unsubstituted or substituted arylalkyl, unsubstituted or substituted aryl; or unsubstituted or substituted heteroaryl; and
n is 2, 3, 4, 5, or 6;
or a pharmaceutically acceptable salt thereof
Preferably, in formula (I) $R^0$ is $NHR^{1a}$.

The group $NHR^{1a}$ can be attached to any of the carbon atoms at positions 6, 7, 8, or 9 (see structural formula for uncialamycin, above, for numbering of carbon atoms). Thus, the structure of formula (I) can be equivalently depicted by formula (I')

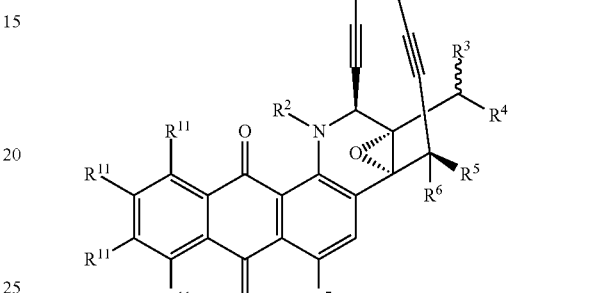

(I')

where one of the $R^{11}$ groups is $R^0$ and the remaining $R^{11}$ groups are each H and $R^0$, $R^2$, $R^3$, $R^4$, $R^5$, $R^6$, and $R^7$ are as defined above for formula (I).

Uncialamycin is a potential candidate for the drug component in a conjugate, but it lacks functional groups that are readily usable as sites for conjugation to a targeting moiety without compromising biological activity. We have discovered that one can introduce a $R^0$ group to the leftmost aromatic ring in the anthraquinone moiety, as shown in formula (I), without unacceptable loss of biological activity and, further, that the $R^0$ group is a versatile site for conjugation. Thus, in another embodiment, this invention provides a conjugate comprising a compound according to formula (I) covalently linked to a targeting moiety that specifically or preferentially binds to a chemical entity on a target cell, which preferably is a cancer cell. Preferably, the targeting moiety is an antibody—more preferably a monoclonal antibody and even more preferably a human monoclonal antibody—and the chemical entity is a tumor associated antigen.

In another embodiment, there is provided a composition of matter comprising a compound of this invention and a linker moiety having a reactive functional group, suitable for conjugation to a targeting moiety.

In another embodiment, this invention provides a method for inhibiting the proliferation of cancer cells in a subject suffering from cancer, comprising administering to the subject a therapeutically effective amount of a compound of this invention or a conjugate thereof with a targeting moiety (particularly an antibody). The cancer cells can be leukemia, renal cancer, ovarian cancer, lung cancer, colon cancer, breast cancer, or prostate cancer cells.

In another embodiment, there is provided a method of treating a cancer in a subject suffering from such cancer, comprising administering to the subject a therapeutically effective amount of a compound of this invention or a conjugate thereof with a targeting moiety (particularly an antibody). In another embodiment, there is provided the use of a compound of this invention or a conjugate thereof with a targeting moiety (particularly an antibody) for the preparation of a medicament for the treatment of cancer in a subject suffering from such cancer. The cancer can be leukemia, renal cancer, ovarian cancer, lung cancer, colon cancer, breast cancer, or prostate cancer.

BRIEF DESCRIPTION OF THE DRAWING(S)

Figure 13A:
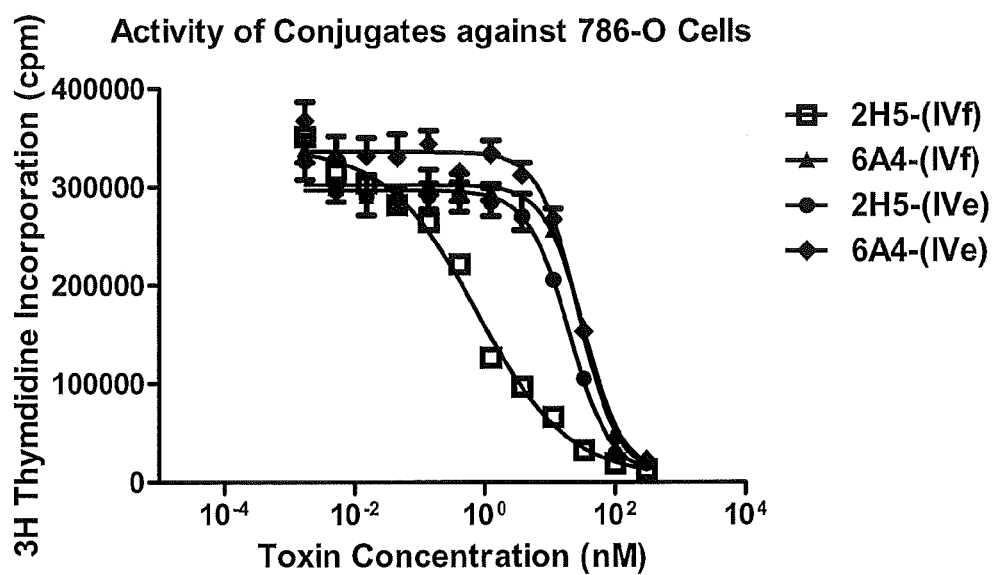
Figure 13B:
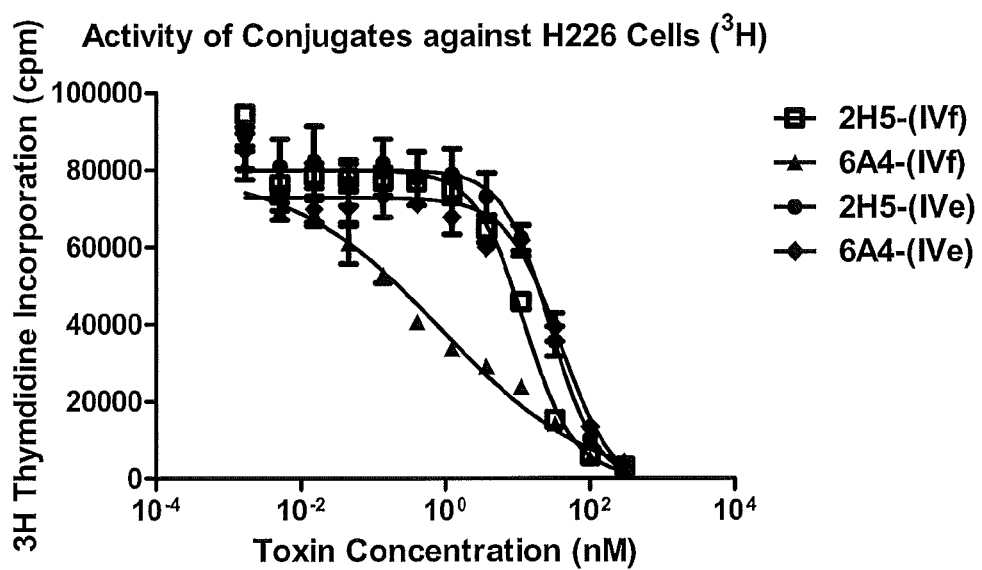
Figure 13C:
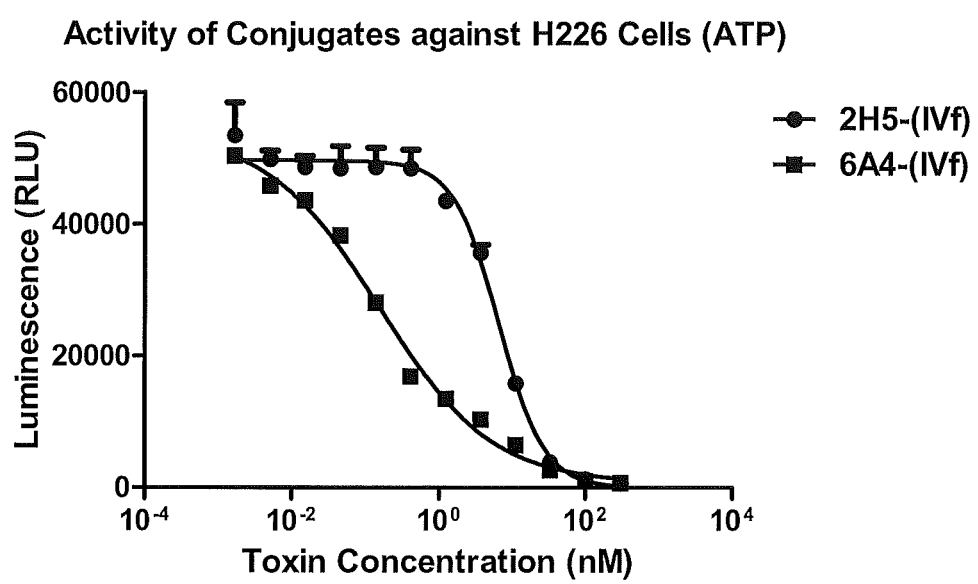

FIGS. 13a, 13b, and 13c show plots of the antiproliferative activity of antibody-drug conjugates made from compounds of this invention.

DETAILED DESCRIPTION OF THE INVENTION

Definitions

"Antibody" means whole antibodies and any antigen binding fragment (i.e., "antigen-binding portion") or single chain variants thereof. A whole antibody is a protein comprising at least two heavy (H) chains and two light (L) chains interconnected by disulfide bonds. Each heavy chain comprises a heavy chain variable region ($V_H$) and a heavy chain constant region comprising three domains, $C_{H1}$, $C_{H2}$ and $C_{H3}$. Each light chain comprises a light chain variable region ($V_L$ or $V_k$) and a light chain constant region comprising one single domain, $C_L$. The $V_H$ and $V_L$ regions can be further subdivided into regions of hypervariability, termed complementarity determining regions (CDRs), interspersed with more conserved framework regions (FRs). Each $V_H$ and $V_L$ comprises three CDRs and four FRs, arranged from amino- to carboxy-terminus in the following order: FR1, CDR1, FR2, CDR2, FR3, CDR3, and FR4. The variable regions contain a binding domain that interacts with an antigen. The constant regions may mediate the binding of the antibody to host tissues or factors, including various cells of the immune system (e.g., effector cells) and the first component (Clq) of the classical complement system. An antibody is said to "specifically bind" to an antigen X if the antibody binds to antigen X with a $K_D$ of $5\times10^{-8}$ M or less, more preferably $1\times10^{-8}$ M or less, more preferably $6\times10^{-9}$ M or less, more preferably $3\times10^{-9}$ M or less, even more preferably $2\times10^{-9}$ M or less. The antibody can be chimeric, humanized, or, preferably, human. The heavy chain constant region can be engineered to affect glycosylation type or extent, to extend antibody half-life, to enhance or reduce inter-actions with effector cells or the complement system, or to modulate some other property. The engineering can be accomplished by replacement, addition, or deletion of one or more amino acids or by replacement of a domain with a domain from another immunoglobulin type, or a combination of the foregoing.

"Antigen binding fragment" and "antigen binding portion" of an antibody (or simply "antibody portion" or "antibody fragment") mean one or more fragments of an antibody that retain the ability to specifically bind to an antigen. It has been shown that the antigen-binding function of an antibody can be performed by fragments of a full-length antibody, such as (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fab' fragment, which is essentially an Fab with part of the hinge region (see, for example, Abbas et al., *Cellular and Molecular Immunology*, 6th Ed., Saunders Elsevier 2007); (iv) a Fd fragment consisting of the $V_H$ and $C_{H1}$ domains; (v) a Fv fragment consisting of the $V_L$ and $V_H$ domains of a single arm of an antibody, (vi) a dAb fragment (Ward et al., (1989) *Nature* 341:544-546), which consists of a $V_H$ domain; (vii) an isolated complementarity determining region (CDR); and (viii) a nanobody, a heavy chain variable region containing a single variable domain and two constant domains. Furthermore, although the two domains of the Fv fragment, $V_L$ and $V_H$, are encoded by separate genes, they can be joined, using recombinant methods, by a synthetic linker that enables them to be made as a single protein chain in which the $V_L$ and $V_H$ regions pair to form monovalent molecules (known as single chain Fv, or scFv); see, e.g., Bird et al. (1988) *Science* 242:423-426; and Huston et al. (1988) *Proc. Natl. Acad. Sci. USA* 85:5879-5883). Such single chain antibodies are also encompassed within the term "antigen-binding portion" of an antibody.

An "isolated antibody" means an antibody that is substantially free of other antibodies having different antigenic specificities (e.g., an isolated antibody that specifically binds antigen X is substantially free of antibodies that specifically bind antigens other than antigen X). An isolated antibody that specifically binds antigen X may, however, have cross-reactivity to other antigens, such as antigen X molecules from other species. In certain embodiments, an isolated antibody specifically binds to human antigen X and does not cross-react with other (non-human) antigen X antigens. Moreover, an isolated antibody may be substantially free of other cellular material and/or chemicals.

"Monoclonal antibody" or "monoclonal antibody composition" means a preparation of antibody molecules of single molecular composition, which displays a single binding specificity and affinity for a particular epitope.

"Human antibody" means an antibody having variable regions in which both the framework and CDR regions (and the constant region, if present) are derived from human germline immunoglobulin sequences. Human antibodies may include later modifications, including natural or synthetic modifications. Human antibodies may include amino acid residues not encoded by human germline immunoglobulin sequences (e.g., mutations introduced by random or site-specific mutagenesis in vitro or by somatic mutation in vivo). However, "human antibody" does not include antibodies in which CDR sequences derived from the germline of another mammalian species, such as a mouse, have been grafted onto human framework sequences.

"Human monoclonal antibody" means an antibody displaying a single binding specificity, which has variable regions in which both the framework and CDR regions are derived from human germline immunoglobulin sequences. In one embodiment, human monoclonal antibodies are produced by a hybridoma that includes a B cell obtained from a transgenic nonhuman animal, e.g., a transgenic mouse, having a genome comprising a human heavy chain transgene and a light chain transgene fused to an immortalized cell.

"Aliphatic" means a straight- or branched-chain, saturated or unsaturated, non-aromatic hydrocarbon moiety having the specified number of carbon atoms (e.g., as in "$C_3$ aliphatic," "$C_1$-$C_5$ aliphatic," or "$C_1$ to $C_5$ aliphatic," the latter two phrases being synonymous for an aliphatic moiety having from 1 to 5 carbon atoms) or, where the number of carbon atoms is not explicitly specified, from 1 to 4 carbon atoms (2 to 4 carbons in the instance of unsaturated aliphatic moieties).

"Alkyl" means a saturated aliphatic moiety, with the same convention for designating the number of carbon atoms being applicable. By way of illustration, $C_1$-$C_4$ alkyl moieties include, but are not limited to, methyl, ethyl, propyl, isopropyl, isobutyl, t-butyl, 1-butyl, 2-butyl, and the like. "Alkylene" means a divalent counterpart of an alkyl group, such as $CH_2CH_2$, $CH_2CH_2CH_2$, and $CH_2CH_2CH_2CH_2$.

"Alkenyl" means an aliphatic moiety having at least one carbon-carbon double bond, with the same convention for designating the number of carbon atoms being applicable. By way of illustration, $C_2$-$C_4$ alkenyl moieties include, but are not limited to, ethenyl (vinyl), 2-propenyl(allyl or prop-2-enyl), cis-1-propenyl, trans-1-propenyl, E- (or Z-) 2-butenyl, 3-butenyl, 1,3-butadienyl(but-1,3-dienyl) and the like.

"Alkynyl" means an aliphatic moiety having at least one carbon-carbon triple bond, with the same convention for designating the number of carbon atoms being applicable. By way of illustration, $C_2$-$C_4$ alkynyl groups include ethynyl (acetylenyl), propargyl(prop-2-ynyl), 1-propynyl, but-2-ynyl, and the like.

"Cycloaliphatic" means a saturated or unsaturated, non-aromatic hydrocarbon moiety having from 1 to 3 rings, each ring having from 3 to 8 (preferably from 3 to 6) carbon atoms. "Cycloalkyl" means a cycloaliphatic moiety in which each ring is saturated. "Cycloalkenyl" means a cycloaliphatic moiety in which at least one ring has at least one carbon-carbon double bond. "Cycloalkynyl" means a cycloaliphatic moiety in which at least one ring has at least one carbon-carbon triple bond. By way of illustration, cycloaliphatic moieties include, but are not limited to, cyclopropyl, cyclobutyl, cyclopentyl, cyclopentenyl, cyclohexyl, cyclohexenyl, cycloheptyl, cyclooctyl, and adamantyl. Preferred cycloaliphatic moieties are cycloalkyl ones, especially cyclopropyl, cyclobutyl, cyclopentyl, and cyclohexyl. "Cycloalkylene" means a divalent counterpart of a cycloalkyl group.

"Heterocycloaliphatic" means a cycloaliphatic moiety wherein, in at least one ring thereof, up to three (preferably 1 to 2) carbons have been replaced with a heteroatom independently selected from N, O, or S, where the N and S optionally may be oxidized and the N optionally may be quaternized. Similarly, "heterocycloalkyl," "heterocycloalkenyl," and "heterocycloalkynyl" means a cycloalkyl, cycloalkenyl, or cycloalkynyl moiety, respectively, in which at least one ring thereof has been so modified. Exemplary heterocycloaliphatic moieties include aziridinyl, azetidinyl, 1,3-dioxanyl, oxetanyl, tetrahydrofuryl, pyrrolidinyl, piperidinyl, piperazinyl, tetrahydropyranyl, tetrahydrothiopyranyl, tetrahydrothiopyranyl sulfone, morpholinyl, thiomorpholinyl, thiomorpholinyl sulfoxide, thiomorpholinyl sulfone, 1,3-dioxolanyl, tetrahydro-1,1-dioxothienyl, 1,4-dioxanyl, thietanyl, and the like. "Heterocycloalkylene" means a divalent counterpart of a heterocycloalkyl group.

"Alkoxy," "aryloxy," "alkylthio," and "arylthio" mean —O(alkyl), —O(aryl), —S(alkyl), and —S(aryl), respectively. Examples are methoxy, phenoxy, methylthio, and phenylthio, respectively.

"Halogen" or "halo" means fluorine, chlorine, bromine or iodine.

"Aryl" means a hydrocarbon moiety having a mono-, bi-, or tricyclic ring system wherein each ring has from 3 to 7 carbon atoms and at least one ring is aromatic. The rings in the ring system may be fused to each other (as in naphthyl) or bonded to each other (as in biphenyl) and may be fused to or bonded to non-aromatic rings (as in indanyl or cyclohexylphenyl). By way of further illustration, aryl moieties include, but are not limited to, phenyl, naphthyl, tetrahydronaphthyl, indanyl, biphenyl, phenanthryl, anthracenyl, and acenaphthyl. "Arylene" means a divalent counterpart of an aryl group, for example 1,2-phenylene, 1,3-phenylene, or 1,4-phenylene.

"Heteroaryl" means a moiety having a mono-, bi-, or tricyclic ring system wherein each ring has from 3 to 7 carbon atoms and at least one ring is an aromatic ring containing from 1 to 4 heteroatoms independently selected from from N, O, or S, where the N and S optionally may be oxidized and the N optionally may be quaternized. Such at least one heteroatom containing aromatic ring may be fused to other types of rings (as in benzo-furanyl or tetrahydroisoquinolyl) or directly bonded to other types of rings (as in phenylpyridyl or 2-cyclopentylpyridyl). By way of further illustration, heteroaryl moieties include pyrrolyl, furanyl, thiophenyl (thienyl), imidazolyl, pyrazolyl, oxazolyl, isoxazolyl, thiazolyl, isothiazolyl, triazolyl, tetrazolyl, pyridyl, N-oxopyridyl, pyridazinyl, pyrimidinyl, pyrazinyl, quinolinyl, isoquinolynyl, quinazolinyl, cinnolinyl, quinoxalinyl, naphthyridinyl, benzo-furanyl, indolyl, benzothiophenyl, oxadiazolyl, thiadiazolyl, phenothiazolyl, benzimidazolyl, benzotriazolyl, dibenzofuranyl, carbazolyl, dibenzothiophenyl, acridinyl, and the like. "Heteroarylene" means a divalent counterpart of an aryl group.

Where it is indicated that a moiety may be substituted, such as by use of "unsubstituted or substituted" or "optionally substituted" phrasing as in "unsubstituted or substituted $C_1$-$C_5$ alkyl" or "optionally substituted heteroaryl," such moiety may have one or more independently selected substituents, preferably one to five in number, more preferably one or two in number. Substituents and substitution patterns can be selected by one of ordinary skill in the art, having regard for the moiety to which the substituent is attached, to provide compounds that are chemically stable and that can be synthesized by techniques known in the art as well as the methods set forth herein.

"Arylalkyl," (heterocycloaliphatic)alkyl," "arylalkenyl," "arylalkynyl," "biarylalkyl," and the like mean an alkyl, alkenyl, or alkynyl moiety, as the case may be, substituted with an aryl, heterocycloaliphatic, biaryl, etc., moiety, as the case may be, with the open (unsatisfied) valence at the alkyl, alkenyl, or alkynyl moiety, for example as in benzyl, phenethyl, N-imidazoylethyl, N-morpholinoethyl, and the like. Conversely, "alkylaryl," "alkenylcycloalkyl," and the like mean an aryl, cycloalkyl, etc., moiety, as the case may be, substituted with an alkyl, alkenyl, etc., moiety, as the case may be, for example as in methylphenyl (tolyl) or allylcyclohexyl. "Hydroxyalkyl," "haloalkyl," "alkylaryl," "cyanoaryl," and the like mean an alkyl, aryl, etc., moiety, as the case may be, substituted with one or more of the identified substituent (hydroxyl, halo, etc., as the case may be).

By way of illustration, permissible substituents include, but are not limited to, alkyl (especially methyl or ethyl), alkenyl (especially allyl), alkynyl, aryl, heteroaryl, cycloaliphatic, heterocycloaliphatic, halo (especially fluoro), haloalkyl (especially trifluoromethyl), hydroxyl, hydroxyalkyl (especially hydroxyethyl), cyano, nitro, alkoxy, —O(hydroxyalkyl), —O(haloalkyl) (especially —OCF$_3$), —O(cycloalkyl), —O(heterocycloalkyl), —O(aryl), alkylthio, arylthio, =O, =NH, =N(alkyl), =NOH, =NO(alkyl), —C(=O)(alkyl), —C(=O)H, —CO$_2$H, —C(=O)NHOH, —C(=O)O(alkyl), —C(=O)O(hydroxyalkyl), —C(=O)NH$_2$, —C(=O)NH(alkyl), —C(=O)N(alkyl)$_2$, —OC(=O)(alkyl), —OC(=O)(hydroxyalkyl), —OC(=O)O(alkyl), —OC(=O)O(hydroxyalkyl), —OC(=O)NH$_2$, —OC(=O)NH(alkyl), —OC(=O)N(alkyl)$_2$, azido, —NH$_2$, —NH(alkyl), —N(alkyl)$_2$, —NH(aryl), —NH(hydroxyalkyl), —NHC(=O)(alkyl), —NHC(=O)H, —NHC(=O)NH$_2$, —NHC(=O)NH(alkyl), —NHC(=O)N(alkyl)$_2$, —NHC(=NH)NH$_2$, —OSO$_2$(alkyl), —SH, —S(alkyl), —S(aryl), —S(cycloalkyl), —S(=O)alkyl, —SO$_2$(alkyl), —SO$_2$NH$_2$, —SO$_2$NH(alkyl), —SO$_2$N(alkyl)$_2$, and the like.

Where the moiety being substituted is an aliphatic moiety, preferred substituents are aryl, heteroaryl, cycloaliphatic, heterocycloaliphatic, halo, hydroxyl, cyano, nitro, alkoxy, —O(hydroxyalkyl), —O(haloalkyl), —O(cycloalkyl), —O(heterocycloalkyl), —O(aryl), alkylthio, arylthio, =O, =NH, =N(alkyl), =NOH, =NO(alkyl), —CO$_2$H, —C(=O)NHOH, —C(=O)O(alkyl), —C(=O)O(hydroxyalkyl), —C(=O)NH$_2$, —C(=O)NH(alkyl), —C(=O)N(alkyl)$_2$, —OC(=O)(alkyl), —OC(=O)(hydroxyalkyl), —OC(=O)O(alkyl), —OC(=O)O(hydroxyalkyl), —OC(=O)NH$_2$, —OC(=O)NH(alkyl), —OC(=O)N(alkyl)$_2$, azido, —NH$_2$, —NH(alkyl), —NH(alkyl)$_2$, —NH(aryl), —NH(hydroxyalkyl), —NHC(=O)(alkyl), —NHC(=O)H, —NHC(=O)NH$_2$, —NHC(=O)NH(alkyl), —NHC(=O)N(alkyl)$_2$, —NHC(=NH)NH$_2$, —OSO$_2$(alkyl), —SH, —S(alkyl), —S(aryl), —S(=O)alkyl, —S(cycloalkyl), —SO$_2$(alkyl), —SO$_2$NH$_2$, —SO$_2$NH(alkyl), and —SO$_2$N(alkyl)$_2$. More preferred substituents are halo, hydroxyl, cyano, nitro, alkoxy, —O(aryl), =O, =NOH, =NO(alkyl), —OC(=O)(alkyl), —OC(=O)O(alkyl), —OC(=O)NH$_2$, —OC(=O)NH(alkyl), —OC(=O)N(alkyl)$_2$, azido, —NH$_2$, —NH(alkyl), —N(alkyl)$_2$, —NH(aryl), —NHC(=O)(alkyl), —NHC(=O)H, —NHC(=O)NH$_2$, —NHC(=O)NH(alkyl), —NHC(=O)N(alkyl)$_2$, and —NHC(=NH)NH$_2$. Especially preferred are phenyl, cyano, halo, hydroxyl, nitro, C$_1$-C$_4$alkyoxy, O(C$_2$-C$_4$ alkylene)OH, and O(C$_2$-C$_4$ alkylene)halo.

Where the moiety being substituted is a cycloaliphatic, heterocycloaliphatic, aryl, or heteroaryl moiety, preferred substituents are alkyl, alkenyl, alkynyl, halo, haloalkyl, hydroxyl, hydroxyalkyl, cyano, nitro, alkoxy, —O(hydroxyalkyl), —O(haloalkyl), —O(aryl), —O(cycloalkyl), —O(heterocycloalkyl), alkylthio, arylthio, —C(=O)(alkyl), —C(=O)H, —CO$_2$H, —C(=O)NHOH, —C(=O)O(alkyl), —C(=O)O(hydroxyalkyl), —C(=O)NH$_2$, —C(=O)NH(alkyl), —C(=O)N(alkyl)$_2$, —OC(=O)(alkyl), —OC(=O)(hydroxyalkyl), —OC(=O)O(alkyl), —OC(=O)O(hydroxyalkyl), —OC(=O)NH$_2$, —OC(=O)NH(alkyl), —OC(=O)N(alkyl)$_2$, azido, —NH$_2$, —NH(alkyl), —N(alkyl)$_2$, —NH(aryl), —NH(hydroxyalkyl), —NHC(=O)(alkyl), —NHC(=O)H, —NHC(=O)NH$_2$, —NHC(=O)NH(alkyl), —NHC(=O)N(alkyl)$_2$, —NHC(=NH)NH$_2$, —OSO$_2$(alkyl), —SH, —S(alkyl), —S(aryl), —S(cycloalkyl), —S(=O)alkyl, —SO$_2$(alkyl), —SO$_2$NH$_2$, —SO$_2$NH(alkyl), and —SO$_2$N(alkyl)$_2$. More preferred substituents are alkyl, alkenyl, halo, haloalkyl, hydroxyl, hydroxyalkyl, cyano, nitro, alkoxy, —O(hydroxyalkyl), —C(=O)(alkyl), —C(=O)H, —CO$_2$H, —C(=O)NHOH, —C(=O)O(alkyl), —C(=O)O(hydroxyalkyl), —C(=O)NH$_2$, —C(=O)NH(alkyl), —C(=O)N(alkyl)$_2$, —OC(=O)(alkyl), —OC(=O)(hydroxyalkyl), —OC(=O)O(alkyl), —OC(=O)O(hydroxyalkyl), —OC(=O)NH$_2$, —OC(=O)NH(alkyl), —OC(=O)N(alkyl)$_2$, —NH$_2$, —NH(alkyl), —N(alkyl)$_2$, —NH(aryl), —NHC(=O)(alkyl), —NHC(=O)H, —NHC(=O)NH$_2$, —NHC(=O)NH(alkyl), —NHC(=O)N(alkyl)$_2$, and —NHC(=NH)NH$_2$. Especially preferred are C$_1$-C$_4$ alkyl, cyano, nitro, halo, and C$_1$-C$_4$alkoxy.

Where a range is stated, as in "C$_1$-C$_5$ alkyl" or "5 to 10%," such range includes the end points of the range, as in C$_1$ and C$_5$ in the first instance and 5% and 10% in the second instance.

Unless particular stereoisomers are specifically indicated (e.g., by a bolded or dashed bond at a relevant stereocenter in a structural formula, by depiction of a double bond as having E or Z configuration in a structural formula, or by use stereochemistry-designating nomenclature), all stereoisomers are included within the scope of the invention, as pure compounds as well as mixtures thereof. Unless otherwise indicated, individual enantiomers, diastereomers, geometrical isomers, and combinations and mixtures thereof are all encompassed by the present invention.

Those skilled in the art will appreciate that compounds may have tautomeric forms (e.g., keto and enol forms), resonance forms, and zwitterionic forms that are equivalent to those depicted in the structural formulae used herein and that the structural formulae encompass such tautomeric, resonance, or zwitterionic forms.

"Pharmaceutically acceptable ester" means an ester that hydrolyzes in vivo (for example in the human body) to produce the parent compound or a salt thereof or has per se activity similar to that of the parent compound. Suitable esters include C$_1$-C$_5$ alkyl, C$_2$-C$_5$ alkenyl or C$_2$-C$_5$ alkynyl esters, especially methyl, ethyl or n-propyl.

"Pharmaceutically acceptable salt" means a salt of a compound suitable for pharmaceutical formulation. Where a compound has one or more basic groups, the salt can be an acid addition salt, such as a sulfate, hydrobromide, tartrate, mesylate, maleate, citrate, phosphate, acetate, pamoate (embonate), hydroiodide, nitrate, hydrochloride, lactate, methylsulfate, fumarate, benzoate, succinate, mesylate, lactobionate, suberate, tosylate, and the like. Where a compound has one or more acidic groups, the salt can be a salt such as a calcium salt, potassium salt, magnesium salt, meglumine salt, ammonium salt, zinc salt, piperazine salt, tromethamine salt, lithium salt, choline salt, diethylamine salt, 4-phenylcyclohexylamine salt, benzathine salt, sodium salt, tetramethylammonium salt, and the like. Polymorphic crystalline forms and solvates are also encompassed within the scope of this invention.

Compositions

A preferred embodiment according to formula (I) is a compound having a structure represented by formula (Ia), or a pharmaceutically acceptable salt thereof. In this embodiment a group NHR$^{1a}$ is attached to C6, wherein R$^{1a}$ is as defined hereinabove in the context of formula (I):

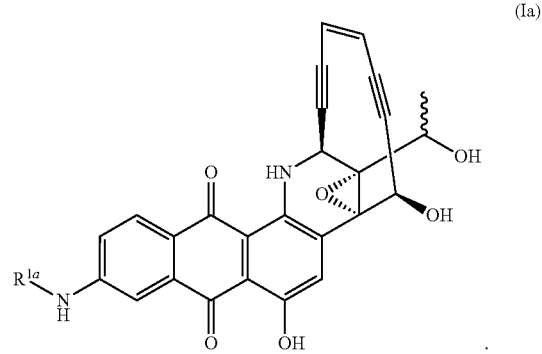

(Ia)

A more preferred embodiment is a compound having a structure represented by formula (Ib), or a pharmaceutically acceptable salt thereof, where R$^{1a}$ is as defined hereinabove in the context of formula (I). In formula (Ib) the stereochemistry of the C27-methyl corresponds to that of the naturally occurring uncialamycin (see structural formula for uncialamycin, supra).

(Ib)

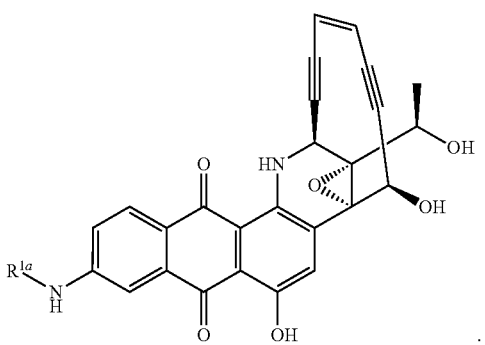

In each of $R^0$, $R^{1a}$, $R^{1b}$, $R^2$, $R^3$, $R^4$, $R^5$, $R^6$, and $R^7$, where they occur in formula (I) or other formulae elsewhere in this specification, where an alkyl, alkylene, aryl, arylene, heteroaryl, heteroarylene, cycloalkyl, cycloalkylene, heterocloalkyl, or heterocycloalkylene group is indicated as being either unsubstituted or substituted, the unsubstituted embodiment is preferred. Where it occurs in formula (I) or in other formulae elsewhere in this specification, $R^2$ preferably is H or $C_1$-$C_3$ alkyl, more preferably H. Where it occurs in formula (I) or in other formulae elsewhere in this application, $R^3$ preferably is $C_1$-$C_3$ alkyl, more preferably Me. Where it occurs in formula (I) or in other formulae elsewhere in this specification, $R^4$ preferably is OH, $OR^{10}$, or $OC(=O)R^{10}$ (with $R^{10}$ preferably being $C_1$-$C_3$ alkyl), more preferably OH. Where it occurs in formula (I) or in other formulae elsewhere in this specification, $R^5$ preferably is OH, $OR^{10}$, or $OC(=O)R^{10}$ (with $R^{10}$ preferably being $C_1$-$C_3$ alkyl), more preferably OH. Where it occurs in formula (I) or other formulae in this specification, $R^6$ preferably is H. Where it occurs in formula (I) or other formulae elsewhere in this specification, $R^7$ preferably is OH, $OR^{10}$, or $OC(=O)R^{10}$ (with $R^{10}$ preferably being $C_1$-$C_3$ alkyl), more preferably OH. Where it occurs in formula (I) or in other formulae elsewhere in this specification, $R^9$ preferably is

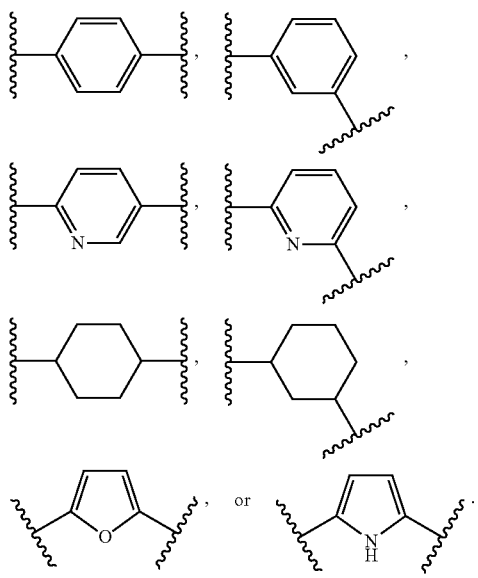

More preferably, $R^9$ is

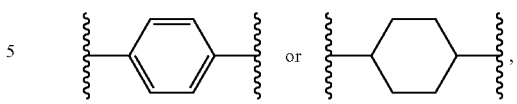

especially the former.

Where it occurs in formula (I) or in other formulae elsewhere in this specification, $R^{10}$ preferably is $C_1$-$C_6$ alkyl, cyclohexyl, cyclopentyl, phenyl, furanyl, or pyridyl. More preferably, $R^{10}$ is methyl, ethyl, propyl, or isopropyl.

Where it occurs in formulae (I), (Ia), (Ib) or other formulae elsewhere in this specification, $R^8$ preferably is the side chain residue of an α-amino acid selected from the group consisting of arginine, aspartic acid, citrulline, glutamic acid, glutamine, glycine, histidine, lysine, phenylalanine, serine, threonine, tryptophan, tyrosine, and valine. More preferably, $R^8$ is the side chain residue of glycine, lysine, citrulline, or serine. Preferably, the stereochemistry at the chiral carbon corresponds to that of a naturally occurring proteogenic α-amino acid, i.e. the L-isomer.

In a preferred embodiment of compounds having structures according to formulae (I), (Ia), and/or (Ib), the group $R^{1a}$ is selected from the group consisting of H, Me,

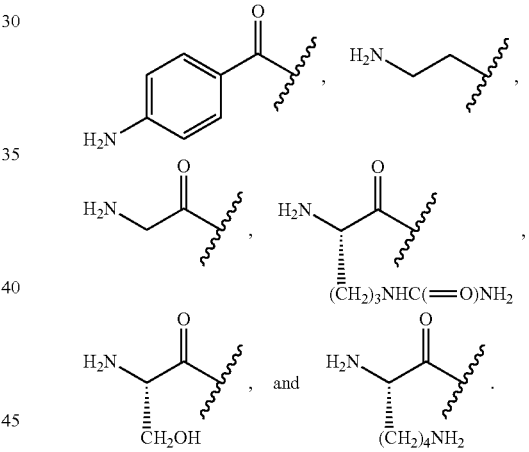

In a more preferred embodiment of compounds having structures according to formulae (I), (Ia), and/or (Ib), the group $R^{1a}$ is H,

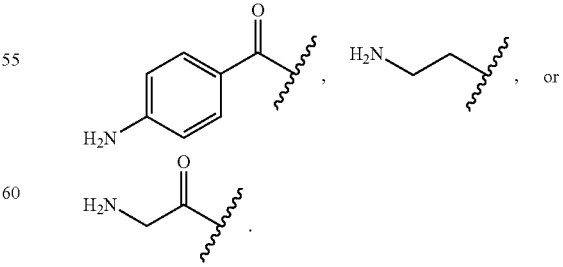

Specific compounds of this invention include those having structures according to formulae (IIa) through (IIh), or their pharmaceutically acceptable salts:

(IIa)
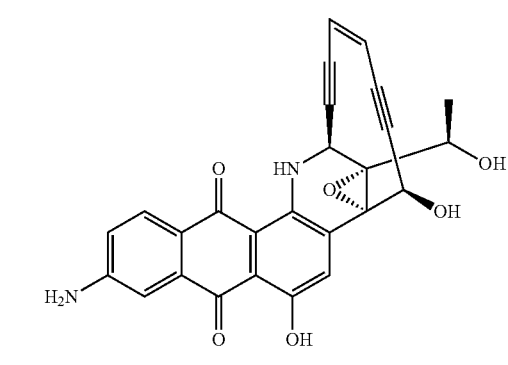
(IIb)
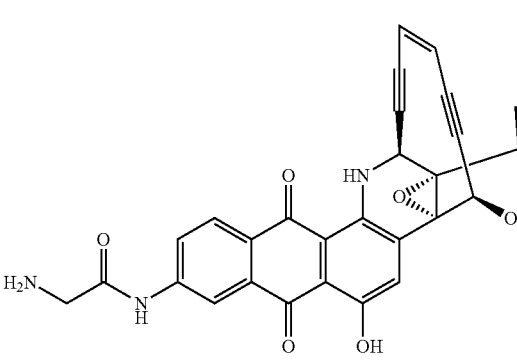
(IIc)
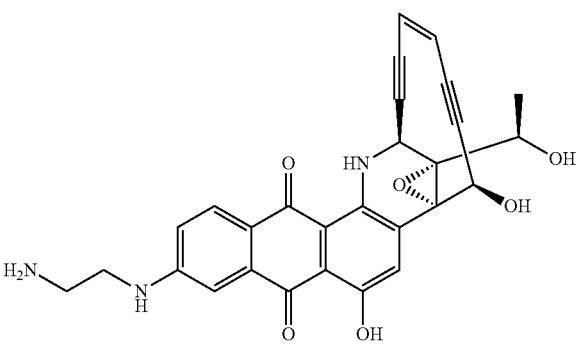
(IId)
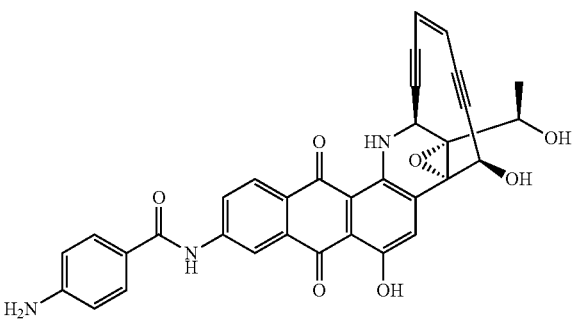
(IIe)
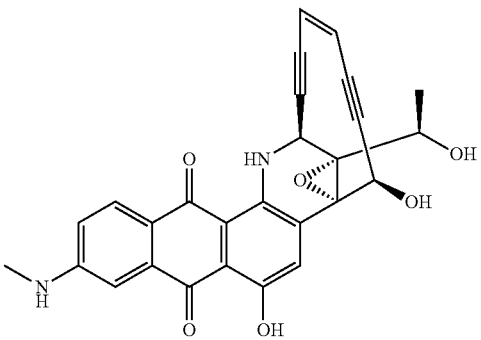
(IIf)
(IIg)
(IIh)
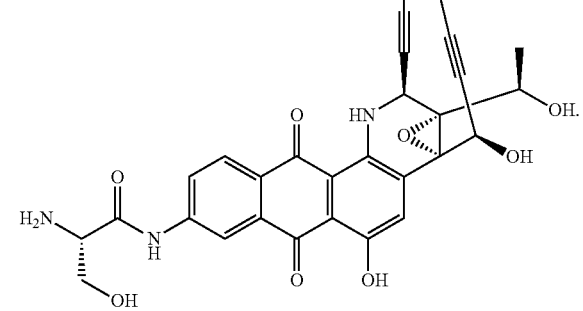

Conjugates

Another embodiment of this invention comprises a compound having a structure represented by formula (I), (Ia), (Ib), (IIa), (IIb), (IIc), (IId), (IIe), (IIg), or (IIh) is conjugated to a targeting moiety that specifically or preferentially binds to a chemical entity on a cancer cell. Preferably, the targeting moiety is an antibody or antigen binding portion thereof and the chemical entity is a tumor associated antigen. Preferably, the conjugation is effected through a chemical bond to the group $R^0$.

In another embodiment, there is provided a conjugate comprising cytotoxic compound according to this invention and a ligand, represented by formula (III)

$$[D(X^D)_a C(X^Z)_b]_m Z \qquad (III)$$

where Z is a ligand; D is a cytotoxic compound according to this invention (e.g., a compound according to formula (I), (Ia), or (Ib)); and —$(X^D)_a C(X^Z)_b$— are collectively referred to as a "linker moiety" or "linker" because they link Z and D. Within the linker, C is a cleavable group designed to be cleaved at or near the site of intended biological action of compound D; $X^D$ and $X^Z$ are referred to as spacer moieties (or "spacers") because they space apart D and C and C and Z, respectively; subscripts a and b are independently 0 or 1 (that is, the presence of $X^D$ and/or $X^Z$ are optional); and subscript m is 1, 2, 3, 4, 5, 6, 7, 8, 9, or 10 (preferably 1, 2, 3, or 4). D, $X^D$, C, $X^Z$ and Z are more fully described hereinbelow.

Ligand Z—for example an antibody—serves a targeting function. By binding to a target tissue or cell where its antigen or receptor is located, ligand Z directs the conjugate there. Preferably, the target tissue or cell is a cancer tissue or cell and the antigen or receptor is a tumor-associated antigen, that is, an antigen that is uniquely expressed by cancerous cells or is overexpressed by cancer cells, compared to non-cancerous cells. Cleavage of group C at the target tissue or cell releases compound D to exert its cytotoxic effect locally. In some instances, the conjugate is internalized into a target cell by endocytosis and cleavage takes place within the target cell. In this manner, precise delivery of compound D is achieved at the site of intended action, reducing the dosage needed. Also, compound D is normally biologically inactive (or significantly less active) in its conjugated state, thereby reducing undesired toxicity against non-target tissue or cells. As anticancer drugs are often highly toxic to cells in general, this is an important consideration.

As reflected by the subscript m, each molecule of ligand Z can conjugate with more than one compound D, depending on the number of sites ligand Z has available for conjugation and the experimental conditions employed. Those skilled in the art will appreciate that, while each individual molecule of ligand Z is conjugated to an integer number of compounds D, a preparation of the conjugate may analyze for a non-integer ratio of compounds D to ligand Z, reflecting a statistical average.

Ligand Z and Conjugation Thereof

Preferably, ligand Z is an antibody. For convenience and brevity and not of limitation, the detailed subsequent discussion herein about the conjugation of ligand Z is written in the context of its being an antibody, but those skilled in the art will understand that other types of ligand Z can be conjugated, mutatis mutandis. For example, conjugates with folic acid as the ligand can target cells having the folate receptor on their surfaces (Vlahov et al., *Bioorg. Med. Chem. Leu.* 2008, 18(16), 4558-4561; Leamon et al., *Cancer Res.* 2008, 68 (23), 9839-9844). For the same reason, the detailed discussion below is primarily written in terms of a 1:1 ratio of antibody Z to compound D.

Preferably, ligand Z is an antibody against a tumor associated antigen, allowing a conjugate comprising such a ligand Z to selectively target cancer cells. Examples of such antigens include: mesothelin, prostate specific membrane antigen (PSMA), CD19, CD22, CD30, CD70, CD200 (also known as OX-2), B7H4 (also known as O8E), protein tyrosine kinase 7 (PTK7), RG1, CTLA-4, and CD44. The antibody can be animal (e.g., murine), chimeric, humanized, or, preferably, human. The antibody preferably is monoclonal, especially a monoclonal human antibody. The preparation of human monoclonal antibodies against some of the aforementioned antigens is disclosed in Korman et al., US 2009/0074660 A1 (B7H4); Rao-Naik et al., US 2009/0142349 A1 A2 (CD19); King et al., US 2010/0143368 A1 (CD22); Keler et al., U.S. Pat. No. 7,387,776 B2 (2008) (CD30); Terrett et al., US 2009/0028872 A1 (CD70); Gorczynski et al., U.S. Pat. No. 7,238,352 B2 (2007) (CD200); Korman et al., U.S. Pat. No. 6,984,720 B1 (2006) (CTLA-4); Korman et al., U.S. Pat. No. 8,008,449 B2 (2011) (PD-1); Huang et al., US 2008/0279868 A1 (PSMA); Terrett et al., US 2010/0034826 A1 (PTK7); Harkins et al., U.S. Pat. No. 7,335,748 B2 (2008) (RG1); Terrett et al., WO 2009/045957 A1 (mesothelin); and Xu et al., US 2010/0092484 A1 (CD44); the disclosures of which are incorporated herein by reference.

Ligand Z can also be an antibody fragment or antibody mimetic, such as an affibody, a domain antibody (dAb), a nanobody, a unibody, a DARPin, an anticalin, a versabody, a duocalin, a lipocalin, or an avimer.

Any one of several different reactive groups on ligand Z can be a conjugation site, including ε-amino groups in lysine residues, pendant carbohydrate moieties, carboxylic acid groups, disulfide groups, and thiol groups. Each type of reactive group represents a trade-off, having some advantages and some disadvantages. For reviews on antibody reactive groups suitable for conjugation, see, e.g., Garnett, *Adv. Drug Delivery Rev.* 53 (2001), 171-216 and Dubowchik and Walker, *Pharmacology & Therapeutics* 83 (1999), 67-123, the disclosures of which are incorporated herein by reference.

In one embodiment, ligand Z is conjugated via a lysine ε-amino group. Most antibodies have multiple exposed lysine ε-amino groups, which can be conjugated via amide, urea, thiourea, or carbamate bonds using techniques known in the art, including modification with a heterobifunctional agent (as further described hereinbelow). However, it is difficult to control which and how many ε-amino groups react, leading to potential batch-to-batch variability in conjugate preparations. Also, conjugation may cause neutralization of a protonated ε-amino group important for maintaining the antibody's native conformation or may take place at a lysine near or at the antigen binding site, neither being a desirable occurrence.

In another embodiment, ligand Z can be conjugated via a carbohydrate side chain, as many antibodies are glycosylated. The carbohydrate side chain can be oxidized with periodate to generate aldehyde groups, which in turn can be reacted with amines to form an imine group, such as in a semicarbazone, oxime, or hydrazone. If desired, the imine group can be converted to a more stable amine group by reduction with sodium cyanoborohydride. For additional disclosures on conjugation via carbohydrate side chains, see, e.g., Rodwell et al., *Proc. Nat'l Acad. Sci. USA* 83, 2632-2636 (1986); the disclosure of which is incorporated herein by reference. As with lysine ε-amino groups, there are concerns regarding reproducibility of the location of the conjugation site(s) and stoichiometry.

In yet another embodiment, ligand Z can be conjugated via a carboxylic acid group. In one embodiment, a terminal carboxylic acid group is functionalized to generate a carbohydrazide, which is then reacted with an aldehyde-bearing conjugation moiety. See Fisch et al., *Bioconjugate Chemistry* 1992, 3, 147-153.

In yet another embodiment, antibody Z can be conjugated via a disulfide group bridging a cysteine residue on antibody Z and a sulfur on the other portion of the conjugate. Some antibodies lack free thiol (sulfhydryl) groups but have disulfide groups, for example in the hinge region. In such case, free thiol groups can be generated by reduction of native disulfide groups. The thiol groups so generated can then be used for conjugation. See, e.g., Packard et al., *Biochemistry* 1986, 25, 3548-3552; King et al., *Cancer Res.* 54, 6176-6185 (1994); and Doronina et al., *Nature Biotechnol.* 21(7), 778-784 (2003); the disclosures of which are incorporated herein by reference. Again, there are concerns regarding conjugation site location and stoichiometry and the possible disruption of antibody native conformation.

A number of methods are known for introducing free thiol groups into antibodies without breaking native disulfide bonds, which methods can be practiced with a ligand Z of this invention. Depending on the method employed, it may be possible to introduce a predictable number of free sulfhydryls at predetermined locations. In one approach, mutated antibodies are prepared in which a cysteine is substituted for another amino acid. See, for example, Eigenbrot et al., U.S. Pat. No. 7,521,541 B2 (2009); Chilkoti et al., *Bioconjugate Chem.* 1994, 5, 504-507; Urnovitz et al., U.S. Pat. No. 4,698, 420 (1987); Stimmel et al., *J. Biol. Chem.*, 275 (39), 30445-30450 (2000); Bam et al., U.S. Pat. No. 7,311,902 B2 (2007); Kuan et al., *J. Biol. Chem.*, 269 (10), 7610-7618 (1994); Poon et al., *J. Biol. Chem.*, 270 (15), 8571-8577 (1995). In another approach, an extra cysteine is added to the C-terminus See, e.g. Cumber et al., *J. Immunol.*, 149, 120-126 (1992); King et al., *Cancer Res.*, 54, 6176-6185 (1994); Li et al., *Bioconjugate Chem.*, 13, 985-995 (2002); Yang et al., *Protein Engineering*, 16, 761-770 (2003); and Olafson et al., *Protein Engineering Design & Selection*, 17, 21-27 (2004). A preferred method for introducing free cysteines is that taught by Liu et al., WO 2009/026274 A1, in which a cysteine bearing amino acid sequence is added to the C-terminus of the heavy chain of an antibody. This method introduces a known number of cysteine residues (one per heavy chain) at a known location remote from the antigen binding site. The disclosures of the documents cited in this paragraph are all incorporated herein by reference.

In yet another embodiment, lysine ε-amino groups can be modified with heterobifunctional reagents such as 2-iminothiolane or N-succinimidyl-3-(2-pyridyldithio)-propionate (SPDP), converting an ε-amino group into a thiol or disulfide group—creating a cysteine surrogate, as it were. However, this method suffers from the same conjugation location and stoichiometry limitations associated with ε-amino groups proper.

In yet another preferred embodiment, ligand Z is conjugated via the nucleophilic addition product of a thiol group to an acceptor moiety. A preferred acceptor moiety is a maleimide group, whose reaction with an antibody thiol group is generically illustrated below. The thiol group can be a native one, or one introduced as described above.

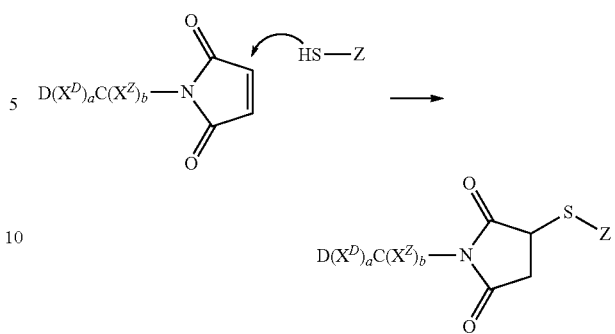

Ligand Z can also be conjugated via a functional group adapted for use with "click" chemistry, as discussed hereinbelow.

Linker—$(X^D)_aC(X^Z)_b$—

As noted above, the linker portion of a conjugate of this invention comprises up to three elements: a cleavable group C and optional spacers $X^Z$ and $X^D$.

Cleavable group C is a group cleavable under physiological conditions, preferably selected such that it is relatively stable while the conjugate is in general circulation in the blood plasma, but is readily cleaved once the conjugate reaches its site of intended action, that is, near, at, or within the target cell. Preferably, the conjugate is internalized by endocytosis by a target cell upon binding of antibody Z to an antigen displayed on the surface of the target cell. Subsequently, cleavage of group C occurs in a vesicular body of the target cell (an early endosome, a late endosome, or, especially, a lysosome).

In one embodiment, group C is a pH sensitive group. The pH in blood plasma is slightly above neutral, while the pH inside a lysosome is acidic, circa 5. Thus, a group C whose cleavage is acid catalyzed will cleave at a rate several orders of magnitude faster inside a lysosome than in the blood plasma rate. Examples of suitable acid-sensitive groups include cis-aconityl amides and hydrazones, as described in Shen et al., U.S. Pat. No. 4,631,190 (1986); Shen et al., U.S. Pat. No. 5,144,011 (1992); Shen et al., *Biochem. Biophys. Res. Commun.* 102, 1048-1054 (1981) and Yang et al., *Proc. Natl Acad. Sci* (USA), 85, 1189-1193 (1988); the disclosures of which are incorporated herein by reference.

In another embodiment, group C is a disulfide. Disulfides can be cleaved by a thiol-disulfide exchange mechanism, at a rate dependent on the ambient thiol concentration. As the intracellular concentration of glutathione and other thiols is higher than their serum concentrations, the cleavage rate of a disulfide will be higher intracellularly. Further, the rate of thiol-disulfide exchange can be modulated by adjustment of the steric and electronic characteristics of the disulfide (e.g., an alkyl-aryl disulfide versus an alkyl-alkyl disulfide; substitution on the aryl ring, etc.), enabling the design of disulfide linkages that have enhanced serum stability or a particular cleavage rate. For additional disclosures relating to disulfide cleavable groups in conjugates, see, e.g., Thorpe et al., *Cancer Res.* 48, 6396-6403 (1988); Santi et al., U.S. Pat. No. 7,541,530 B2 (2009); Ng et al., U.S. Pat. No. 6,989,452 B2 (2006); Ng et al., WO 2002/096910 A1; Boyd et al., U.S. Pat. No. 7,691,962 B2; and Sufi et al., US 2010/0145036 A1; the disclosures of which are incorporated herein by reference.

A preferred group C comprises a peptide bond that is cleaved, preferentially by a protease at the intended site of action, as opposed to by a protease in the serum. Typically, group C comprises from 1 to 20 amino acids, preferably from 1 to 6 amino acids, more preferably from 1 to 3 amino acids. The amino acid(s) can be natural and/or unnatural α-amino acids. Natural amino acids are those encoded by the genetic code, as well as amino acids derived therefrom, e.g., hydroxyproline, γ-carboxyglutamate, citrulline, and O-phosphoserine. The term amino acid also includes amino acid analogs and mimetics. Analogs are compounds having the same general $H_2N(R)CHCO_2H$ structure of a natural amino acid, except that the R group is not one found among the natural amino acids. Examples of analogs include homoserine, norleucine, methionine-sulfoxide, and methionine methyl sulfonium. An amino acid mimetic is a compound that has a structure different from the general chemical structure of an α-amino acid but functions in a manner similar to one. The term "unnatural amino acid" is intended to represent the "D" stereochemical form, the natural amino acids being of the "L" form.

Preferably, group C contains an amino acid sequence that is a cleavage recognition sequence for a protease. Many cleavage recognition sequences are known in the art. See, e.g., Matayoshi et al. *Science* 247: 954 (1990); Dunn et al. *Meth. Enzymol.* 241: 254 (1994); Seidah et al. *Meth. Enzymol.* 244: 175 (1994); Thornberry, *Meth. Enzymol.* 244: 615 (1994); Weber et al. *Meth. Enzymol.* 244: 595 (1994); Smith et al. *Meth. Enzymol.* 244: 412 (1994); and Bouvier et al. *Meth. Enzymol.* 248: 614 (1995); the disclosures of which are incorporated herein by reference.

For conjugates that are not intended to be internalized by a cell, a group C can be chosen such that it is cleaved by a protease present in the extracellular matrix in the vicinity of the target tissue, e.g., a protease released by nearby dying cells or a tumor-associated protease. Exemplary extracellular tumor-associated proteases are matrix metalloproteases (MMP), thimet oligopeptidase (TOP) and CD10.

For conjugates that are designed to be internalized by a cell, group C preferably comprises an amino acid sequence selected for cleavage by an endosomal or lysosomal protease, especially the latter. Non-limiting examples of such proteases include cathepsins B, C, D, H, L and S, especially cathepsin B. Cathepsin B preferentially cleaves peptides at a sequence -$AA^2$-$AA^1$- where $AA^1$ is a basic or strongly hydrogen bonding amino acid (such as lysine, arginine, or citrulline) and $AA^2$ is a hydrophobic amino acid (such as phenylalanine, valine, alanine, leucine, or isoleucine), for example Val-Cit (where Cit denotes citrulline) or Val-Lys. (Herein, amino acid sequences are written in the N-to-C direction, as in $H_2N$-$AA^2$-$AA^1$-$CO_2H$, unless the context clearly indicates otherwise.) For additional information regarding cathepsin-cleavable groups, see Dubowchik et al., *Biorg. Med. Chem. Lett.* 8, 3341-3346 (1998); Dubowchik et al., *Bioorg. Med. Chem. Lett.,* 8 3347-3352 (1998); and Dubowchik et al., *Bioconjugate Chem.* 13, 855-869 (2002); the disclosures of which are incorporated by reference. Another enzyme that can be utilized for cleaving peptidyl linkers is legumain, a lysosomal cysteine protease that preferentially cleaves at Ala-Ala-Asn.

In one embodiment, Group C is a peptide comprising the two-amino acid sequence -$AA^2$-$AA^1$- wherein $AA^1$ is lysine, arginine, or citrulline and $AA^2$ is phenylalanine, valine, alanine, leucine or isoleucine. In another embodiment, C consists of a sequence of one to five amino acids, selected from the group consisting of Val-Cit, Ala-Val, Val-Ala-Val, Lys-Lys, Ala-Asn-Val, Val-Leu-Lys, Cit-Cit, Val-Lys, Ala-Ala-Asn, Lys, Cit, Ser, and Glu.

The preparation and design of cleavable groups C consisting of a single amino acid is disclosed in Chen et al., US 2010/0113476 A1, the disclosure of which is incorporated herein by reference.

Group C can also be a photocleavable one, for example a nitrobenzyl ether that is cleaved upon exposure to light.

Group C can be bonded directly to antibody Z or compound D; that is, spacers $X^Z$ and $X^D$, as the case may be, can be absent. For example, if group C is a disulfide, one of the two sulfurs can be a cysteine residue or its surrogate on antibody Z. Or, group C can be a hydrazone bonded to an aldehyde on a carbohydrate side chain of the antibody. Or, group C can be a peptide bond formed with a lysine ε-amino group of antibody Z. In a preferred embodiment, compound D is directly bonded to group C via a peptidyl bond to a carboxyl or amine group in compound D.

When present, spacer $X^Z$ provides spatial separation between group C and antibody Z, lest the former sterically interfere with antigen binding by latter or the latter sterically interfere with cleavage of the former. Further, spacer $X^Z$ can be used to confer increased solubility or decreased aggregation properties to conjugates. A spacer $X^Z$ can comprise one or more modular segments, which can be assembled in any number of combinations. Examples of suitable segments for a spacer $X^Z$ are:

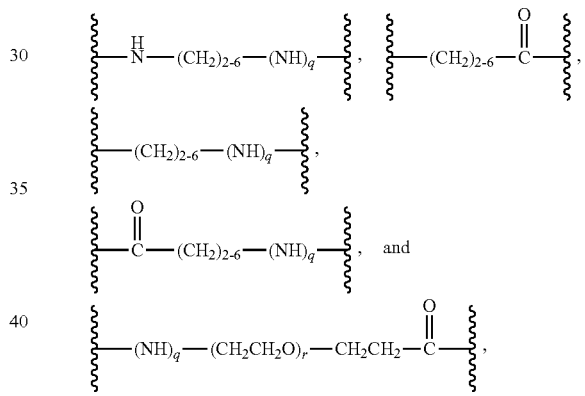

where the subscript q is 0 or 1 and the subscript r is 1 to 24, preferably 2 to 4. These segments can be combined, such as shown below:

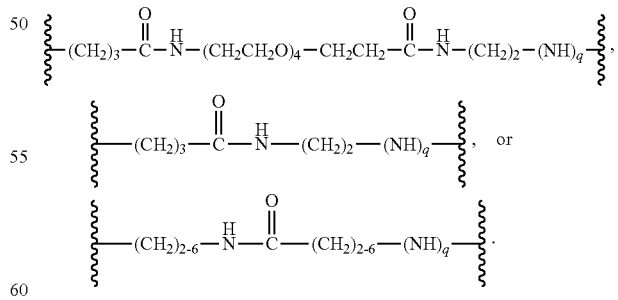

Spacer $X^D$, if present, provides spatial separation between group C and compound D, lest the latter interfere sterically or electronically with cleavage of the former. Spacer $X^D$ also can serve to introduce additional molecular mass and chemical functionality into a conjugate. Generally, the additional mass and functionality will affect the serum half-life and other properties of the conjugate. Thus, through judicious selection of spacer groups, the serum half-live of a conjugate can be modulated. Spacer $X^D$ also can be assembled from modular segments, as described above in the context of spacer $X^Z$.

Spacers $X^Z$ and/or $X^D$, where present, preferably provide a linear separation of from 5 to 15 atoms, more preferably from 5 to 20 atoms, between Z and C or D and C, respectively.

Either spacer $X^Z$ or $X^D$, or both, can comprise a self-immolating moiety. A self-immolating moiety is a moiety that (1) is bonded to group C and either antibody Z or cytotoxin D and (2) has a structure such that cleavage from group C initiates a reaction sequence resulting in the self-immolating moiety disbonding itself from antibody Z or cytotoxin D, as the case may be. In other words, reaction at a site distal from antibody Z or cytotoxin D (cleavage from group C) causes the $X^Z$—Z or the $X^D$-D bond to rupture as well. The presence of a self-immolating moiety is desirable in the case of spacer $X^D$ because, if, after cleavage of the conjugate, spacer $X^D$ or a portion thereof were to remain attached to cytotoxin D, the biological activity of the latter may be impaired. The use of a self-immolating moiety is especially desirable where cleavable group C is a polypeptide.

Exemplary self-immolating moieties (i)-(v) bonded to a hydroxyl or amino group on a partner molecule D are shown below:

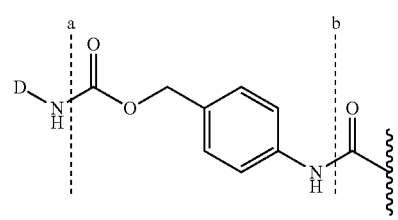

(i)

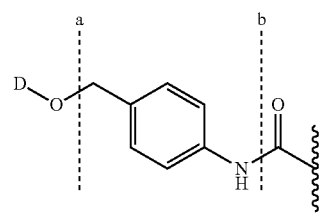

(ii)

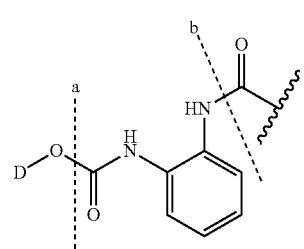

(iii)

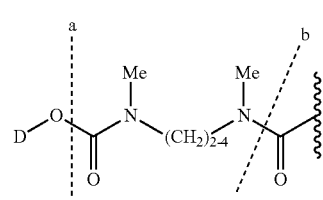

(iv)

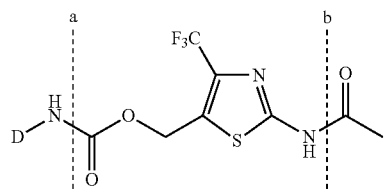

(v)

The self-immolating moiety is the structure between dotted lines a and b, with adjacent structural features shown to provide context. Self-immolating moieties (i) and (v) are bonded to a compound D-NH$_2$ (i.e., compound D is conjugated via an amino group), while self-immolating moieties (ii), (iii), and (iv) are bonded to a compound D-OH (i.e., compound D is conjugated via a hydroxyl or carboxyl group). Cleavage of the amide bond at dotted line b releases the amide nitrogen as an amine nitrogen, initiating a reaction sequence that results in the cleavage of the bond at dotted line a and the consequent release of D-OH or D-NH$_2$, as the case may be. For additional disclosures regarding self-immolating moieties, see Carl et al., *J. Med. Chem.*, 24 (3), 479-480 (1981); Carl et al., WO 81/01145 (1981); Dubowchik et al., *Pharmacology & Therapeutics*, 83, 67-123 (1999); Firestone et al., U.S. Pat. No. 6,214,345 B1 (2001); Toki et al., *J. Org. Chem.* 67, 1866-1872 (2002); Doronina et al., *Nature Biotechnology* 21 (7), 778-784 (2003) (erratum, p. 941); Boyd et al., U.S. Pat. No. 7,691,962 B2; Boyd et al., US 2008/0279868 A1; Sufi et al., WO 2008/083312 A2; Feng, U.S. Pat. No. 7,375,078 B2; and Senter et al., US 2003/0096743 A1; the disclosures of which are incorporated by reference.

In another embodiment, an antibody targeting moiety and the cytotoxic compound D are linked by a non-cleavable linker. Degradation of the antibody eventually reduces the linker to a small appended moiety that does not interfere with the biological activity of cytotoxic compound D.

Compound D—Linker Compositions

In the compounds of this invention conjugation is preferably effected through a bond to a group $R^0$ as defined in formula (I). Preferably, $R^0$ is $NHR^{1a}$. Where $R^{1a}$ is H or alkyl, the bond may be to the nitrogen of $R^{1a}NH$. Where $R^{1a}$ is $(CH_2)_nNH_2$, $C(=O)(CH_2)_nNH_2$, $C(=O)CHR^8NH_2$, or $C(=O)R^9NH_2$, conjugation can be effected via the amino ($NH_2$) group of $R^{1a}$. Thus, depending on the structure of $R^{1a}NH$, D may be represented as:

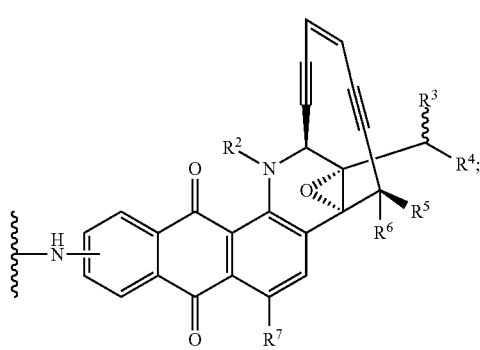

-continued

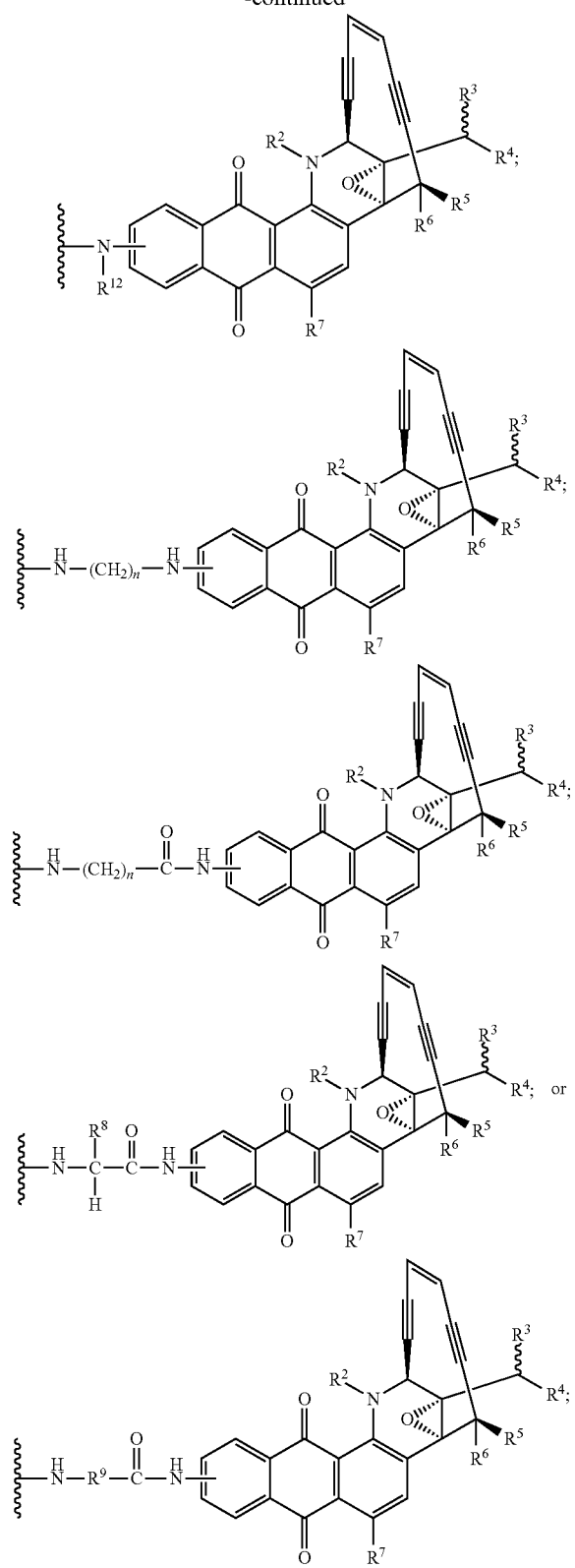

wherein $R^{12}$ is $C_1$-$C_6$ alkyl and $R^2$, $R^3$, $R^4$, $R^5$, $R^6$, $R^7$, $R^8$, $R^9$, and n are as defined in respect of formula (I).

Corresponding structures can be derived from formulae (Ia), (Ib), or (IIa) through (IIh), mutatis mutandis.

Preferably, D is

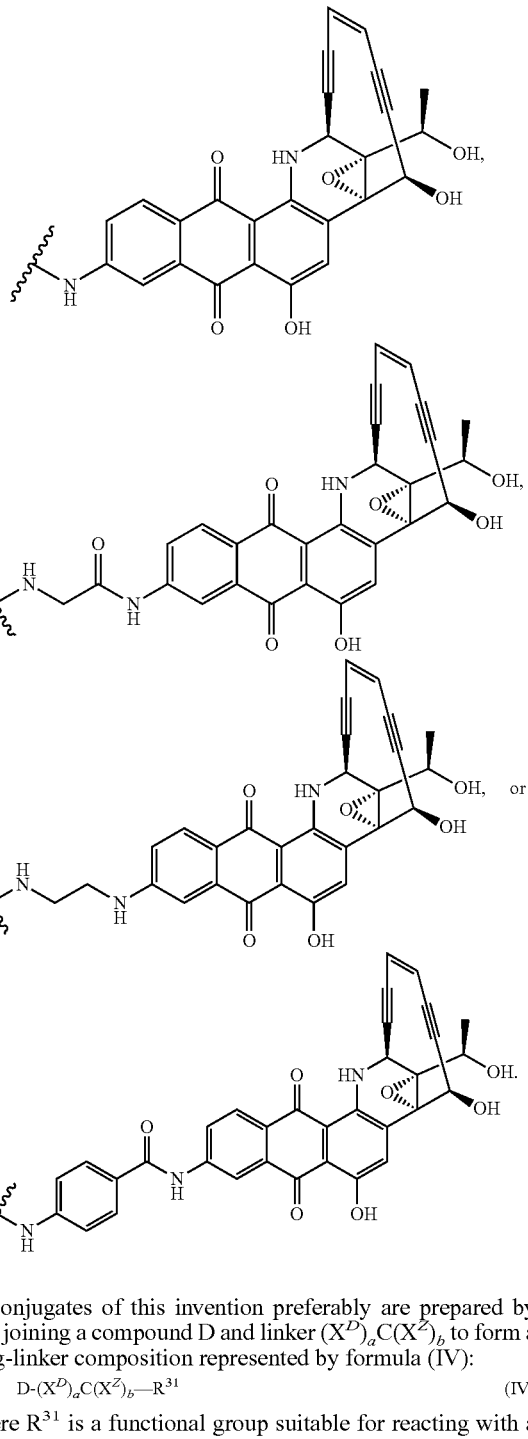

Conjugates of this invention preferably are prepared by first joining a compound D and linker $(X^D)_a C(X^Z)_b$ to form a drug-linker composition represented by formula (IV):

$$D\text{-}(X^D)_a C(X^Z)_b\text{—}R^{31} \qquad (IV)$$

where $R^{31}$ is a functional group suitable for reacting with a functional group on antibody Z to form the conjugate. Examples of suitable groups $R^{31}$ include azide, cyclooctyne,

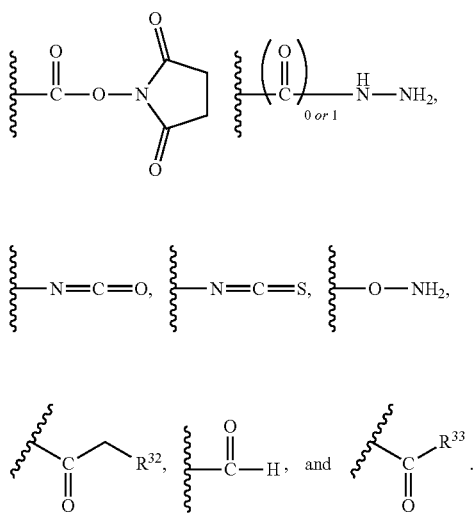

where $R^{32}$ is Cl, Br, F, mesylate, or tosylate and $R^{33}$ is Cl, Br, I, F, OH, —O—N-succinimidyl, —O-(4-nitrophenyl), —O-pentafluorophenyl, or —O-tetrafluorophenyl. Chemistry generally usable for the preparation of suitable moieties $D\text{-}(X^D)_a C(X^Z)_b\text{---}R^{31}$ is disclosed in Ng et al., U.S. Pat. No. 7,087,600 B2 (2006); Ng et al., U.S. Pat. No. 6,989,452 B2 (2006); Ng et al., U.S. Pat. No. 7,129,261 B2 (2006); Ng et al., WO 02/096910 A1; Boyd et al., U.S. Pat. No. 7,691,962 B2; Chen et al., U.S. Pat. No. 7,517,903 B2 (2009); Gangwar et al., U.S. Pat. No. 7,714,016 B2 (2010); Boyd et al., US 2008/0279868 A1; Gangwar et al., U.S. Pat. No. 7,847,105 B2 (2010); Gangwar et al., U.S. Pat. No. 7,968,586 B2 (2011); Sufi et al., US 2010/0145036 A1; and Chen et al., US 2010/0113476 A1; the disclosures of which are incorporated herein by reference.

Preferably reactive functional group —$R^{31}$ is —$NH_2$, —OH, —$CO_2H$, —SH, maleimido, cyclooctyne, azido (—$N_3$), hydroxylamino (—$ONH_2$) or N-hydroxysuccinimido.

An —OH group can be esterified with a carboxy group on the antibody, for example, on an aspartic or glutamic acid side chain.

A —$CO_2H$ group can be esterified with a —OH group or amidated with an amino group (for example on a lysine side chain) on the antibody.

An N-hydroxysuccinimide group is functionally an activated carboxyl group and can conveniently be amidated by reaction with an amino group (e.g., from lysine).

A maleimide group can be conjugated with an —SH group on the antibody (e.g., from cysteine or from the chemical modification of the antibody to introduce a sulfhydryl functionality), in a Michael addition reaction.

An —SH group is particularly useful for conjugation where the antibody has been modified to introduce a maleimide group thereto, in a Michael addition reaction that is the "mirror image" of that described above. Antibodies can be modified to have maleimide groups with N-succinimidyl 4-(maleimidomethyl)-cyclohexanecarboxylate (SMCC) or its sulfonated variant sulfo-SMCC, both reagents being available from Sigma-Aldrich.

Azide and cyclooctyne are complementary functional groups that can effect conjugation via so-called copper-free "click chemistry," in which the azide adds across the strained alkyne bond of the cyclooctyne to form an 1,2,3-triazole ring. See, e.g., Agard et al., J. Amer. Chem. Soc. 2004, 126, 15046-15047; Best, Biochemistry 2009, 48, 6571-6584. The azide can be the reactive functional group $R^{31}$ in formula (IV) and the cyclooctyne can be situated on the antibody or antigen binding portion thereof, or vice-versa. A cyclooctyne group can be provided by a DIBO reagent (available from Invitrogen/Molecular Probes, Eugene, Oreg.).

Techniques for introducing non-natural amino acids into antibodies can be utilized, with the non-natural amino acid providing a functionality for conjugation with the reactive functional group. For instance, the non-natural amino acid p-acetylphenylalanine can be incorporated into an antibody, as taught in Tian et al., WO 2008/030612 A2 (2008). The ketone group in p-acetylphenyalanine can be a conjugation site by the formation of an oxime with a hydroxylamino reactive functional group.

An amine ($NH_2$) group can be used for conjugation using the enzyme transglutaminase, as taught in Jeger et al., Angew. Chem. Int. Ed. 2010, 49, 9995-9997.

Conjugation can also be effected using the enzyme Sortase A, as taught in Levary et al., PLoS One 2011, 6(4), e18342; Proft, Biotechnol. Lett. 2010, 32, 1-10; Ploegh et al., WO 2010/087994 A2 (2010); and Mao et al., WO 2005/051976 A2 (2005). The Sortase A recognition motif (typically LPXTG, where X is any natural amino acid) may be located on the ligand Z and the nucleophilic acceptor motif (typically GGG) may be the group $R^{31}$ in formula (IV), or vice-versa.

Examples of compositions according to formula (IV) include those having structures represented by formulae (IVa)-(IVg):

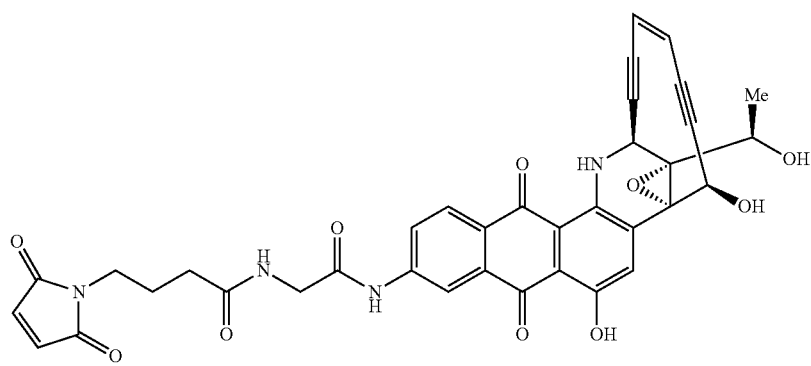

(IVa)

-continued
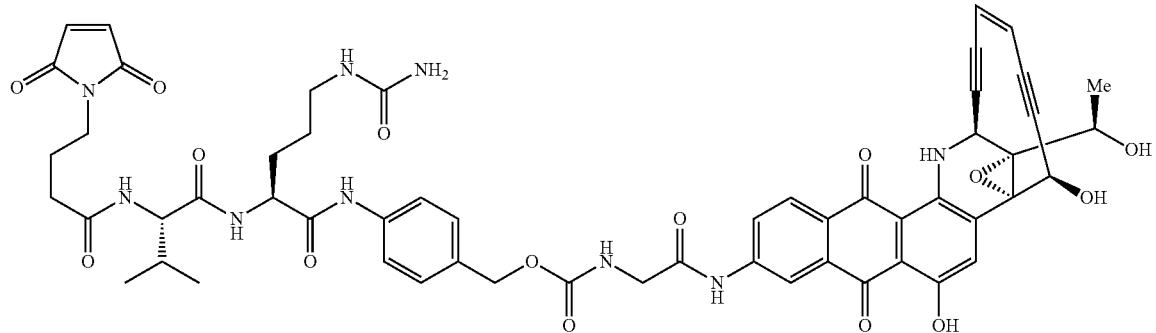
(IVb)
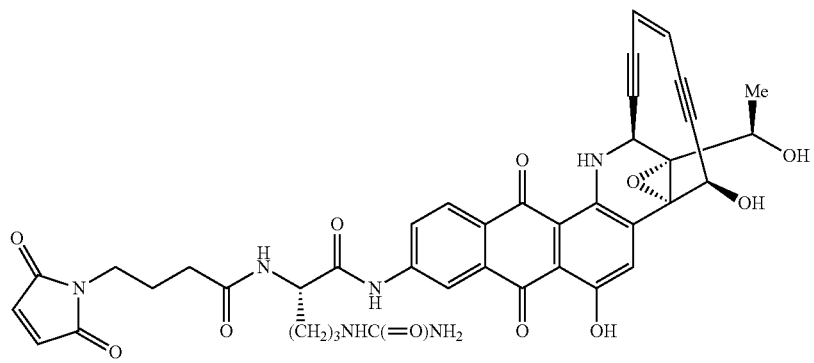
(IVc)
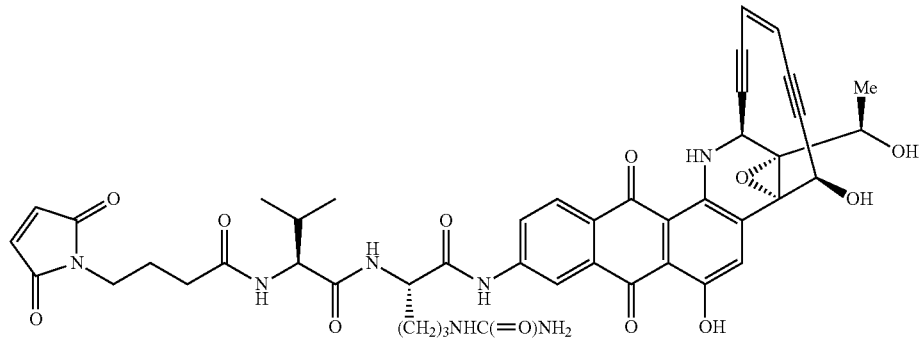
(IVd)
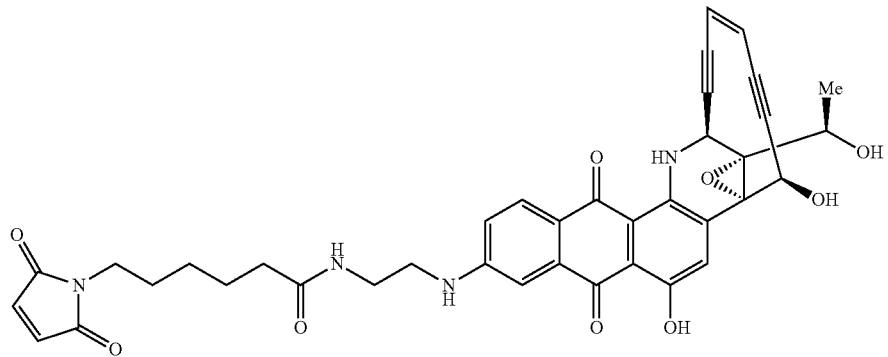
(IVe)

(IVf)

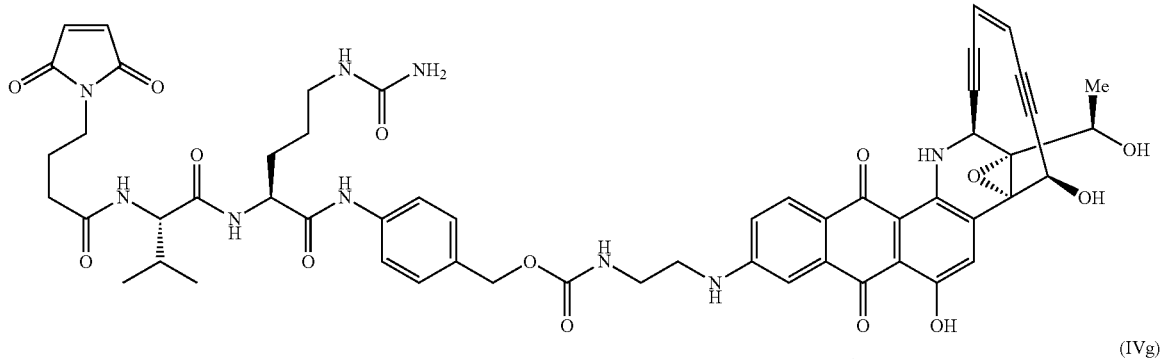

(IVg)

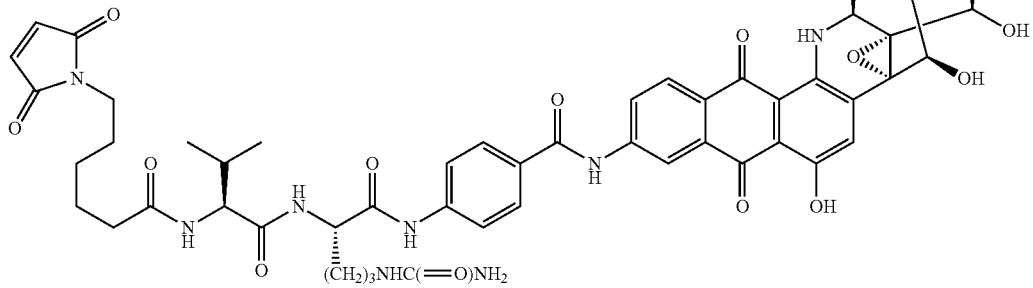

Preparation of Conjugates

The following is an illustrative procedure, based on introduction of free thiol groups into an antibody by reaction of lysine ε-amino groups with 2-iminothiolane, followed by reaction with a maleimide-containing drug-linker moiety such as described above. Initially the antibody is buffer exchanged into 0.1 M phosphate buffer (pH 8.0) containing 50 mM NaCl and 2 mM diethylene triamine pentaacetic acid (DTPA) and concentrated to 5-10 mg/mL. Thiolation is achieved through addition of 2-iminothiolane to the antibody. The amount of 2-iminothiolane to be added can be determined by a preliminary experiment and varies from antibody to antibody. In the preliminary experiment, a titration of increasing amounts of 2-iminothiolane is added to the antibody, and following incubation with the antibody for 1 h at RT (room temperature, circa 25° C.), the antibody is desalted into 50 mM pH 6.0 HEPES buffer using a SEPHADEX™ G-25 column and the number of thiol groups introduced determined rapidly by reaction with dithiodipyridine (DTDP). Reaction of thiol groups with DTDP results in liberation of thiopyridine, which can be monitored spectroscopically at 324 nm. Samples at a protein concentration of 0.5-1.0 mg/mL are typically used. The absorbance at 280 nm can be used to accurately determine the concentration of protein in the samples, and then an aliquot of each sample (0.9 mL) is incubated with 0.1 mL DTDP (5 mM stock solution in ethanol) for 10 min at RT. Blank samples of buffer alone plus DTDP are also incubated alongside. After 10 min, absorbance at 324 nm is measured and the number of thiol groups is quantitated using an extinction coefficient for thiopyridine of 19,800 $M^{-1}$.

Typically a thiolation level of about three thiol groups per antibody is desirable. For example, with some antibodies this can be achieved by adding a 15-fold molar excess of 2-iminothiolane followed by incubation at RT for 1 h. The antibody is then incubated with 2-iminothiolane at the desired molar ratio and then desalted into conjugation buffer (50 mM pH 6.0 HEPES buffer containing 5 mM glycine and 2 mM DTPA). The thiolated material is maintained on ice while the number of thiols introduced is quantitated as described above.

After verification of the number of thiols introduced, the drug-linker moiety is added at a 3-fold molar excess per thiol. The conjugation reaction is allowed to proceed in conjugation buffer also containing a final concentration of 5% dimethylsulfoxide (DMSO), or similar alternative solvent. Commonly, the drug-linker stock solution is dissolved in 100% DMSO. The stock solution is added directly to the thiolated antibody, which has enough DMSO added to bring the final concentration to 10%, or pre-diluted in conjugation buffer containing a final concentration of 10% DMSO, followed by addition to an equal volume of thiolated antibody.

The conjugation reaction mixture is incubated at RT for 2 h with stirring. Following incubation, the conjugation reaction mixture is centrifuged and filtered through a 0.2 μm filter. Purification of the conjugate can be achieved through chromatography using a number of methods. In one method, the conjugate is purified using size-exclusion chromatography on a SEPHACRYL™ S200 column pre-equilibrated with 50 mM pH 7.2 HEPES buffer containing 5 mM glycine and 50 mM NaCl. Chromatography is carried out at a linear flow rate of 28 cm/h. Fractions containing conjugate are collected, pooled and concentrated. In an alternative method, purification can be achieved through ion-exchange chromatography. Conditions vary from antibody to antibody and should to be optimized in each case. For example, antibody-drug conjugate reaction mix is applied to an SP-SEPHAROSE™ column pre-equilibrated in 50 mM pH 5.5 HEPES containing 5 mM glycine. The antibody conjugate is eluted using a gradient of 0-1 M NaCl in equilibration buffer at pH 5.5. Relevant fractions containing the conjugate are pooled and dialyzed against formulation buffer (50 mM pH 7.2 HEPES buffer containing 5 mM glycine and 100 mM NaCl).

Those skilled in the art will understand that the above-described conditions and methodology are exemplary and non-limiting and that other approaches for conjugation are known in the art and usable in the present invention.

Structures of some preferred conjugates according to this invention are shown by formulae (Va) through (Vg), where Ab represents an antibody and m is 1, 2, 3, or 4:

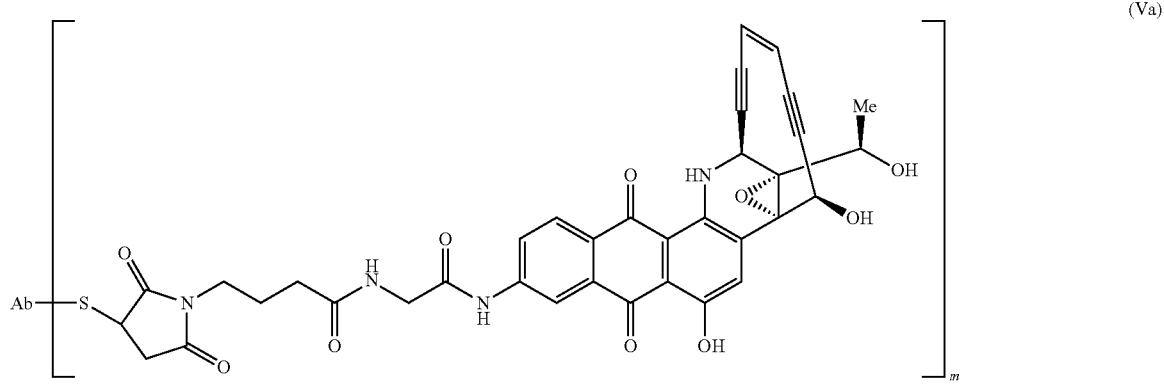

(Va)

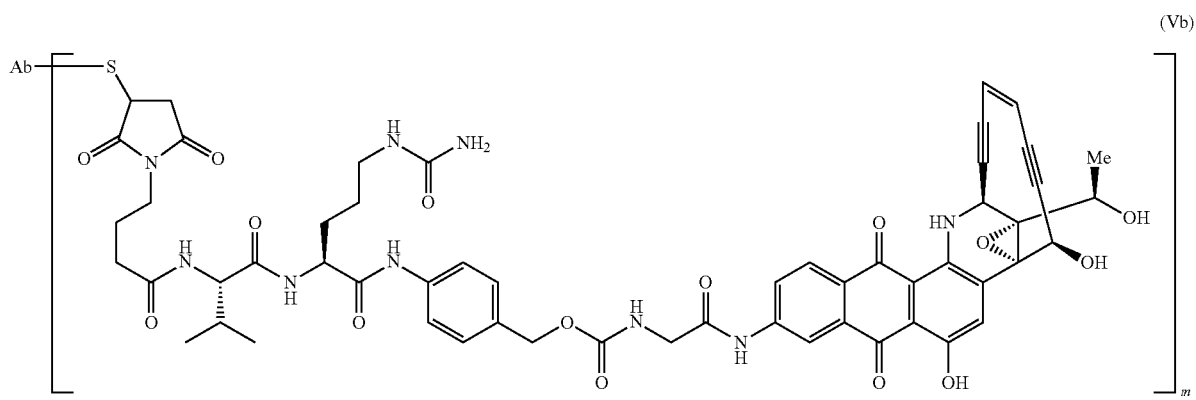

(Vb)

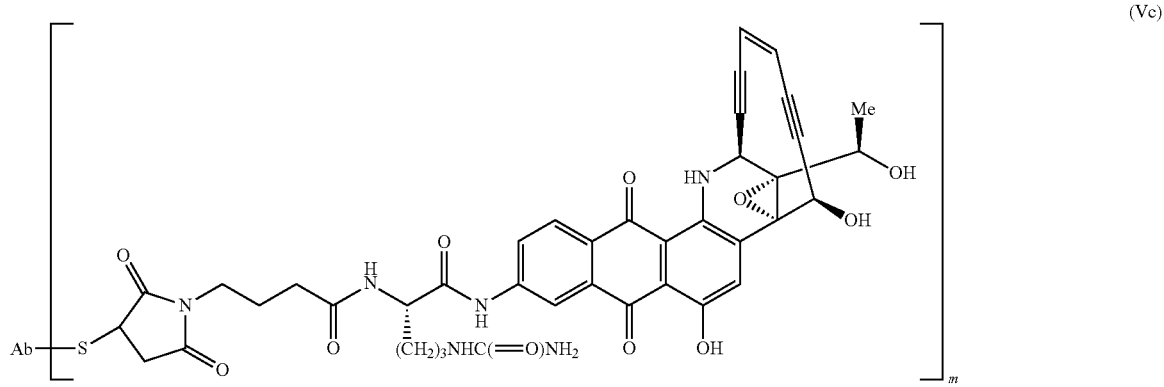

(Vc)

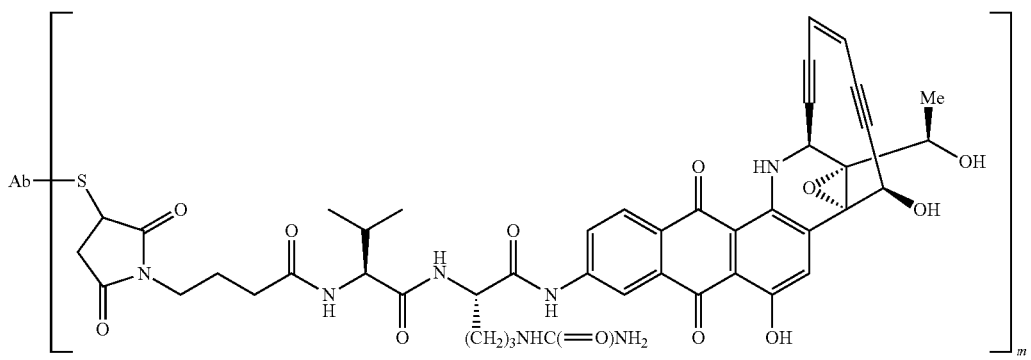
(Vd)
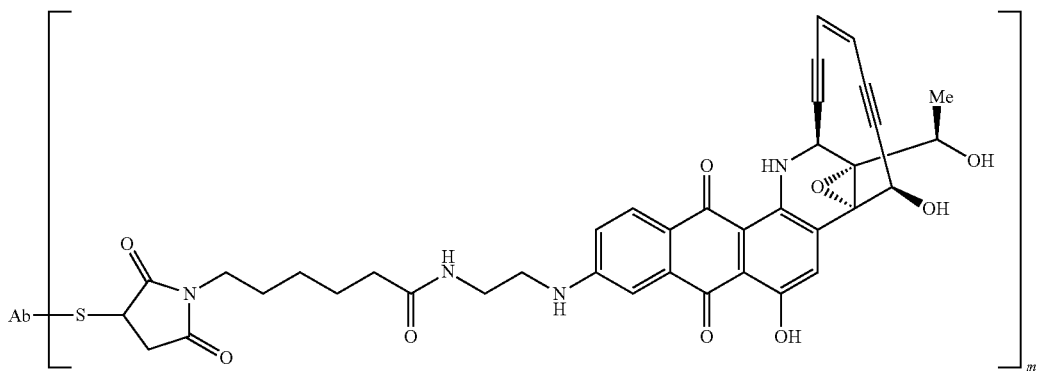
(Ve)
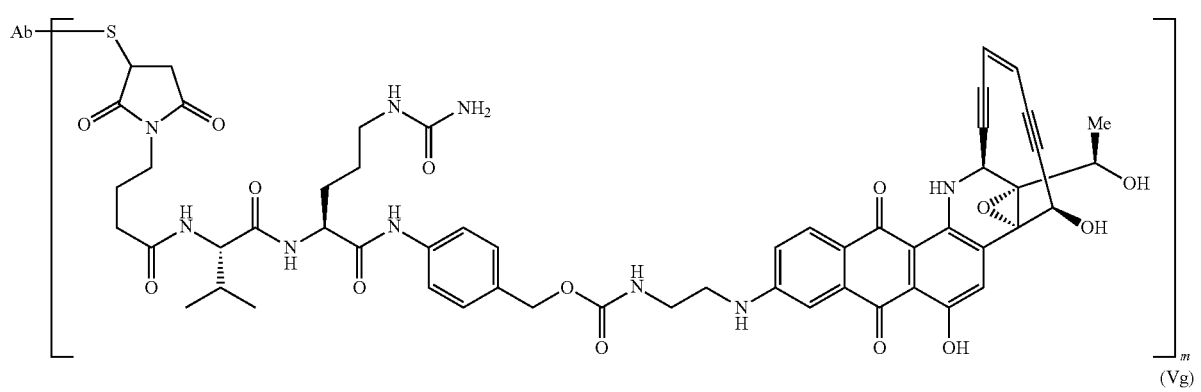
(Vf)
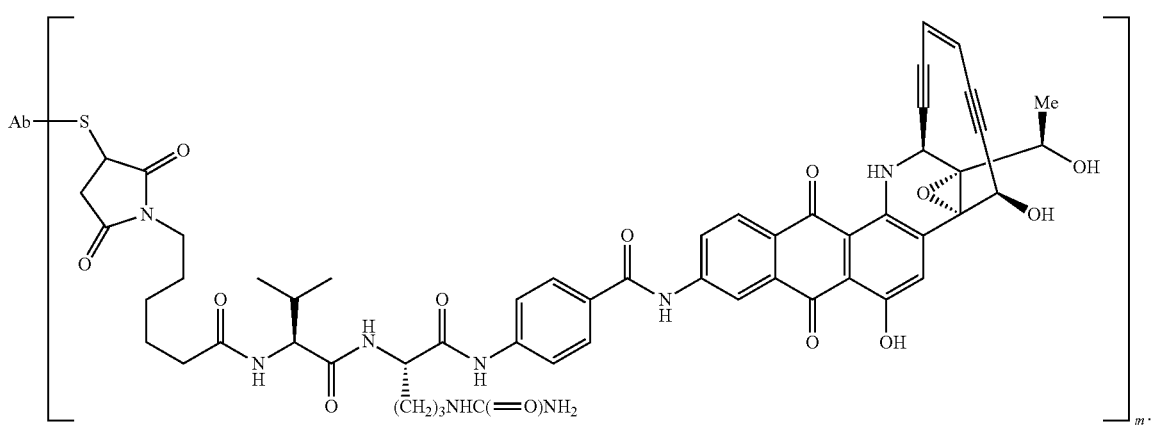
(Vg)

Biological Activity

Data on the biological activity of compounds and conjugates of this invention is provided in Examples 13 and 14 of this specification.

Those skilled in the art will appreciate that when compounds of formula (I), (Ia), or (Ib) where the group $R^{1a}$ is $H_2NCHR^8C(=O)$—such as exemplified in compounds (IIb), (IIf), (IIg) or (IIh)—are used in a conjugate, the moiety $R^{1a}$ can be part of an enzymatically cleavable peptidyl linker whose cleavage does not regenerate the original compound—e.g., (IIb), (IIf), (IIg), or (IIh)—but, rather, compound (IIa).

Pharmaceutical Compositions

In another aspect, the present disclosure provides a pharmaceutical composition comprising a compound of the present invention, or of a conjugate thereof, formulated together with a pharmaceutically acceptable carrier or excipient. It may optionally contain one or more additional pharmaceutically active ingredients, such as an antibody or another drug. The pharmaceutical compositions can be administered in a combination therapy with another therapeutic agent, especially another anti-cancer agent.

The pharmaceutical composition may comprise one or more excipients. Excipients that may be used include carriers, surface active agents, thickening or emulsifying agents, solid binders, dispersion or suspension aids, solubilizers, colorants, flavoring agents, coatings, disintegrating agents, lubricants, sweeteners, preservatives, isotonic agents, and combinations thereof. The selection and use of suitable excipients is taught in Gennaro, ed., *Remington: The Science and Practice of Pharmacy*, 20th Ed. (Lippincott Williams & Wilkins 2003), the disclosure of which is incorporated herein by reference.

Preferably, a pharmaceutical composition is suitable for intravenous, intramuscular, subcutaneous, parenteral, spinal or epidermal administration (e.g., by injection or infusion). Depending on the route of administration, the active compound may be coated in a material to protect it from the action of acids and other natural conditions that may inactivate it. The phrase "parenteral administration" means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, the pharmaceutical composition can be administered via a non-parenteral route, such as a topical, epidermal or mucosal route of administration, for example, intranasally, orally, vaginally, rectally, sublingually or topically.

Pharmaceutical compositions can be in the form of sterile aqueous solutions or dispersions. They can also be formulated in a microemulsion, liposome, or other ordered structure suitable to achieve high drug concentration. The compositions can also be provided in the form of lyophilates, for reconstitution in water prior to administration.

The amount of active ingredient which can be combined with a carrier material to produce a single dosage form will vary depending upon the subject being treated and the particular mode of administration and will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

Dosage regimens are adjusted to provide a therapeutic response. For example, a single bolus may be administered, several divided doses may be administered over time, or the dose may be proportionally reduced or increased as indicated by the exigencies of the situation. It is especially advantageous to formulate parenteral compositions in dosage unit form for ease of administration and uniformity of dosage. "Dosage unit form" refers to physically discrete units suited as unitary dosages for the subjects to be treated; each unit containing a predetermined quantity of active compound calculated to produce the desired therapeutic response, in association with the required pharmaceutical carrier.

The dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. Exemplary treatment regimens are administration once per week, once every two weeks, once every three weeks, once every four weeks, once a month, once every 3 months, or once every three to 6 months. Preferred dosage regimens include 1 mg/kg body weight or 3 mg/kg body weight via intravenous administration, using one of the following dosing schedules: (i) every four weeks for six dosages, then every three months; (ii) every three weeks; (iii) 3 mg/kg body weight once followed by 1 mg/kg body weight every three weeks. In some methods, dosage is adjusted to achieve a plasma antibody concentration of about 1-1000 μg/mL and in some methods about 25-300 μg/mL.

A "therapeutically effective amount" of a compound of the invention preferably results in a decrease in severity of disease symptoms, an increase in frequency and duration of disease symptom-free periods, or a prevention of impairment or disability due to the disease affliction. For example, for the treatment of tumor-bearing subjects, a "therapeutically effective amount" preferably inhibits tumor growth by at least about 20%, more preferably by at least about 40%, even more preferably by at least about 60%, and still more preferably by at least about 80% relative to untreated subjects. A therapeutically effective amount of a therapeutic compound can decrease tumor size, or otherwise ameliorate symptoms in a subject, which is typically a human but can be another mammal.

The pharmaceutical composition can be a controlled or sustained release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. See, e.g., *Sustained and Controlled Release Drug Delivery Systems*, J. R. Robinson, ed., Marcel Dekker, Inc., New York, 1978.

Therapeutic compositions can be administered via medical devices such as (1) needleless hypodermic injection devices (e.g., U.S. Pat. Nos. 5,399,163; 5,383,851; 5,312,335; 5,064,413; 4,941,880; 4,790,824; and 4,596,556); (2) micro-infusion pumps (U.S. Pat. No. 4,487,603); (3) transdermal devices (U.S. Pat. No. 4,486,194); (4) infusion apparati (U.S. Pat. Nos. 4,447,233 and 4,447,224); and (5) osmotic devices (U.S. Pat. Nos. 4,439,196 and 4,475,196); the disclosures of which are incorporated herein by reference.

In certain embodiments, the pharmaceutical composition can be formulated to ensure proper distribution in vivo. For example, to ensure that the therapeutic compounds of the invention cross the blood-brain barrier, they can be formulated in liposomes, which may additionally comprise targeting moieties to enhance selective transport to specific cells or organs. See, e.g. U.S. Pat. Nos. 4,522,811; 5,374,548; 5,416, 016; and 5,399,331; V. V. Ranade (1989) *J. Clin. Pharmacol.* 29:685; Umezawa et al., (1988) *Biochem. Biophys. Res. Commun.* 153:1038; Bloeman et al. (1995) *FEBS Lett.* 357:140; M. Owais et al. (1995) *Antimicrob. Agents Chemother.* 39:180; Briscoe et al. (1995)*Am. J. Physiol.* 1233:134; Schreier et al. (1994) *J. Biol. Chem.* 269:9090; Keinanen and Laukkanen (1994) *FEBS Lett.* 346:123; and Killion and Fidler (1994) *Immunomethods* 4:273.

Uses

Compounds of this invention or their conjugates can be used for treating diseases such as, but not limited to, hyperproliferative diseases, including: cancers of the head and neck which include tumors of the head, neck, nasal cavity, paranasal sinuses, nasopharynx, oral cavity, oropharynx, larynx, hypopharynx, salivary glands, and paragangliomas; cancers of the liver and biliary tree, particularly hepatocellular carcinoma; intestinal cancers, particularly colorectal cancer; ovarian cancer; small cell and non-small cell lung cancer (SCLC and NSCLC); breast cancer sarcomas, such as fibrosarcoma, malignant fibrous histiocytoma, embryonal rhabdomyosarcoma, leiomysosarcoma, neurofibrosarcoma, osteosarcoma, synovial sarcoma, liposarcoma, and alveolar soft part sarcoma; leukemias such as acute promyelocytic leukemia (APL), acute myelogenous leukemia (AML), acute lymphoblastic leukemia (ALL), and chronic myelogenous leukemia (CML); neoplasms of the central nervous systems, particularly brain cancer; multiple myeloma (MM), lymphomas such as Hodgkin's lymphoma, lymphoplasmacytoid lymphoma, follicular lymphoma, mucosa-associated lymphoid tissue lymphoma, mantle cell lymphoma, B-lineage large cell lymphoma, Burkitt's lymphoma, and T-cell anaplastic large cell lymphoma. Clinically, practice of the methods and use of compositions described herein will result in a reduction in the size or number of the cancerous growth and/or a reduction in associated symptoms (where applicable). Pathologically, practice of the method and use of compositions described herein will produce a pathologically relevant response, such as: inhibition of cancer cell proliferation, reduction in the size of the cancer or tumor, prevention of further metastasis, and inhibition of tumor angiogenesis. The method of treating such diseases comprises administering a therapeutically effective amount of an inventive combination to a subject. The method may be repeated as necessary. Especially, the cancer can be colorectal cancer, liver cancer, prostate cancer, breast cancer, melanoma, glioblastoma, lung cancer, pancreatic cancer, ovarian cancer, multiple myeloma, renal cancer, leukemia (especially ALL, APL, or AML), or lymphoma.

Compounds of this invention or their conjugates can be administered in combination with other therapeutic agents, including antibodies, alkylating agents, angiogenesis inhibitors, antimetabolites, DNA cleavers, DNA crosslinkers, DNA intercalators, DNA minor groove binders, enediynes, heat shock protein 90 inhibitors, histone deacetylase inhibitors, immunomodulators, microtubule stabilizers, nucleoside (purine or pyrimidine) analogs, nuclear export inhibitors, proteasome inhibitors, topoisomerase (I or II) inhibitors, tyrosine kinase inhibitors, and serine/threonine kinase inhibitors. Specific therapeutic agents include adalimumab, ansamitocin P3, auristatin, bendamustine, bevacizumab, bicalutamide, bleomycin, bortezomib, busulfan, callistatin A, camptothecin, capecitabine, carboplatin, carmustine, cetuximab, cisplatin, cladribin, cytarabin, cryptophycins, dacarbazine, dasatinib, daunorubicin, docetaxel, doxorubicin, duocarmycin, dynemycin A, epothilones, etoposide, floxuridine, fludarabine, 5-fluorouracil, gefitinib, gemcitabine, ipilimumab, hydroxyurea, imatinib, infliximab, interferons, interleukins, β-lapachone, lenalidomide, irinotecan, maytansine, mechlorethamine, melphalan, 6-mercaptopurine, methotrexate, mitomycin C, nilotinib, oxaliplatin, paclitaxel, procarbazine, suberoylanilide hydroxamic acid (SAHA), 6-thioguanidine, thiotepa, teniposide, topotecan, trastuzumab, trichostatin A, vinblastine, vincristine, and vindesine.

EXAMPLES

The practice of this invention can be further understood by reference to the following examples, which are provided by way of illustration and not of limitation.

Example 1

Compound (IIa)

Figure 1:
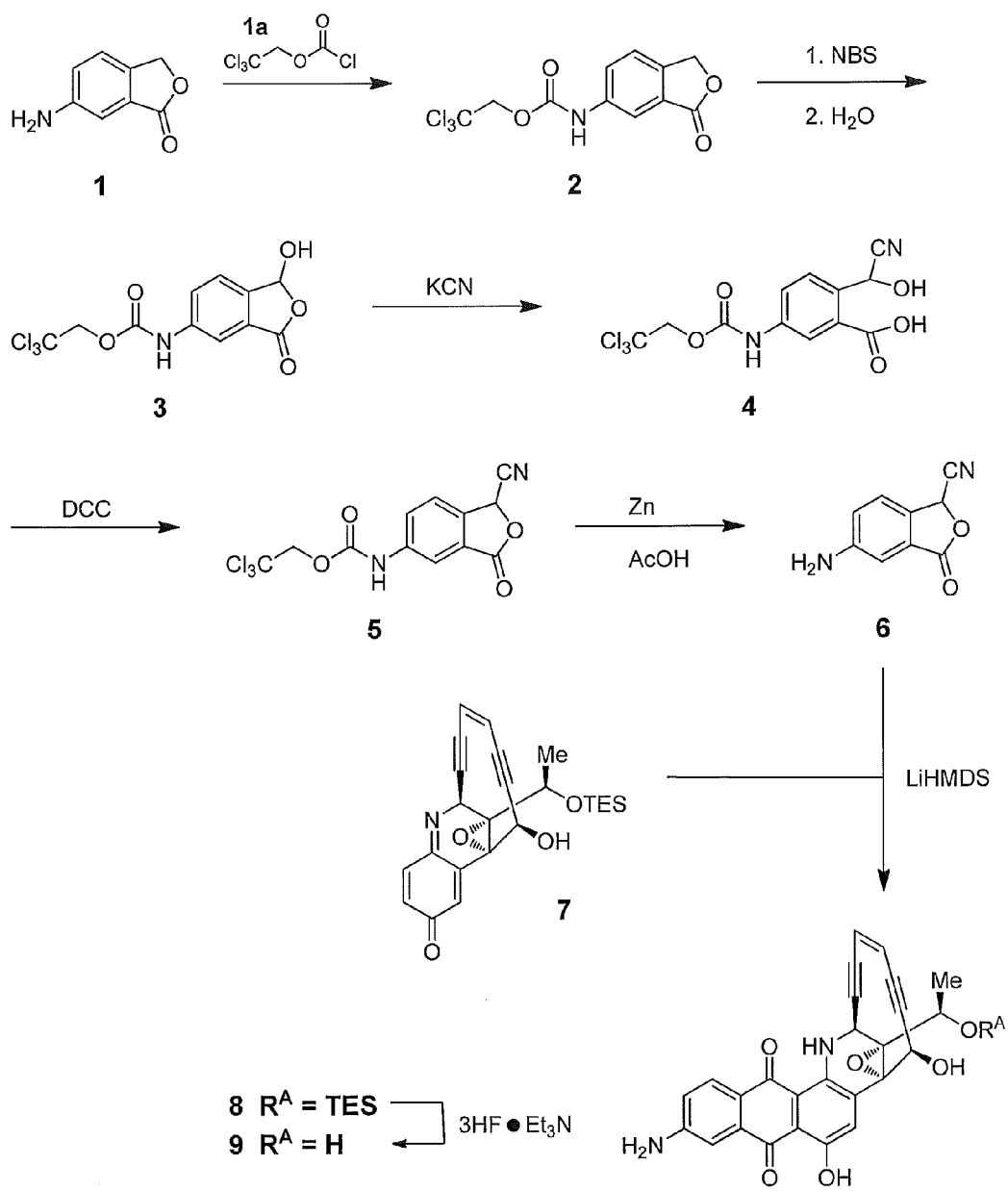
FIGS. 1 through 6 show schemes for the synthesis of compounds of this invention.

This example describes the preparation of compound (IIa), or 8-aminouncialamycin. The synthetic scheme for its preparation is shown in FIG. 1, where it is labeled compound 9.

2,2,2-trichloroethyl(3-oxo-1,3-dihydroisobenzofuran-5-yl)carbamate 2

To a suspension of 6-aminoisobenzofuran-1(3H)-one 1 (Maybridge, 13.43 g, 90 mmol) in dichloromethane (DCM, 200 mL) at 0° C. was added 2,2,2-trichloroethyl carbonochloridate 1a (18.23 mL, 135 mmol) and pyridine (17.79 mL, 180 mmol). The reaction mixture was stirred at room temperature (RT, ca. 25° C.) for 1 h. Thin layer chromatography (TLC) and high performance liquid chromatography (HPLC) showed the reaction was complete. The reaction mixture was filtered and washed with DCM (2×30 mL) to afford carbamate 2 as a white solid (17.03 g, 58%). LCMS: [M+1]=324.

Hydroxyphthalide 3

A suspension of carbamate 2 (17.0 g, 52.4 mmol), N-bromosuccinimide (NBS, 10.26 g, 57.6 mmol) in $CCl_4$ (150 mL) was stirred and heated to reflux (85° C. oil bath). The reaction mixture was exposed to light from a sun lamp that was situated approximately 10 cm from the flask. After 2 h TLC showed the reaction was complete. HPLC showed multiple peaks due to the labile nature of the intermediate bromide. Concentration on a rotary evaporator yielded a brown solid. Water (200 mL) was added to the brown solid in situ and heated to reflux for 5 h to produce an almost clear solution with some insoluble material. TLC and HPLC showed reaction was complete. Concentration on a rotary evaporator followed by purification with a COMBIFLASH™ unit using a 0-50% EtOAc gradient in hexanes on a 120 g silica column afforded hydroxyphthalide 3 (13.55 g, 76%). LCMS: [M+1]=340.

Cyanophthalide 5

To a suspension of hydroxyphthalide 3 (1.391 g, 4.09 mmol) and potassium cyanide (399 mg, 6.14 mmol, 1.5 equiv.) in water (4 mL) was slowly added 33% aqueous HCl (1.2 mL) at 0° C. (ice bath). The ice bath was removed and stirring continued for 2 h. LCMS (m+1=368) showed the formation of compound 4. The reaction mixture was extracted with EtOAc, dried over $MgSO_4$, and concentrated to 20 mL. After cooling to 0° C., the solution was treated with dicyclohexyl carbodiimide (DCC, 1.2 equiv.) and stirring was continued at RT for 8 h. The reaction mixture was filtered to remove the urea byproduct and the filtrate was concentrated by flash column chromatography with 30% EtOAc/hexane gradient to yield cyanophthalide 5 (1.116 g, 78% yield) as a white solid. $^1$H NMR (400 MHz, CDCl$_3$): δ 8.10 (d, J=2.0 Hz, 1H), 7.93 (dd, J=8.8, 2.0 Hz, 1H), 7.67 (d, J=8.8 Hz, 1H), 6.06 (s, 1H), 4.87 (s, 1H).

Aminocyanophthalide 6

Zinc (8.58 g, 131 mmol) was added to a solution of cyanophthalide 5 (3 g, 8.58 mmol) in acetic acid (82 mL) and water (4.3 mL) at RT. After 30 min TLC and HPLC showed the reaction was complete with a 3:1 ratio of product and monodechlorinated byproduct. Filtration over CELITE™ and washing with EtOAc (50 mL) and water (50 mL), followed by concentration and purification on COMBI-FLASH™ 40 g silica column using 0-50% EtOAc/hexane gradient afforded aminocyanophthalide 6 as a white solid (980 mg, 66% yield). $^1$H NMR (400 MHz, CDCl$_3$): δ 7.46 (d, J=8.4 Hz, 1H), 7.05 (dd, J=8.4, 2.4 Hz, 1H), 6.95 (d, J=2.4 Hz, 1H), 6.47 (s, 1H).

8-Aminouncialamycin-OTES 8

A Hauser annulation procedure was employed. To a solution of aminocyanophthalide 6 (155 mg, 0.891 mmol) in tetrahydrofuran (THF, 5.3 mL) at −70° C. was added lithium bis(trimethylsilyl)amide (LiHMDS, 1.782 mL, 1.782 mmol). The reaction mixture was stirred for 20 min. A precooled solution of iminoquinone 7 (made per Nicolaou et al. 2007a, 125 mg, 0.297 mmol) in THF (12.5 mL) was added. The reaction mixture was stirred at the same temperature for 5 min and then slowly warmed to RT over 30 min. The reaction was quenched with phosphate buffer (pH 6.8, 100 mL) and extracted with EtOAc (3×75 mL). The combined extracts were dried over MgSO$_4$ to afford crude product. Purification on a COMBIFLASH™ 12 g silica gel column using 0-50% EtOAc/hexanes gradient yielded product 8 as a purple solid (60 mg, 36% yield). LCMS: [M+1]=569. $^1$H NMR (400 MHz, CD$_3$CN): δ 13.14 (s, 1H), 9.96 (d, J=4.0 Hz, 1H), 8.40 (m, 1H), 8.03 (d, J=9.6 Hz, 1H), 7.38 (m, 1H), 7.02 (td, J=8.0 Hz, J=1.6 Hz 1H), 5.92 (dd, J=24, 9.6 Hz, 2H), 5.20 (s, 2H), 5.12 (d, J=4.4 Hz, 1H), 4.94 (d, J=4.0 Hz, 1H), 4.65 (m, 1H), 4.55 (q, J=6.4 Hz, 1H), 4.46 (d, J=4.8 Hz, 1H), 3.41 (m, 1H), 1.40 (d, J=6.0 Hz, 3H), 1.00 (t, J=8.0 Hz, 9H), 0.68 (q, J=7.2 Hz, 3H).

8-Aminouncialamycin 9

Aminouncialamycin-OTES 8 (30 mg) was dissolved in THF (3 mL) and treated with a solution of Et$_3$N.3HF in THF (1:1, 1.5 mL) at RT. After 1 h, desilylation was complete as monitored by TLC and HPLC. The reaction mixture was taken up in EtOAc, washed with saturated NaHCO$_3$ solution, dried over MgSO$_4$ and concentrated. Purification on a COMBIFLASH™ silica gel column using 0-55% EtOAc/hexanes gradient afforded 8-aminouncialamycin 9 as a purple solid (80% yield). LCMS: [M+1]=455.

Those skilled in the art will appreciate that variants of compound (IIa) with the amino group located at other ring positions can be made by using as a starting material variants of compound 1 with its amino group elsewhere in the ring or replaced by a different group, as in:

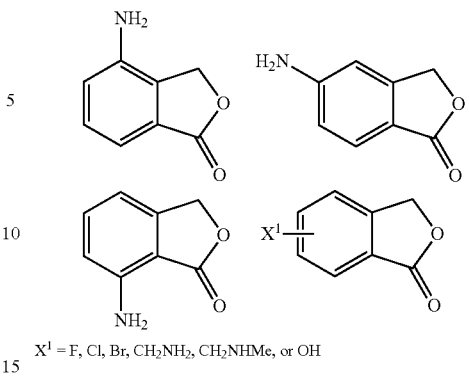

$X^1$ = F, Cl, Br, CH$_2$NH$_2$, CH$_2$NHMe, or OH

Example 2

Compounds (IIb), (IIg), and (IIh)

Figure 2:
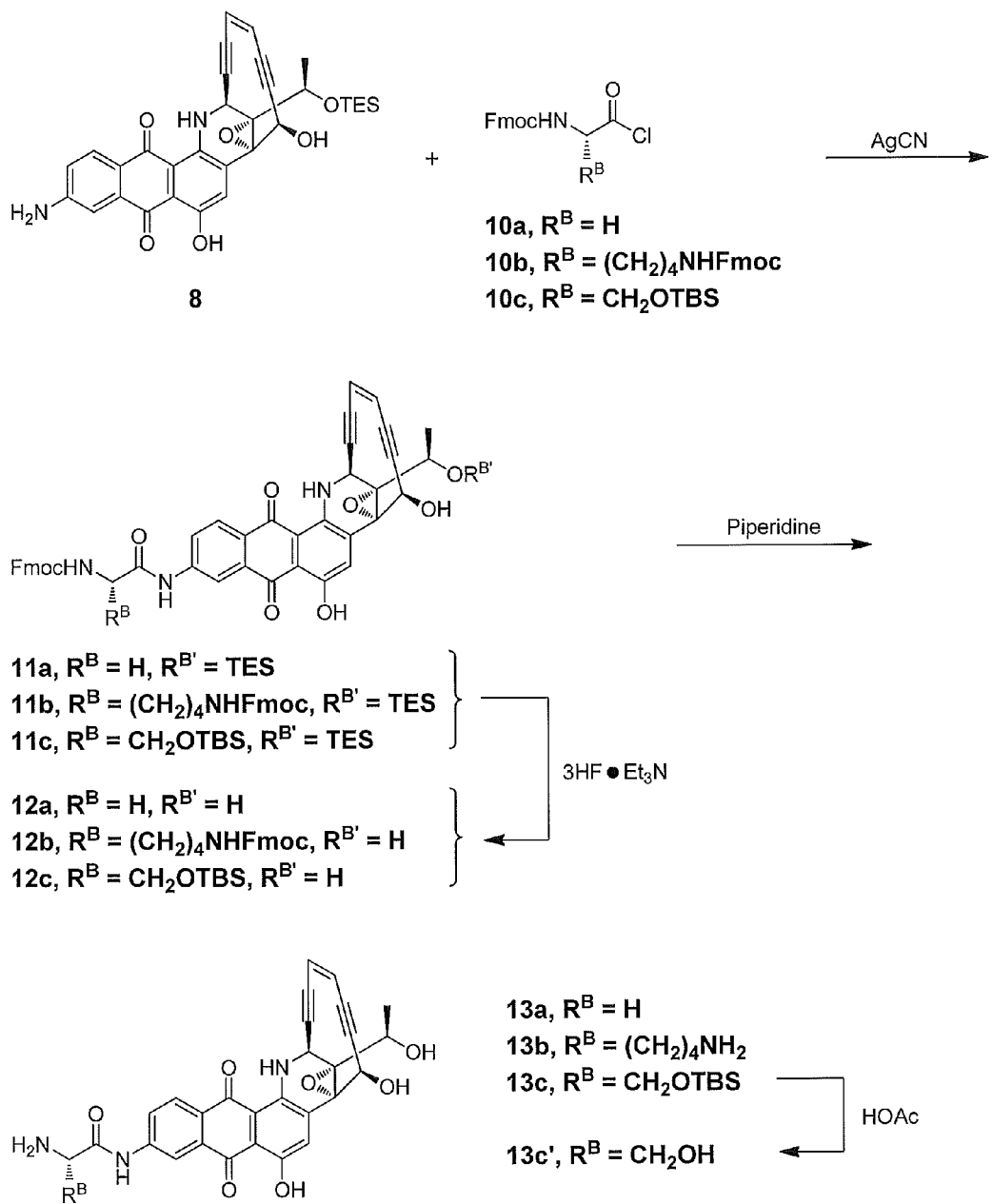

Although the 8-amino group in 8-aminouncialamycin is not especially reactive, it can be amidated with an α-amino acid chloride in the presence of silver cyanide. FIG. 2 shows illustrative procedures for preparing compounds (IIb), (IIh), and (IIg), via this procedure. In FIG. 2 compounds (IIb), (IIh), and (IIg) are labeled 13a, 13b, and 13c', respectively.

Fmoc-Gly-NH-uncialamycin-OTES 11a

Aminouncialamycin-OTES 8 (5 mg) and Fmoc-protected glycinyl chloride 10a (Chem-Impex, 8.4 mg, 3 equiv) were dissolved in acetonitrile (2 mL) and stirred in the presence of AgCN (7 mg, 6 equiv) overnight. Reaction was complete as monitored by TLC and HPLC. Concentration and purification on a COMBIFLASH™ silica gel column using 0-40% EtOAc/hexanes gradient afforded product 11a as a purple solid (90% yield). LCMS: [M+1]=848.

Fmoc-Gly-NH-uncialamycin 12a

Product 11a (4 mg) was dissolved in THF (0.5 mL) and treated with a solution of Et$_3$N.3HF.THF (1:1, 0.25 mL) at RT. After 1 h desilylation was complete as monitored by TLC and HPLC. The reaction mixture was taken up in EtOAc, washed with saturated NaHCO$_3$ solution, dried over MgSO$_4$ and concentrated. Purification on a COMBIFLASH™ silica gel column using a 0-55% EtOAc/hexanes gradient afforded compound 12a as a purple solid (80% yield). LCMS: [M+1]=734.

Gly-NH-uncialamycin 13a

Compound 12a (2 mg) was treated with 20% piperidine in N,N-dimethylformamide (DMF, 1 mL) at RT for 15 min. Concentration and purification using reverse phase HPLC (R-HPLC) with 0.1% TFA in acetonitrile/water eluent afforded compound 13a (50% yield). LCMS: [M+1]=512.

The analogous lysine and serine compounds 13b and 13c' were prepared using the same general procedures. Acid chlorides 10b and 10c were prepared from the corresponding carboxylic acids (both from Chem-Impex) by reaction with thionyl chloride or Ghosez's reagent. Removal of the TES group from compound 13c can be accomplished with acetic acid. Compound 13b: LCMS [M+1]=583.2; compound 11c: LCMS [M+1]=770.3.

Example 3

Compound (IIf)

Figure 3:
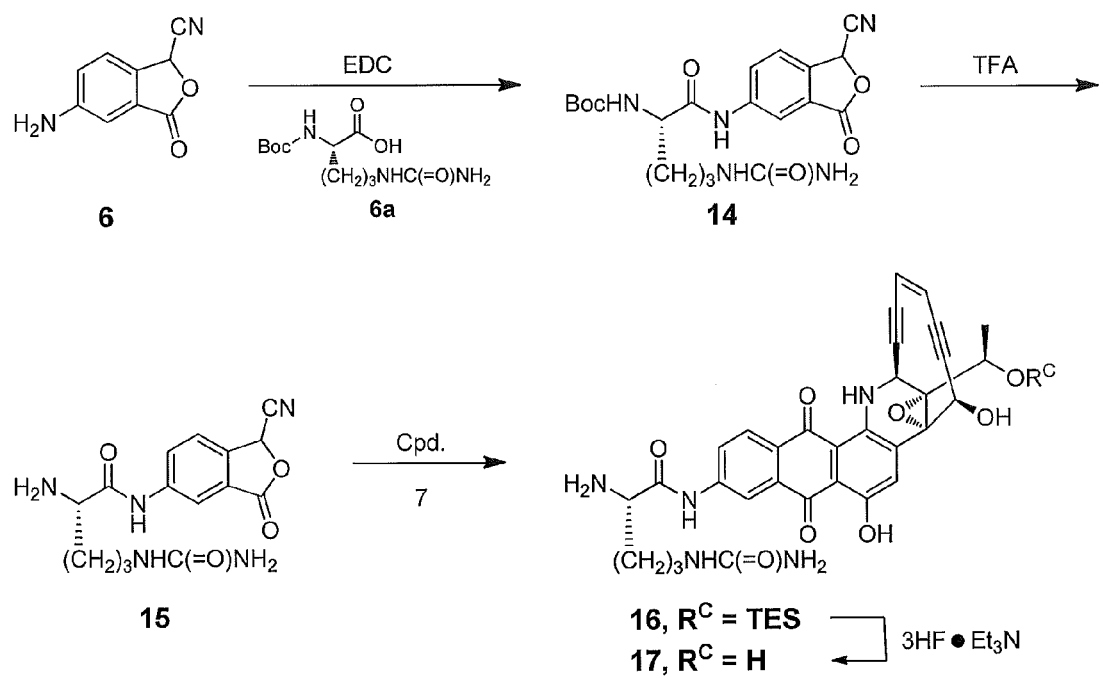

The procedure of the previous example was not usable with citrulline, because of the instability of citrulline acid chloride. An alternative synthetic approach was devised, in which the citrulline was attached to the phthalide before condensation with compound 7, as shown in FIG. 3, to produce compound (IIf), labeled 17 in the figure.

Fmoc-citrulline coupled cyanophthalide 14

Boc-protected citrulline 6a (Chem-Impex, 0.726 g, 2.64 mmol) and N-(3-dimethylaminopropyl)-N'-ethylcarbodiimide hydrochloride (EDC, 0.578 g, 2.9 mmol) in DCM:DMF (17:3,20 mL) was stirred at RT for 30 min. Then aminocyanophthalide 6 (0.23 g, 1.32 mmol) was added and stirred at RT for 18 h. The reaction mixture was worked up with ethyl acetate, washed with saturated $NaHCO_3$ solution, and further washed with water and brine. Concentration and purification with a COMBIFLASH column eluting with 17% MeOH in DCM afforded cyanophthalide 14 (40% yield). LCMS: [M+1]=432. $^1$H NMR (400 MHz, DMSO-$d_6$): δ 10.50 (s, 1H), 8.37 (d, J=8.4 Hz, 1H), 7.96 (m, 1H), 7.91 (d, J=8.0 Hz, 1H), 7.16 (d, J=8.0 Hz, 1H), 6.72 (s, 1H), 5.40 (s, 2H), 4.02 (m, 2H), 2.92 (m, 2H), 1.60 (m, 2H), 1.36 (m, 9H). $^{13}$C NMR (100 MHz, DMSO-$d_6$): δ 172.7, 168.3, 159.3, 156.0, 141.9, 137.0, 126.7, 125.0, 124.5, 115.7, 114.8, 78.5, 66.7, 55.3, 29.4, 28.6, 27.3.

Compound 15.

Phthalide 14 was treated with DCM-trifluoroacetic acid (TFA) (1:1) to afford compound 15. LCMS: [M+1]=332.

Compound 17.

Without further purification, the TFA salt of compound 15 was subjected to Hauser annulation with iminoquinone 7, employing the general conditions described above to afford TES protected compound 16 (10% yield). Desilylation of compound 16 with $Et_3N.3HF$ followed by R-HPLC using 0.1% TFA in $CH_3CN$/water provided compound 17. LCMS: [M+1]=612.

Example 4

Compound (IIc)

Figure 4:
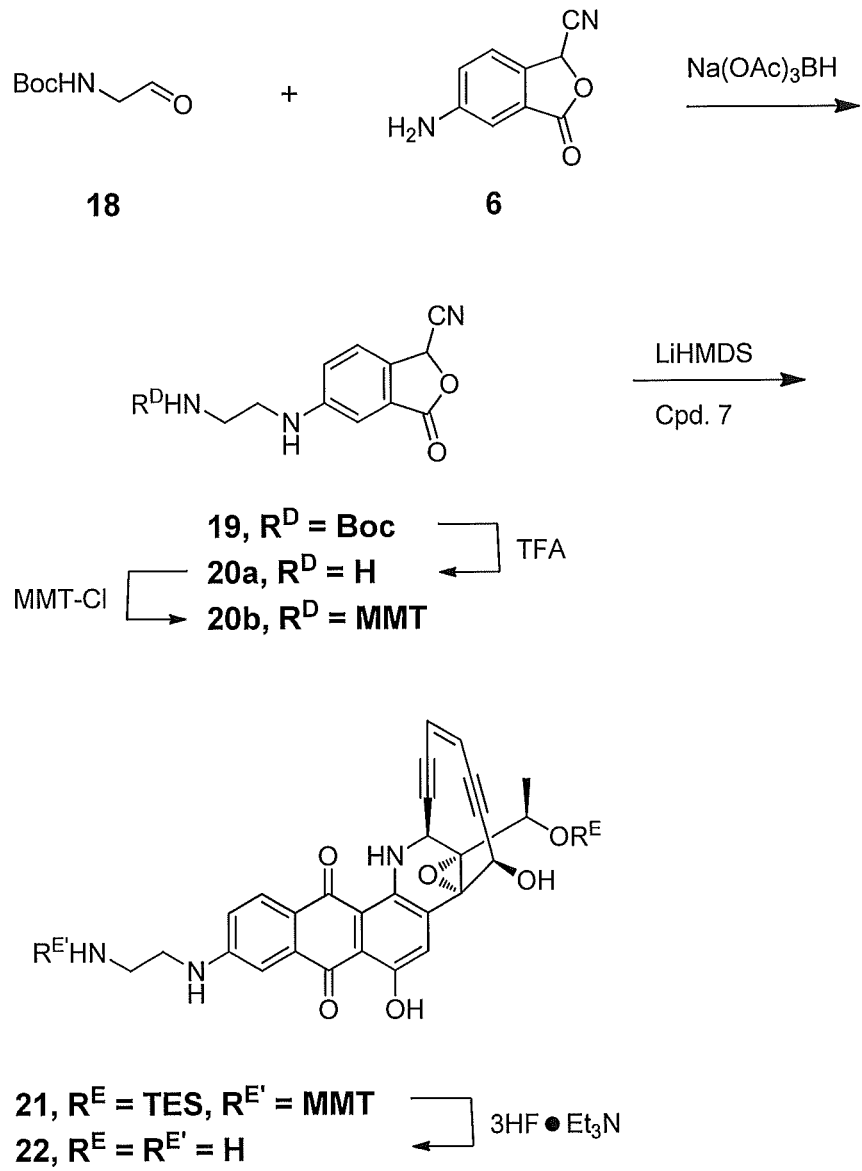

FIG. 4 shows a scheme for the synthesis of compound (IIc), labeled 22 in the figure.

Compound 19.

To a solution of aminocyanophthalide 6 (300 mg, 1.723 mmol), compound 18 (Aldrich-Sigma, 823 mg, 5.17 mmol) and acetic acid (5 equiv) in $ClCH_2CH_2Cl$ (30 mL) was added sodium triacetoxy borohydride (3 equiv) and stirred at RT for 5 h. HPLC showed 90% conversion. The reaction mixture was taken up in DCM (100 mL) and washed with saturated $NaHCO_3$ solution (50 mL). Concentration and purification using a COMBIFLASH™ column with 40% EtOAc/hexanes as eluent afforded compound 19. $^1$H NMR (400 MHz, DMSO-$d_6$): δ 7.53 (d, J=8.4 Hz, 1H), 7.07 (dd, J=8.8, 2.4 Hz, 1H), 6.89 (d, J=2.0 Hz, 1H), 6.85 (brs, 1H), 6.56 (s, 1H), 4.0 (brs, 1H), 3.06-3.13 (m, 4H), 1.34 (m, 9H).

Compound 20a.

Compound 19 was dissolved in DCM (6 mL) and treated with TFA (3 mL) at 0° C. The temperature was allowed to rise to RT and the reaction mixture was stirred for 30 min. HPLC showed the reaction was complete. The reaction mixture was concentrated to afford a gummy material, which was washed with ether (2×20 mL), dissolved in acetonitrile/water and lyophilized to yield compound 20a (601 mg, 78% yield). LCMS: [M+1]=218.

Compound 20b.

To a solution of compound 20a (200 mg, 0.451 mmol, as bis-TFA salt) in DMF (2 mL) at 0° C. was added triethylamine (0.314 mL, 2.256 mmol) followed by (chloro(4-methoxyphenyl)methylene)dibenzene (167 mg, 0.541 mmol) in DCM (2 mL). The reaction mixture was stirred at RT for 1 h and worked up with EtOAc and water. Purification on a neutral alumina column using 30% EtOAc in hexanes afforded p-methoxyphenyldiphenylmethyl (MMT) protected product 20b as a pale yellow solid (105 mg, 48% yield). Purity was checked by TLC with a triethylamine:EtOAc:hexane (1:30:70) mobile phase. $^1$H NMR (400 MHz, $CDCl_3$): δ 7.2-7.7 (m, 16H), 7.0 (m, 2H), 6.8 (m, 3H), 6.19 (s, 1H), 4.57 (brs, 1H), 3.77 (m, 3H), 3.28 (m, 2H), 2.50 (m, 2H).

Compound 22.

To a solution of product 20b (92 mg, 0.188 mmol) in THF (2 mL) at −70° C. was added LiHMDS (0.376 mL, 0.376 mmol). The reaction mixture was stirred for 20 min. A precooled solution of iminoquinone 7 (52.8 mg, 0.125 mmol) in THF (2.6 mL) was added and stirred at the same temperature for 5 min. The reaction mixture was slowly warmed to RT over 20 min, quenched with phosphate buffer (pH 6.8, 20 mL) and extracted with EtOAc (3×15 mL). The combined organic phases were washed with brine (30 mL) and dried over $MgSO_4$ to afford crude product 21. Unpurified product 21 was dissolved in DMSO (2 mL) and treated with $Et_3N.3HF$ (0.5 mL) at 4° C. and stirred at RT. After 1 h LCMS showed formation of product. The crude product was purified on an X-Bridge prep C18 column 5 μm OBD (30×150 mm) using 0.1% TFA in acetonitrile/water as mobile phase. Lyophilization yielded product 22 (14.4 mg, 23% yield over two steps). LCMS [M+1]=498.3.

Example 5

Compound (IIe)

Figure 5:
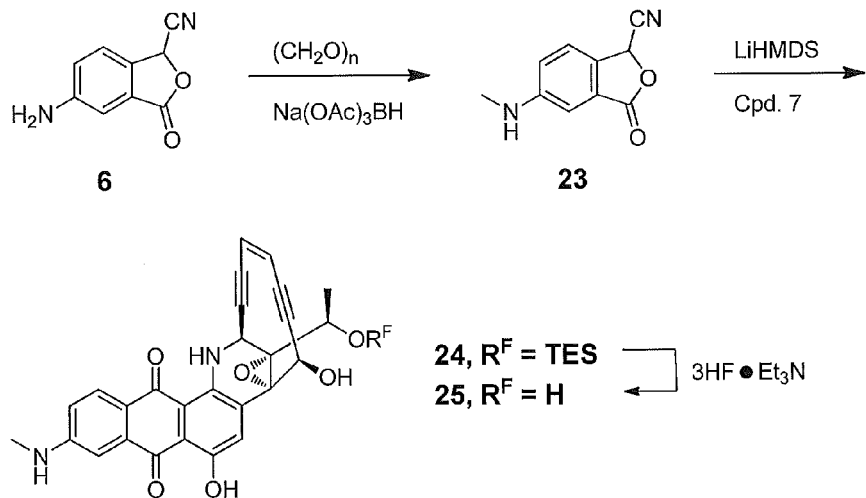

FIG. 5 shows a scheme for the synthesis of compound (IIe), labeled 25 in the figure.

8-Methylaminouncialamycin 25

To a solution of aminocyanophthalide 6 (34 mg, 0.195 mmol), paraformaldehyde (11.72 mg, 0.390 mmol) and acetic acid in $ClCH_2CH_2Cl$ (2 mL) was added sodium triacetoxy borohydride. The reaction mixture was kept at RT for 24 h. HPLC showed 90% conversion. The reaction mixture was taken up with EtOAc (20 mL) and washed with saturated $NaHCO_3$ solution (10 mL). Concentration and purification by R-HPLC yielded product 23 (15 mg, 41% yield). MS (m+1)=189. Product 23 was subjected to Hauser annulation followed by TES deprotection as described hereinabove to provide 8-methylaminouncialamycin 25. LCMS: (M+1)=467.

Example 6

Compound (IId)

Figure 6:
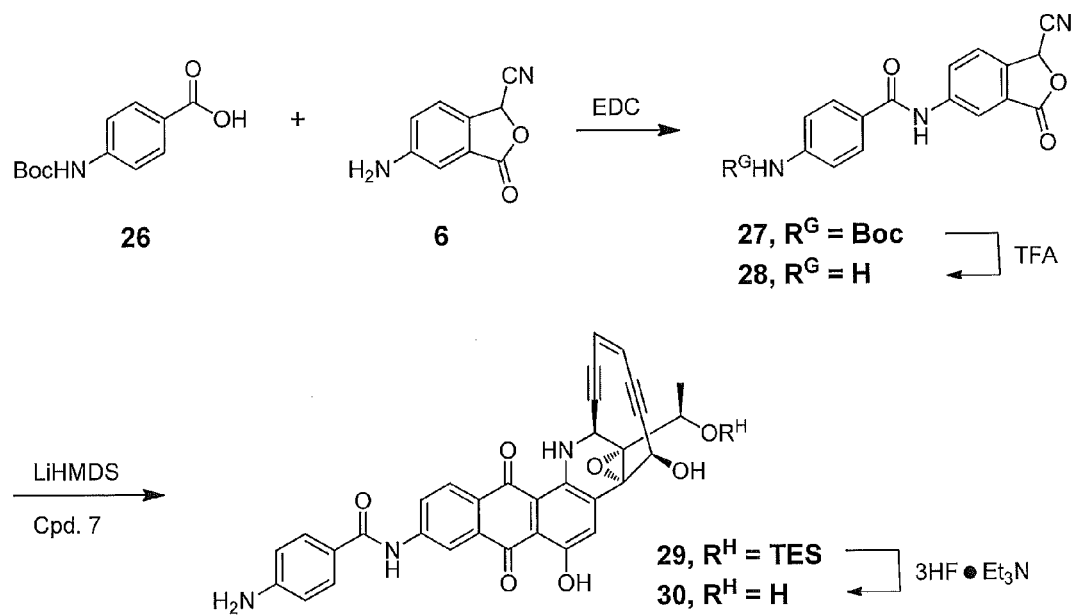

FIG. 6 shows a scheme for the synthesis of compound (IId), labeled 30 in the figure.

Compound 30.

A combination of 4-((tert-butoxycarbonyl)amino)benzoic acid 26 (Fluka, 1.885 g, 7.95 mmol) and EDC (1.676 g, 8.74 mmol) in DCM (24 mL) was stirred at RT for 30 min. Then aminocyanophthalide 6 (0.346 g, 1.987 mmol) in DMF (6.00 mL) was added. The reaction mixture was stirred at RT for 5 h. The temperature was raised to 50° C.; after 40 h the DCM was removed by evaporation. The residue was taken up in EtOAc. The EtOAc was washed with saturated $NaHCO_3$, water, and brine. Concentration and purification on a COMBIFLASH™ unit using 15% MeOH in DCM eluent to yield compound 27 as a yellow solid (587 mg, 75% yield). LCMS: [M+1]=394. $^1$H NMR (400 MHz, DMSO-$d_6$): δ 10.53 (s, 1H), 9.71 (s, 1H), 8.42 (d, J=2.0 Hz, 1H), 8.19 (dd, J=8.4, 2.0 Hz, 1H), 7.9 (m, 3H), 7.59 (dd, J=7.2, J=2.0 Hz, 2H), 6.74 (s, 1H), 1.47 (m, 9H). This material 27 (567 mg, 1.441 mmol) was suspended in DCM (2 mL) and TFA (2 mL, 26.0 mmol) was added. After stirring at RT for 50 min, LCMS and HPLC showed the reaction was complete. Concentration and drying under high vacuum for 2 h afforded compound 28, which was subjected to Hauser annulation followed by TES deprotection with $Et_3N.3HF$ as described above to provide compound 30 (18% yield). LCMS: M+1=574.2.

Example 7

Adaptation of Compound (IIb) for Conjugation

Figure 7:
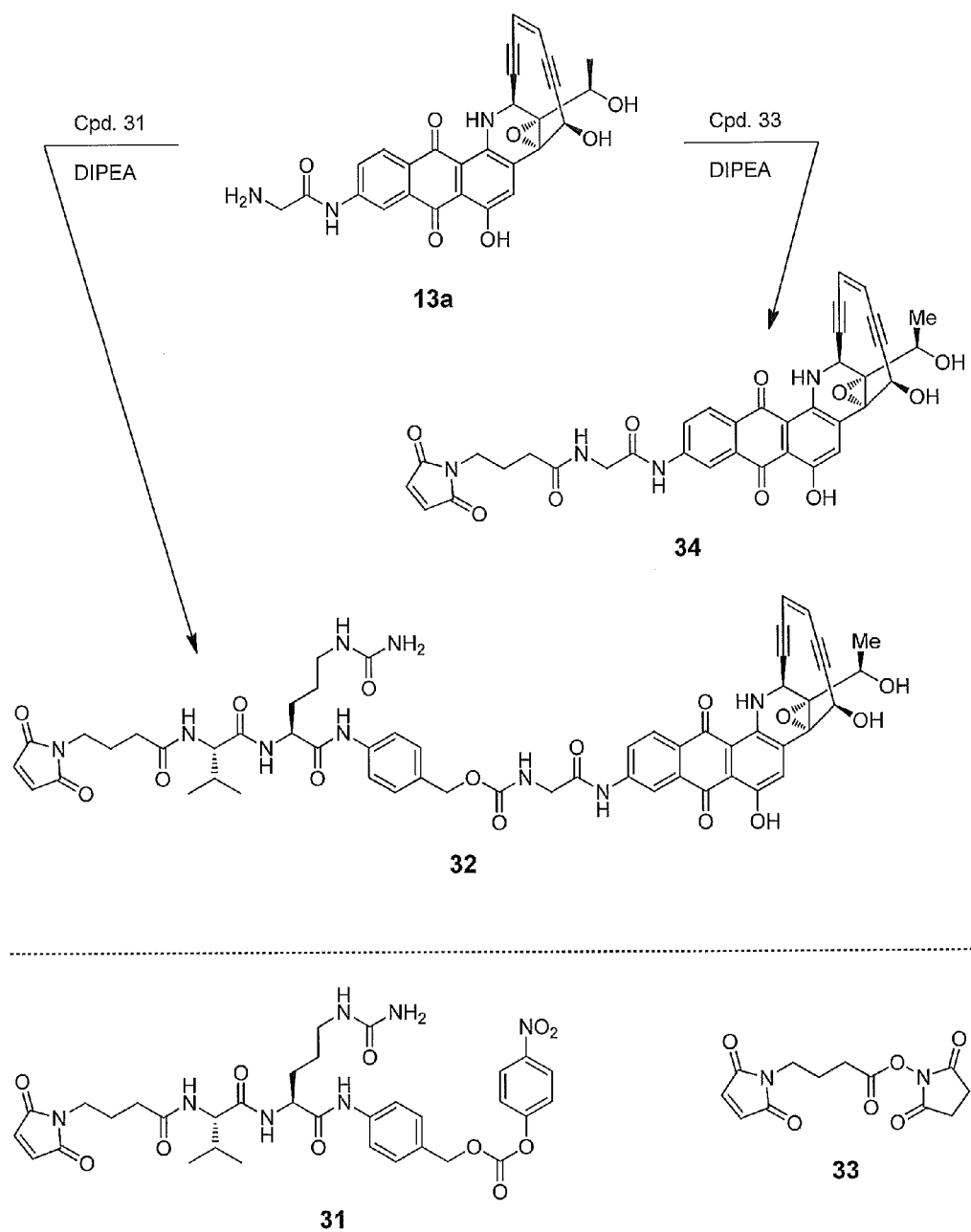
FIGS. 7 through 10 show reaction schemes for the attachment of linker and reactive functional groups to compounds of this invention, in preparation for conjugation.

FIG. 7 shows reaction schemes for adapting compound (IIb) for conjugation.

Compound 32.

Compounds 13a (1 equiv.) and 31 (Dubowchik et al. 2002; 1.2 equiv) in DMSO were treated with N,N-diisopropylethylamine (DIPEA, 3 equiv) at RT for 1 h. Purification by R-HPLC using 0.1% TFA in $CH_3CN$/water as eluent afforded compound 32 (50% yield). LCMS: [M+1]=1082. $^1$H NMR (400 MHz, DMSO-$d_6$): δ 13.12 (s, 1H), 10.62 (s, 1H), 9.67 (m, 1H), 8.49 (s, 1H), 8.29 (d, J=9.2 Hz, 1H), 8.19 (d, J=9.2 Hz, 1H), 8.07 (m, 1H), 7.83 (d, J=8.4 Hz, 1H), 7.57 (m, 2H), 7.29 (m, 2H), 6.98 (m, 1H), 6.65 (d, J=4.8 Hz, 1H), 5.99 (dd, J=30, 9.2 Hz, 2H), 5.38 (d, J=4.8 Hz, 1H), 5.14 (d, J=4.8 Hz, 1H), 5.03 (m, 1H), 4.97 (s, 1H), 4.16 (t, J=7.6 Hz, 1H), 4.08 (q, J=5.2 Hz, 4H), 3.86 (d, J=6.0 Hz, 1H), 3.38 (t, J=6.8 Hz, 1H), 2.90 (m, 2H), 1.94 (m, 2H), 1.69 (m, 2H), 1.29 (d, J=6.4 Hz, 3H), 0.83 (m, 6H).

Compound 34.

A similar reaction of the N-hydroxysuccinimide ester of maleimidobutanoic acid 33 (TCI) afforded compound 34. LCMS: [M+1]=677.

Example 8

Adaptation of Compound (IIf) for Conjugation

Figure 8:
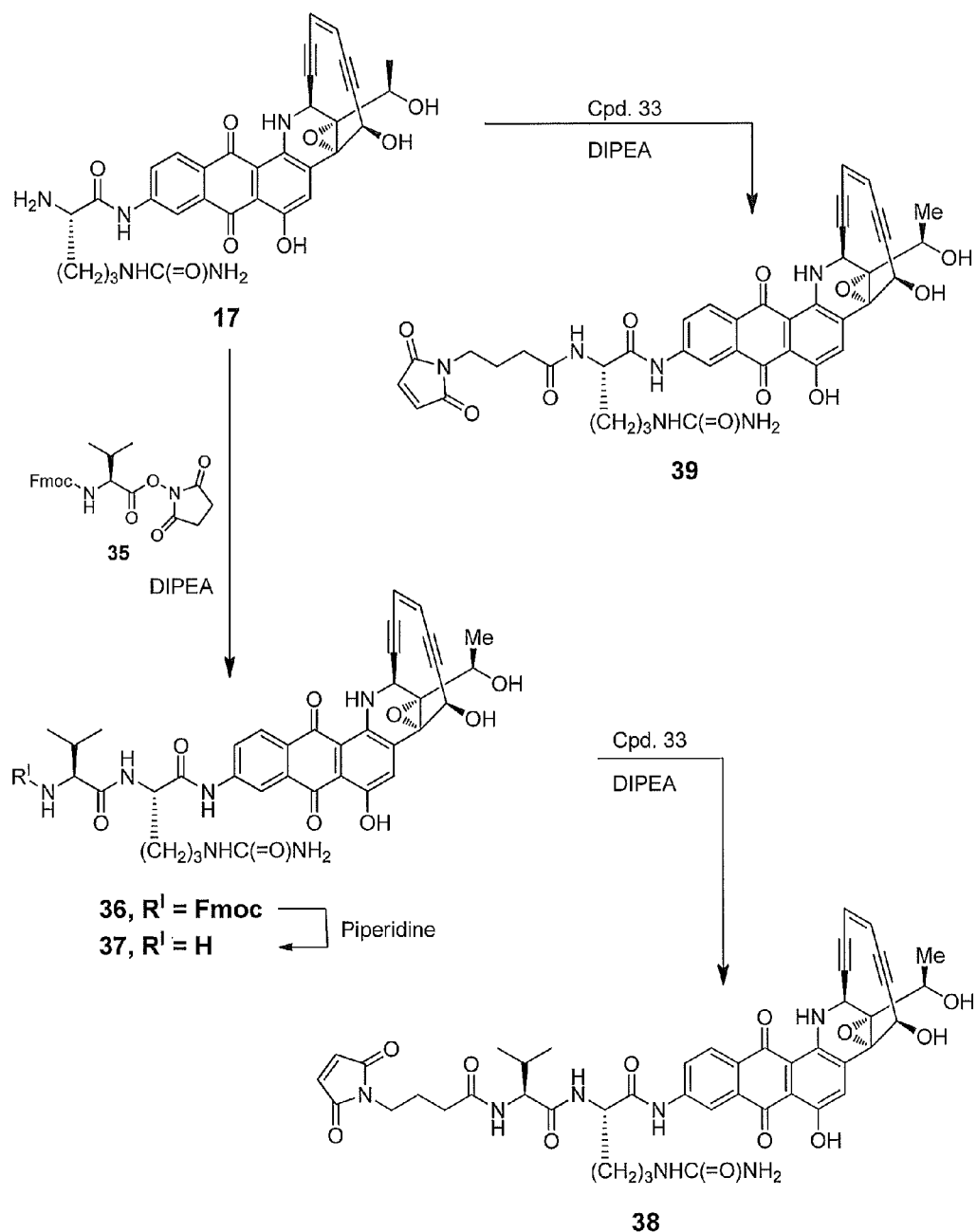

FIG. 8 shows reaction schemes for adapting compound (IIf) for conjugation.

Compound 38.

To a solution of compounds 17 (5 mg) and 35 (Bachem, 10 mg, 22 μmol) in DMF (2 mL) was added DIPEA (16 μl). The reaction mixture was stirred at RT for 7 h. Concentration and purification with a COMBIFLASH™ unit using 30% MeOH in DCM eluent yielded compound 36 (29% yield). Compound 36 was treated with 20% piperidine in DMF (2 mL). After stirring at RT for 15 min, LCMS showed the reaction was complete. The piperidine was removed on a rotary evaporator. The reaction mixture was absorbed onto silica gel and purified with a COMBIFLASH™ unit using 30% methanol in DCM eluent to afford product 37 (60% yield). Product 37 was coupled with N-hydroxysuccinimide ester 33 (6 mg) in DIPEA (16 μl) in DMSO (1 mL) at RT for 3 h. Purification by R-HPLC afforded product 38 (1.56 mg). LC MS (m+1=876).

Compound 39.

To a solution of compounds 17 (1.68 mg) and 33 (2 mg, 22 μmol) in DMF (0.5 mL) was added DIPEA (5 μl). The reaction mixture was stirred at RT for 1 h. Purification by R-HPLC afforded product 39 (0.776 mg). LC MS (m+1=777).

Example 9

Adaptation of Compound (IIc) for Conjugation

Figure 9:
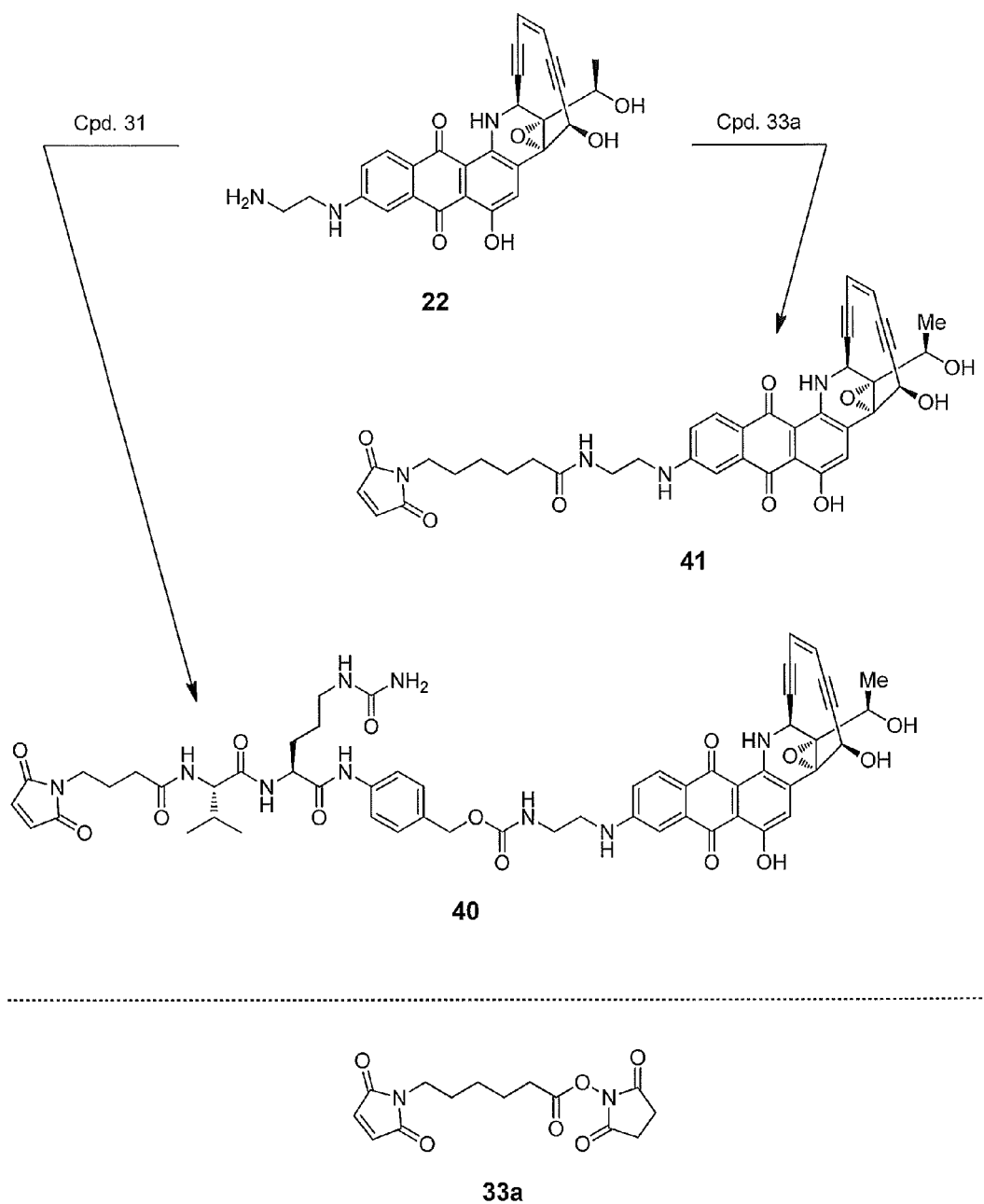

FIG. 9 shows reaction schemes for adapting compound (IIc) for conjugation.

Compound 40.

A solution of compound 22 (4.89 mg, 8 μmol), compound 31 (5.68 mg, 8.00 μmol) and DIPEA (6.95 μl, 40.0 μmol) in DMSO (3 mL) were stirred at RT for 1 h. Purification by R-HPLC and lyophilization yielded 4.6 mg of desired compound 40 (54% yield). LC MS (m/2+1=535). $^1$H NMR (400 MHz, DMSO-$d_6$): δ 13.07 (s, 1H), 9.87 (m, 1H), 8.37 (s, 1H), 8.01 (d, J=7.2 Hz, 1H), 7.91 (d, J=8.4 Hz, 1H), 7.77 (d, J=8.4 Hz, 1H), 7.51 (d, J=8.8 Hz, 1H), 7.2 (m, 5H), 6.95 (m, 3H), 5.92 (dd, J=30, 9.2 Hz, 2H), 5.35 (m, 2H), 5.08 (s, 1H), 4.08 (t, J=7.6 Hz, 1H), 3.31 (t, J=6.8 Hz, 1H), 2.93 (m, 2H), 2.09 (m, 2H), 1.90 (m, 1H), 1.63 (m, 2H), 1.29 (d, J=6.4 Hz, 3H), 0.78 (m, 6H).

Compound 41.

To a solution of compound 22 (4.89 mg, 8 μmol) in DMSO (3 mL) was added DIPEA (4.35 μl, 25.00 μmol) and compound 33a (TCI, 2.466 mg, 8.00 μmol). The reaction mixture was stirred at RT. After 30 min another 0.5 equiv of compound 33a and DIPEA (5 equiv) were added and stirring continued for 30 min. HPLC and LCMS showed the reaction was complete. Purification by R-HPLC and lyophilization yielded 2.35 mg of compound 41 (43% yield). LC MS (m+1=691.3). $^1$H NMR (400 MHz, DMSO-$d_6$): δ 13.07 (s, 1H), 9.87 (m, 1H), 8.38 (s, 1H), 7.89 (m, 2H), 7.1-7.5 (m, 2H), 6.7-7.0 (m, 4H), 6.4-6.6 (m, 2H), 5.92 (dd, J=30.4, 10.0 Hz, 2H), 5.28 (m, 1H), 5.08 (s, 1H), 4.91 (m, 1H), 4.24 (m, 1H), 1.98 (m, 4H), 1.40 (m, 2H), 1.24 (d, J=6.0 Hz, 3H), 1.0-1.2 (m, 4H).

Example 10

Adaptation of Compound (IId) for Conjugation

Figure 10:
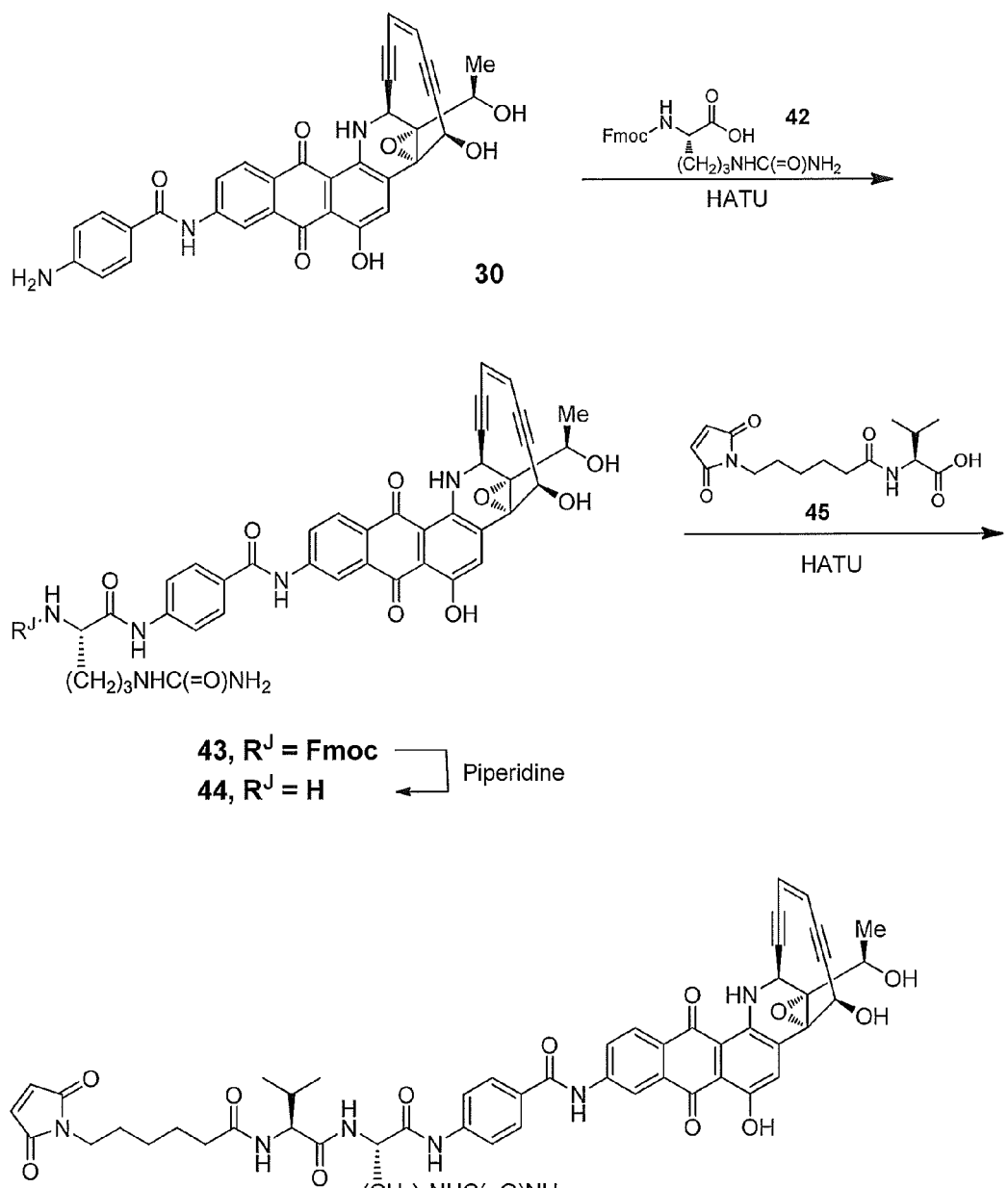

FIG. 10 shows a reaction scheme for adapting compound (IId) (labeled 30) for conjugation.

Compound 43.

DIPEA (0.012 mL, 68.3 μmol) was added to a solution of compound 30 (6.53 mg, 11.39 μmol), Fmoc-protected citrulline 42 (Chem-Impex, 9.05 mg, 22.77 μmol), and N,N,N',N'-tetramethyl-O-(7-azabenzotriazol-1-yl)uronium hexafluorophosphate (HATU, 8.66 mg, 22.77 μmol) in DMF (1 mL). The reaction mixture was stirred at RT for 16 h and was worked up with saturated $NaHCO_3$ solution and brine. Purification by COMBIFLASH™ chromatography on a 12 g silica column using 12% MeOH in DCM eluent yielded product 43 (29% yield). LCMS [[M+1]=953.

Compound 44.

To a solution of compound 43 (4 mg, 4.20 μmol) in DMF (0.8 mL) was added piperidine (200 μL, 2.020 mmol). After stirring at RT for 15 min, LCMS showed that the reaction was complete. The piperidine was removed by rotary evaporation. The reaction mixture was absorbed on silica gel and purified by COMBIFLASH™ chromatography with 25-65% MeOH/DCM gradient as eluent to afford compound 44 (80% yield). LCMS [M+1]=731.

Maleimido Compound 45.

EDC (2 equiv.) was added to a solution of t-butanol (1 equiv), t-butyl valine (1.05 equiv) and maleimide (2.11 g, 1.0 Equiv.) in DCM (50 mL) at RT. After 1 h, the mixture was taken up in EtOAc, which was washed with aqueous citric acid, aqueous sodium bicarbonate and brine. The organic phase was dried and concentrated by evaporation to remove solvent. The residue was passed through a column (EtOAc/Hexane 0-80% gradient) to give 3.02 g of an oil. This oil was dissolved in DCM-TFA (3:2; 20 mL) at RT. After 4 h the solution was evaporated down and dried under high vacuum overnight to give compound 45 as a white solid (2.1 g, 68% yield). LCMS: (M+1)=311.

Compound 46.

To a solution of maleimido compound 45 (3.12 mg, 10.06 μmol) and compound 44 (2.45 mg, 3.35 μmol) in DMF (1 mL) was added HATU (4.59 mg, 0.012 mmol) followed by DIPEA (5.26 μl, 0.030 mmol). The reaction mixture was stirred at RT for 17 h. Purification by R-HPLC afforded product 46 (0.455 mg, 13% yield). LCMS (m+1=1023).

Example 11

Conjugation with an Anti-Mesothelin Antibody

This example describes the conjugation of compounds (IVe) (labeled 41) in FIG. 9, and (IVf) (labeled 40 in FIG. 9) with an anti-mesothelin antibody.

The monoclonal anti-mesothelin antibody 6A4 (Terrett et al., WO 2009/045957 A1), at a concentration of 5.3 mg/mL in 100 mM sodium phosphate, 150 mM NaCl, pH 8.0, was thiolated with a 10-fold molar excess of 2-iminothiolane. The thiolation reaction was allowed to proceed for 1 hour at RT with continuous stirring.

Following thiolation, antibody 6A4 was buffer-exchanged into conjugation buffer (50 mM HEPES, 5 mM glycine, pH 7.0) via a PD10 column (Sephadex G-25). The concentration of the thiolated antibody was determined by UV spectroscopy at 280 nm. The thiol concentration was measured using the dithiodipyridine assay.

A 2 mM stock solution of compound (IVe) or (IVf), as the case might be, in DMSO was added at a 1.5-fold molar excess per thiol group in antibody 6A4. DMSO was added to make a final concentration of 20% and then TWEEN-80™ to a final concentration of 0.1%. The reaction mixture was stirred for 2 h at RT. Following this conjugation step, 100 mM N-ethylmaleimide (NEM) in DMSO was added at a 10-fold molar excess over thiol groups in antibody 6A4 to quench any unreacted thiol groups. The quenching reaction was allowed to proceed for one h at RT with continuous stirring.

The conjugated antibody 6A4 was filtered through a 0.2 μm filter and then subjected to cation-exchange (CEX) chromatographic purification. A SP Sepharose High Performance CEX column was regenerated with 5 column volumes (CVs) of 50 mM HEPES, 5 mM glycine, 1M NaCl, pH 7.0 buffer. Following regeneration, the column was equilibrated with 3 CVs of equilibration buffer (50 mM HEPES, 5 mM glycine, pH 7.0). The antibody 6A4 conjugate with compound (IVe) or (IVf), as the case might be, was loaded onto the column and the column was washed once with the equilibration buffer. The conjugate was eluted with 50 mM HEPES, 5 mM glycine, 110 mM NaCl, pH 7.0. Eluate was collected in fractions. The column was then regenerated with 50 mM HEPES, 5 mM glycine, 1M NaCl, pH 7.0, to remove protein aggregates and any unreacted compound (IVe) or (IVf).

Eluate fractions containing monomeric antibody conjugate were pooled. Antibody conjugate concentration and substitution ratios were determined by measuring absorbance at 280 and 560 nm.

The purified CEX eluate pool of conjugate was buffer exchanged into 50 mM HEPES, 5 mM glycine, 100 mM NaCl, 0.01% TWEEN 80™, pH 7.0, by dialysis using a 10 MWCO membrane. Post-dialysis, antibody conjugate concentration and substitution ratios are determined by measuring absorbance at 280 and 560 nm. The characteristics of the conjugates obtained are summarized in Table 1, below:

TABLE 1

| Conjugation with Anti-mesothelin Antibody 6A4 | | | | | |
|---|---|---|---|---|---|
| Conjugate | Concentration (mg/mL) | Substitution ratio | Aggregation (%) | Total Amount (mg) | Yield (%) |
| 6A4-Cpd (IVe) | 1.51 | 1.0 | 11.0 | 7.55 | 73 |
| 6A4-Cpd (IVf) | 1.23 | 1.2 | 12.0 | 6.15 | 58 |

Example 12

Conjugation with an Anti-CD70 Antibody

This example describes the conjugation of compounds (IVe) and (Ivf) with an anti-CD70 antibody.

The monoclonal anti-CD70 antibody 2H5 (Terrett et al., US 2009/0028872 A1), at a concentration of 5.5 mg/mL in 20 mM sodium phosphate, 50 mM NaCl, 0.02% TWEEN-80™, pH 7.5, was thiolated with a 15-fold molar excess of 2-iminothiolane. The thiolation reaction was allowed to proceed for 1 h at RT with continuous stirring.

Following thiolation, antibody 2H5 was buffer-exchanged into conjugation buffer (50 mM HEPES, 5 mM glycine, pH 7.0) via a PD10 column (Sephadex G-25). The concentration of the thiolated antibody was determined by UV spectroscopy at 280 nm. The thiol concentration was measured using the dithiodipyridine assay.

A 2 mM stock solution of compound (We) or (IVf), as the case might be, in DMSO was added at a 1.5-fold molar excess per thiol group in antibody 2H5. DMSO was added to make a final concentration of 20% and TWEEN-80™ to a final concentration of 0.1%. The reaction medium was stirred for 2 h at RT. Following this conjugation step, 100 mM NEM in DMSO was added at a 10-fold molar excess over thiol groups in antibody 6A4 to quench any unreacted thiol groups. The quenching reaction was allowed to proceed for one h at RT with continuous stirring.

The conjugated antibody 2H5 was filtered through a 0.2 μm filter and then subjected to CEX chromatographic purification. A SP Sepharose High Performance CEX column was regenerated with 5 CVs of 50 mM HEPES, 5 mM glycine, 1M NaCl, pH 7.0 buffer. Following regeneration, the column was equilibrated with 3 CVs of equilibration buffer (50 mM HEPES, 5 mM glycine, pH 7.0). The antibody 2H5 conjugate with compound (IVe) or (IVf), as the case might be, was loaded onto the column and the column was washed once with the equilibration buffer. The conjugate was eluted with 50 mM HEPES, 5 mM glycine, 110 mM NaCl, pH 7.0. Eluate was collected in fractions. The column was then regenerated with 50 mM HEPES, 5 mM glycine, 1M NaCl, pH 7.0, to remove protein aggregates and any unreacted compound (We) or (IVf).

The conjugate containing fractions were pooled, buffer exchanged, and dialyzed as described in the previous example. The characteristics of the conjugate obtained are summarized in Table 2.

TABLE 2

Conjugation with Anti-CD70 Antibody 2H5

| Conjugate | Concentration (mg/mL) | Substitution ratio | Aggregation (%) | Total Amount (mg) | Yield (%) |
|---|---|---|---|---|---|
| 2H5-Cpd (IVe) | 0.87 | 1.38 | 8.1 | 6.52 | 59 |
| 2H5-Cpd (IVf) | 1.14 | 4.8 | 9.5 | 8.55 | 77 |

Example 13

Biological Activity of Compounds

The antiproliferative activity of compounds of this invention or their conjugates was assayed as follows. Human tumor cell lines were obtained from the American Type Culture Collection (ATCC), P.O. Box 1549, Manassas, Va. 20108, USA, and cultured according to instruction from the ATCC. Cells were seeded at $1.0 \times 10^3$ or $1.0 \times 10^4$ cells/well in 96-well plates for 3 h for ATP assays or $^3$H thymidine assays, respectively. 1:3 serial dilutions of free (unconjugated) compounds or their conjugates were added to the wells. Plates were allowed to incubate for 24 to 72 h. The $^3$H thymidine plates were pulsed with 1.0 µCi of $^3$H-thymidine per well for the last 24 hours of the total incubation period, harvested, and read on a Top Count Scintillation Counter (Packard Instruments, Meriden, Conn.). ATP levels in the ATP plates were measured using the CELLTITER-GLO® Luminescent Cell Viability kit following the manufacturer's manual and read on a GLO-MAX® 20/20 luminometer (both from Promega, Madison, Wis., USA). The $EC_{50}$ values—the concentration at which an agent inhibits or reduces cell proliferation by 50%—were determined using PRISM™ software, version 4.0 (GraphPad Software, La Jolla, Calif., USA).

Figure 11A:
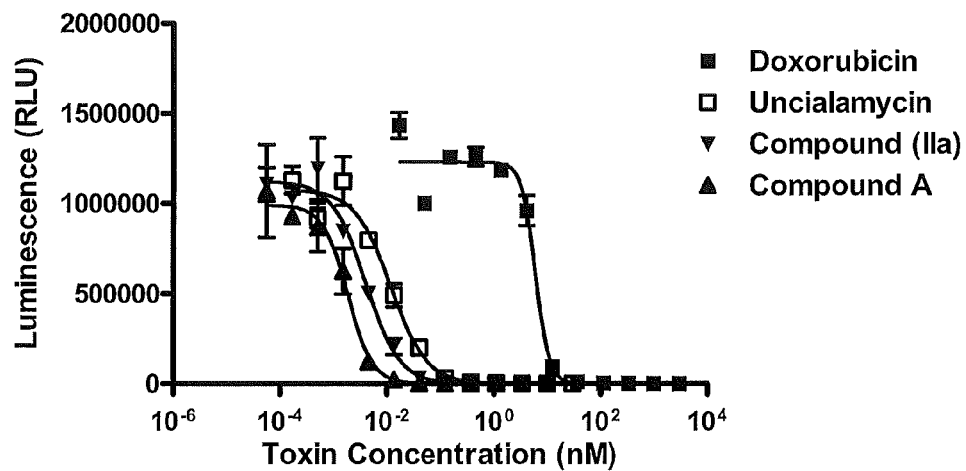
FIGS. 11a and 11b show plots of the antiproliferative activity of a compound of this invention, compared to selected reference compounds.

FIG. 11a is a plot of the antiproliferative activity of compound (IIa) against HL-60 leukemia cells, as measured by the ATP assay using a 72 h incubation period, compared against three reference compounds: doxorubicin (adriamycin), uncialamycin, and Compound A, which is a DNA alkylating agent having the following structure:

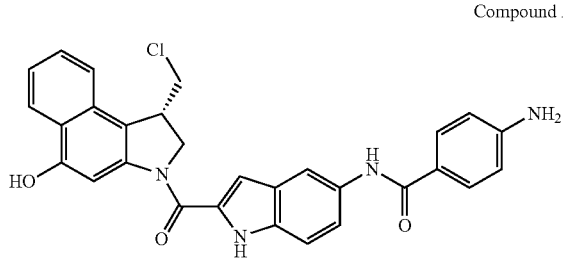

Compound A

The $EC_{50}$ values derived from FIG. 11a are shown in Table 3. The potency of compound (IIa) was greater than that of uncialamycin itself

TABLE 3

Activity of Compound (IIa) against HL-60 Leukemia Cells

| | Doxorubicin | Uncialamycin | Compound (IIa) | Compound A |
|---|---|---|---|---|
| $EC_{50}$ (nM) | 5.979 | 0.01199 | 0.00404 | 0.001872 |

Figure 11B:
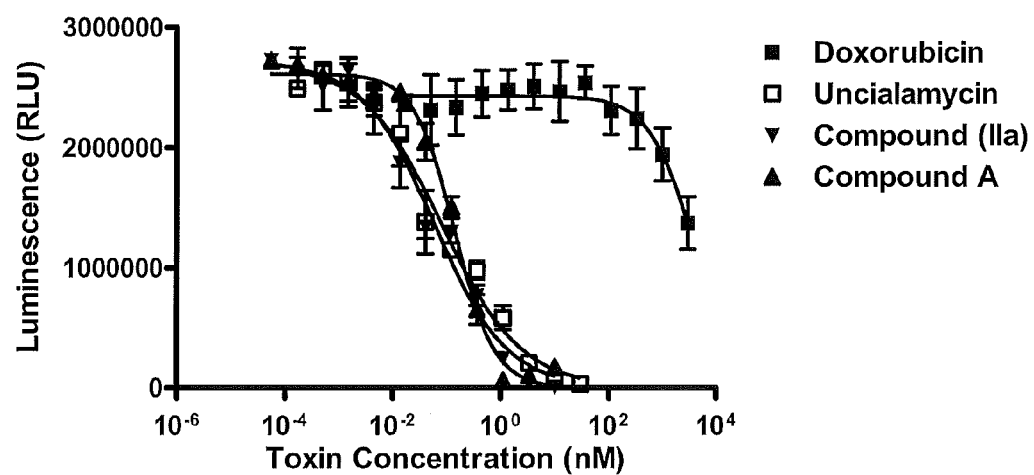

FIG. 11b is an analogous plot of antiproliferative activity against a doxorubicin-resistant ovarian cancer cell line (Adr), also using the ATP assay and a 72 h incubation period. The corresponding $EC_{50}$ values are shown in Table 4. The potency of compound (IIa)—again even greater than that of uncialamycin itself—is noteworthy in view of the loss of potency of doxorubicin and Compound A when confronted with a resistant cell line.

TABLE 4

Activity of Compound (IIa) against Adr Cells

| | Doxorubicin | Uncialamycin | Compound (IIa) | Compound A |
|---|---|---|---|---|
| $EC_{50}$ (nM) | 3846 | 0.08502 | 0.06118 | 0.1432 |

Table 5 shows additional antiproliferative data for Compound (IIa), compared to two other toxins that have been used in conjugates: Compound A and doxorubicin. The assay method was the ATP method. The cancer cell lines tested against were A2780 (ovarian), A549 (lung), CCRF-CEM (acute lymphoblastic leukemia), COLO205 (colon), DU4475 (breast), H2087 (lung, non-small cell), H661 (lung, large cell), HCT116 (colon), LNCaP (prostate), LS174T (colon), MDA MB468 (breast), MDA MB231 (breast), and SET2 (leukemia). The antiproliferative effects are reported as $IC_{50}$'s, i.e., the concentration of toxin that produces a 50% inhibitory effect.

TABLE 5

Antiproliferative Activity of Compound (IIa) against Cancer Cell Lines

| | $IC_{50}$ (nM) | | |
|---|---|---|---|
| Cell Line | Compound A | Doxorubicin | Compound (IIa) |
| A2790 | 0.004 | 11.2 | 0.003 |
| A549 | 0.04 | 138.5 | 0.076 |
| CCRF-CEM | 0.019 | 19.4 | 0.014 |
| COLO205 | 0.019 | 19.7 | 0.01 |
| DU4475 | 0.001 | 2.9 | 0.002 |
| H2087 | 0.019 | 54.4 | 0.037 |
| H661 | 0.02 | 26.6 | 0.053 |
| HCT116 | 0.002 | 23.4 | 0.007 |
| LNCaP | 0.01 | 5.5 | 0.001 |
| LS174T | 0.015 | 11.1 | 0.002 |
| MDA MB468 | 0.009 | 29 | 0.012 |
| MCD MB231 | 0.068 | 90.5 | 0.085 |
| SET2 | 0.002 | 67.6 | 0.008 |

Figure 12A:
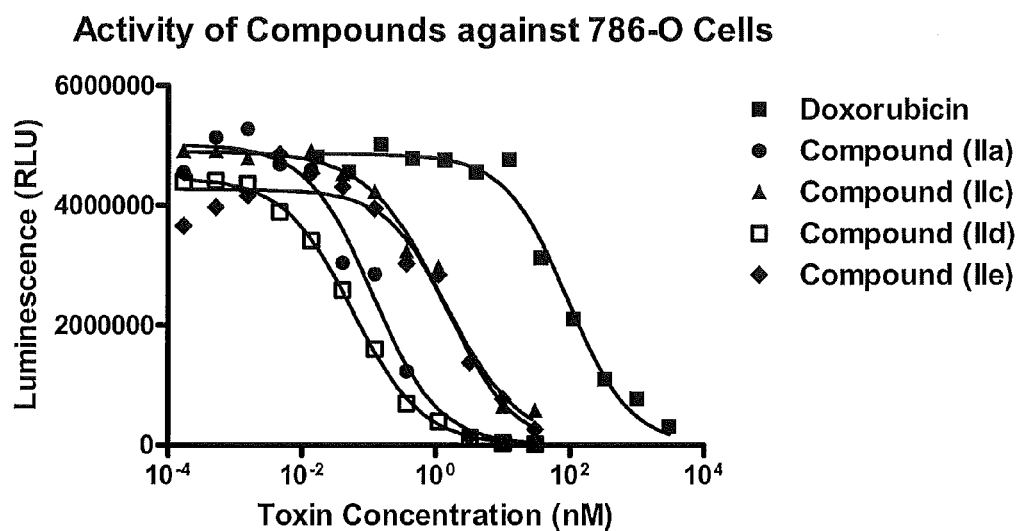
FIGS. 12a and 12b show plots of the antiproliferative activity of additional compounds of this invention, compared to selected reference compounds.

FIG. 12a shows additional antiproliferative data, for compounds (IIa), (IIc), (IId), and (IIe), with doxorubicin as a comparative compound, against 786-O renal cancer cells. The $EC_{50}$ values derived from FIG. 12a are provided in Table 6. The ATP assay was used, with a 72 h incubation period.

TABLE 6

Antiproliferative Activity of Compounds against 786-O Cells

| | Doxorubicin | Cpd. (IIa) | Cpd. (IIc) | Cpd. (IId) | Cpd. (IIe) |
|---|---|---|---|---|---|
| $EC_{50}$ (nM) | 92.31 | 0.1160 | 1.275 | 0.05803 | 1.716 |

Figure 12B:
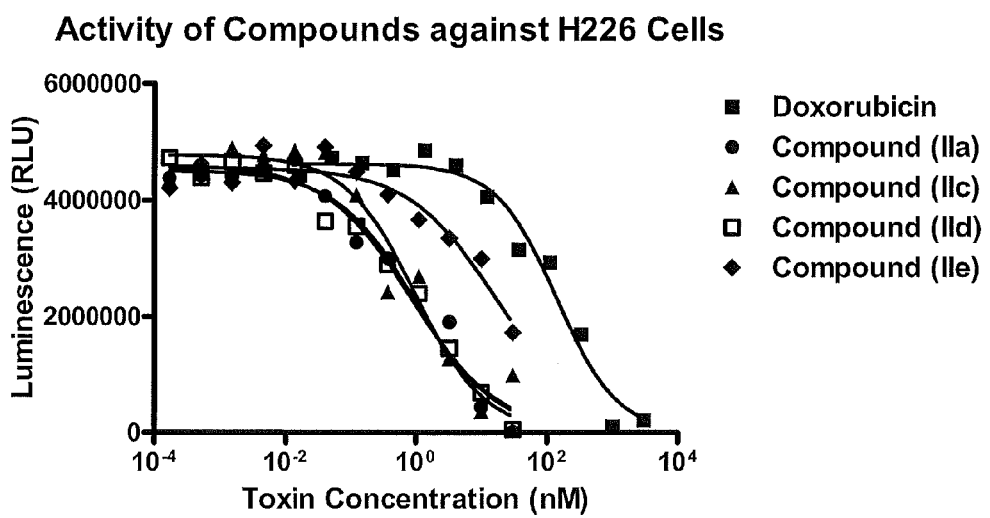

FIG. 12b is a similar antiproliferative plot, but against H226 lung cancer cells. The derived $EC_{50}$ values are provided in Table 7. The ATP assay was used, with a 72 h incubation period.

TABLE 7

Antiproliferative Activity of Compounds against H226 Cells

|  | Doxorubicin | Cpd. (IIa) | Cpd. (IIc) | Cpd. (IId) | Cpd. (IIe) |
|---|---|---|---|---|---|
| $EC_{50}$ (nM) | 141.2 | 1.001 | 0.9859 | 0.8729 | 17.45 |

Example 14

Biological Activity of Conjugates

Using the same assay methods described hereinabove, the antiproliferative activity of conjugates made from compounds of this invention were measured.

FIG. 13a shows the antiproliferative activity against 786-O cells, using the $^3$H thymidine incorporation assay (72 h incubation), of four conjugates made from compounds of this invention: (a) a conjugate of antibody 2H5 (anti-CD70, Terrett et al., US 2009/0028872 A1) with compound (IVf), (b) a conjugate of antibody 6A4 (anti-mesothelin, Terrett et al., WO 2009/045957 A1) with compound (IVf), (c) a conjugate of antibody 2H5 with compound (IVe), and (d) a conjugate of antibody 6A4 with compound (IVe). In FIG. 13a (and also in subsequent FIGS. 13b and 13c), the X-axis values for "Toxin Concentration" are adjusted for the substitution ratio (SR)—that is, the values are equal to the molar concentration of the conjugate times SR. The $EC_{50}$ values derived from the plots in FIG. 13a are provided in Table 8.

TABLE 8

Activity of Conjugates against 786-O Cells

|  | 2H5-(IVf) | 6A4-(IVf) | 2H5-(IVe) | 6A4-(IVe) |
|---|---|---|---|---|
| $EC_{50}$ (nM) | 0.7629 | 33.37 | 19.68 | 27.43 |

FIG. 13b shows the antiproliferative activity of the same four conjugates against H226 cells, again using the $^3$H thymidine incorporation assay and a 72 h incubation period. The derived $EC_{50}$ values are shown in Table 9.

TABLE 9

Activity of Conjugates against H226 Cells

|  | 2H5-(IVf) | 6A4-(IVf) | 2H5-(IVe) | 6A4-(IVe) |
|---|---|---|---|---|
| $EC_{50}$ (nM) | 12.37 | 0.8822 | 28.24 | 39.60 |

FIG. 13c is another plot of the antiproliferative activity of conjugates 2H5-(IVf) and 6A4-(IVf) against H226 cells, but measured using the ATP assay, with a 72 h incubation period. The derived $EC_{50}$ values were 6.630 and 0.1548 nM, respectively.

The foregoing detailed description of the invention includes passages that are chiefly or exclusively concerned with particular parts or aspects of the invention. It is to be understood that this is for clarity and convenience, that a particular feature may be relevant in more than just the passage in which it is disclosed, and that the disclosure herein includes all the appropriate combinations of information found in the different passages. Similarly, although the various figures and descriptions herein relate to specific embodiments of the invention, it is to be understood that where a specific feature is disclosed in the context of a particular figure or embodiment, such feature can also be used, to the extent appropriate, in the context of another figure or embodiment, in combination with another feature, or in the invention in general.

Further, while the present invention has been particularly described in terms of certain preferred embodiments, the invention is not limited to such preferred embodiments. Rather, the scope of the invention is defined by the appended claims.

REFERENCES

Full citations for the following references cited in abbreviated fashion by first author (or inventor) and date earlier in this specification are provided below. Each of these references is incorporated herein by reference for all purposes.

Davies et al., *Org. Lett.* 2005, 7 (23), 5233-5236.

Davies et al., WO 2007/038868 A2 (2007).

Dubowchik et al., *Bioconjugate Chem.* 2002, 13, 855-869.

Nicolaou et al., *Ang. Chem.* 2007, 119, 4788-4791 [2007a].

Nicolaou et al., *Ang. Chem. Int. Ed.* 2007, 46, 4704-4707 [2007b].

Nicolaou et al., *Ang. Chem. Int. Ed.* 2008, 47, 185-189.

Shao, *Curr. Mol. Pharmacology* 2008, 1, 50-60.

What is claimed is:

1. A method of treating a cancer in a subject suffering from such cancer, comprising administering to the subject a therapeutically effective amount of a compound having a structure represented by formula (IIa), (IIc), (IId), or (IIe), or a conjugate thereof with a targeting moiety:

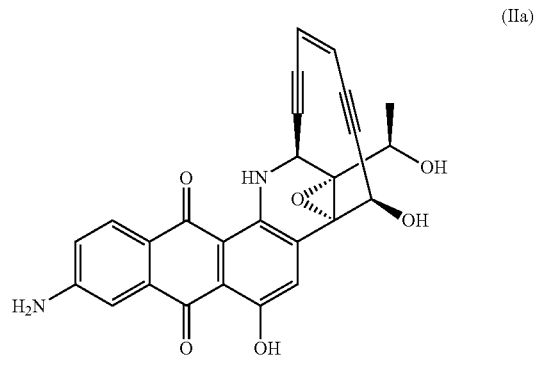 [SMILES: C[C@@H](O)[C@@]12O[C@]13c1cc(O)c4c(c1N[C@H]2C#C/C=C\C#C[C@H]3O)C(=O)c1ccc(N)cc1C4=O]

(IIa)

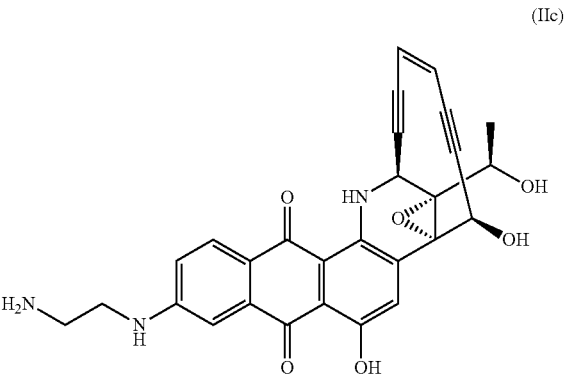 [SMILES: C[C@@H](O)[C@@]12O[C@]13c1cc(O)c4c(c1N[C@H]2C#C/C=C\C#C[C@H]3O)C(=O)c1ccc(NCCN)cc1C4=O]

(IIc)

-continued

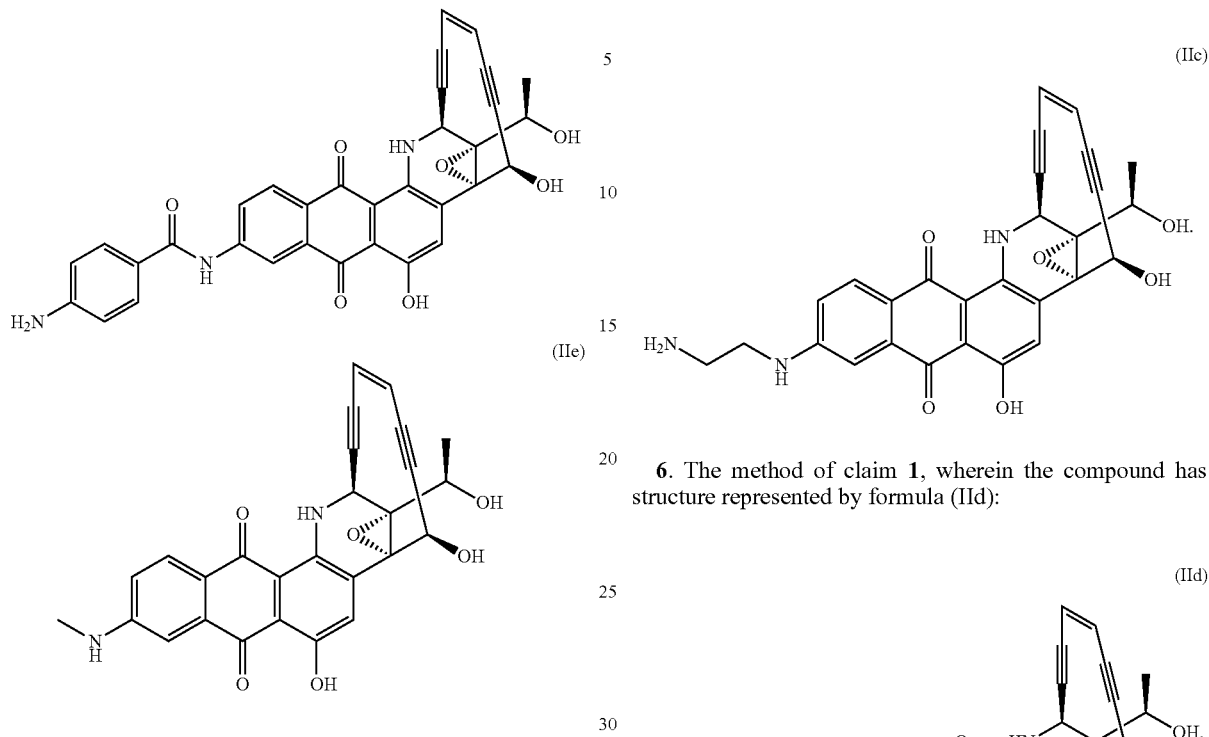

or a pharmaceutically acceptable salt thereof,
wherein the cancer is selected from the group consisting of leukemia, renal cancer, ovarian cancer, lung cancer, colon cancer, breast cancer, and prostate cancer.

2. The method of claim 1, wherein the compound is conjugated to a targeting moiety that is an antibody.

3. The method of claim 2, wherein the antibody binds to an antigen that is overexpressed or uniquely expressed by the cancer.

4. The method of claim 1, wherein the compound has structure represented by formula (IIa):

5. The method of claim 1, wherein the compound has structure represented by formula (IIc):

6. The method of claim 1, wherein the compound has structure represented by formula (IId):

7. The method of claim 1, wherein the compound has structure represented by formula (IIe):

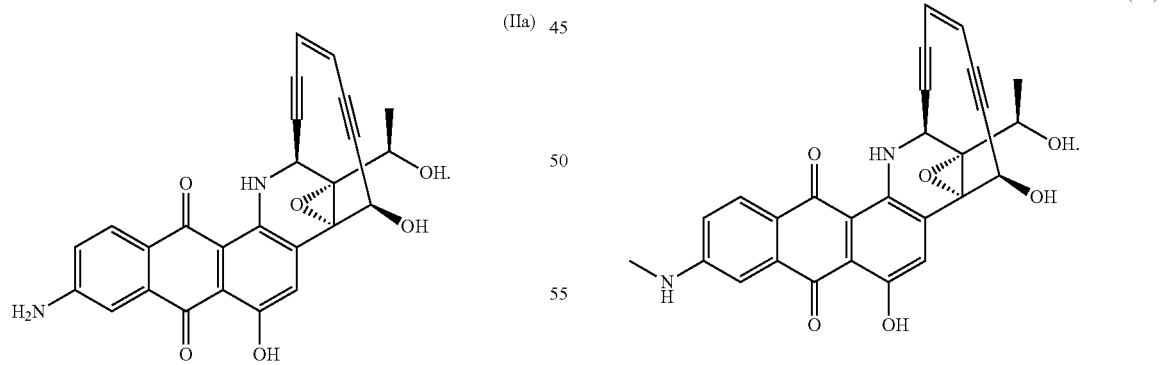

* * * * *